United States Patent
Patel et al.

(10) Patent No.: US 11,284,916 B2
(45) Date of Patent: Mar. 29, 2022

(54) ATHERECTOMY CATHETERS AND OCCLUSION CROSSING DEVICES

(71) Applicant: Avinger, Inc., Redwood City, CA (US)

(72) Inventors: Himanshu N. Patel, San Jose, CA (US); John B. Simpson, Woodside, CA (US); Anthony J. Fernandez, San Mateo, CA (US); Richard R. Newhauser, Redwood City, CA (US); Priyanshu Gupta, Hornsby (AU); Michael Zung, San Carlos, CA (US); Wendy Ngo Lam, San Jose, CA (US); Maegan K. Spencer, Emerald Hills, CA (US); Peter Howard Smith, Pacifica, CA (US); Stephen C. Davies, El Dorado Hills, CA (US); Nicholas J. Spinelli, San Carlos, CA (US); Charles W. McNall, Cottonwood Heights, UT (US); Theodore W. Ketai, San Francisco, CA (US); Manish Kankaria, Fremont, CA (US); Mark W. Askew, San Francisco, CA (US); Kent C. B. Stalker, San Marcos, CA (US)

(73) Assignee: Avinger, Inc., Redwood City, CA (US)

( * ) Notice: Subject to any disclaimer, the term of this patent is extended or adjusted under 35 U.S.C. 154(b) by 273 days.

(21) Appl. No.: 16/681,807

(22) Filed: Nov. 12, 2019

(65) Prior Publication Data

US 2020/0315654 A1 Oct. 8, 2020

Related U.S. Application Data

(63) Continuation-in-part of application No. 15/354,842, filed on Nov. 17, 2016, now Pat. No. 10,470,795, (Continued)

(51) Int. Cl.
*A61B 5/00* (2006.01)
*A61B 17/3207* (2006.01)
(Continued)

(52) U.S. Cl.
CPC .... *A61B 17/320783* (2013.01); *A61B 5/0066* (2013.01); *A61B 5/0084* (2013.01); (Continued)

(58) Field of Classification Search
CPC .............. A61B 90/37; A61B 17/12031; A61B 17/1204; A61B 17/12109; (Continued)

(56) References Cited

U.S. PATENT DOCUMENTS 3,367,727 A 2/1968 Ward et al.
3,908,637 A 9/1975 Doroshow
(Continued)

FOREIGN PATENT DOCUMENTS

CN 1875242 A 12/2006
CN 1947652 A 4/2007
(Continued)

OTHER PUBLICATIONS

Merriam Webster; Proximal (Definition); 10 pages; retrieved from the internet (https://www.merriam-webster.com/dictionary/proximal) on Jun. 9, 2021.
(Continued)

*Primary Examiner* — Joel Lamprecht
(74) *Attorney, Agent, or Firm* — Shay Glenn LLP

(57) ABSTRACT

An atherectomy catheter includes an elongate flexible catheter body, a cutter near the distal end of the catheter body, a drive shaft connected to the cutter and extending within the catheter body, an imaging element near the distal end of the catheter body.

16 Claims, 67 Drawing Sheets

Related U.S. Application Data which is a continuation of application No. 15/076,568, filed on Mar. 21, 2016, now Pat. No. 9,498,247, which is a continuation-in-part of application No. 15/072,272, filed on Mar. 16, 2016, now Pat. No. 9,592,075, which is a continuation-in-part of application No. PCT/US2015/014613, filed on Feb. 5, 2015, application No. 16/681,807, which is a continuation-in-part of application No. 15/457,960, filed on Mar. 13, 2017, now Pat. No. 10,568,655, which is a continuation of application No. 15/072,272, filed on Mar. 16, 2016, now Pat. No. 9,592,075, which is a continuation-in-part of application No. PCT/US2015/014613, filed on Feb. 5, 2015, application No. 16/681,807, which is a continuation-in-part of application No. 14/424,277, filed on Feb. 26, 2015, now Pat. No. 10,548,478.

(60) Provisional application No. 61/936,837, filed on Feb. 6, 2014, provisional application No. 61/697,743, filed on Sep. 6, 2012.

(51) Int. Cl.
*A61M 25/00* (2006.01)
*A61B 90/00* (2016.01)
*A61B 17/12* (2006.01)
*A61M 25/10* (2013.01)
*A61B 17/22* (2006.01)
*A61B 17/00* (2006.01)

(52) U.S. Cl.
CPC .... *A61B 17/1204* (2013.01); *A61B 17/12031* (2013.01); *A61B 17/12109* (2013.01); *A61B 17/12136* (2013.01); *A61B 17/320725* (2013.01); *A61B 17/320758* (2013.01); *A61B 90/37* (2016.02); *A61M 25/0043* (2013.01); *A61M 25/0068* (2013.01); *A61M 25/0074* (2013.01); *A61M 25/0082* (2013.01); *A61M 25/1002* (2013.01); *A61M 25/1011* (2013.01); *A61B 2017/00557* (2013.01); *A61B 2017/00738* (2013.01); *A61B 2017/22067* (2013.01); *A61B 2017/22071* (2013.01); *A61B 2017/320791* (2013.01); *A61B 2090/3735* (2016.02)

(58) Field of Classification Search
CPC ...... A61B 17/12136; A61B 17/320725; A61B 17/320758; A61B 2017/00557; A61M 25/1002
See application file for complete search history.

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,429,136 A | 7/1995 | Milo et al. |
| 5,431,673 A | 7/1995 | Summers et al. |
| 5,437,284 A | 8/1995 | Trimble |
| 5,459,570 A | 10/1995 | Swanson et al. |
| 5,460,168 A | 10/1995 | Masubuchi et al. |
| 5,465,147 A | 11/1995 | Swanson |
| 5,507,760 A | 4/1996 | Wynne et al. |
| 5,507,795 A | 4/1996 | Chiang et al. |
| 5,517,998 A | 5/1996 | Madison |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |

(56) References Cited

U.S. PATENT DOCUMENTS

| | | |
|---|---|---|
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,579,157 B2 | 2/2017 | Moberg |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |

(56) References Cited

U.S. PATENT DOCUMENTS

| | | |
|---|---|---|
| 10,052,125 B2 | 8/2018 | Rosenthal et al. |
| 10,130,386 B2 | 11/2018 | Simpson et al. |
| 10,213,224 B2 | 2/2019 | Guggenheimer et al. |
| 10,244,934 B2 | 4/2019 | Tachibana et al. |
| 10,314,667 B2 | 6/2019 | Garvey et al. |
| 10,335,173 B2 | 7/2019 | Carver et al. |
| 10,342,491 B2 | 7/2019 | Black et al. |
| 10,349,974 B2 | 7/2019 | Patel et al. |
| 10,357,277 B2 | 7/2019 | Patel et al. |
| 10,363,062 B2 | 7/2019 | Spencer et al. |
| 10,406,316 B2 | 9/2019 | Garvey et al. |
| 10,470,795 B2 | 11/2019 | Patel et al. |
| 10,548,478 B2 | 2/2020 | Simpson et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Remzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |

(56) References Cited

U.S. PATENT DOCUMENTS

| | | |
|---|---|---|
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppari et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0035692 A1 | 2/2013 | Sorensen et al. |
| 2013/0072787 A1 | 3/2013 | Wallace et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota |
| 2013/0296695 A1 | 11/2013 | Spencer et al. |
| 2013/0317519 A1 | 11/2013 | Romo et al. |
| 2013/0325003 A1 | 12/2013 | Kapur et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0222042 A1 | 8/2014 | Kessler et al. |
| 2014/0222047 A1 | 8/2014 | Vreeman |
| 2014/0275996 A1 | 9/2014 | Stigall |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0141816 A1 | 5/2015 | Gupta et al. |
| 2015/0146211 A1 | 5/2015 | Bhagavatula et al. |
| 2015/0320975 A1 | 11/2015 | Simpson et al. |
| 2016/0008025 A1 | 1/2016 | Gupta et al. |
| 2016/0038030 A1 | 2/2016 | Smith et al. |
| 2016/0144155 A1 | 5/2016 | Simpson et al. |
| 2016/0262839 A1 | 9/2016 | Spencer et al. |
| 2016/0310700 A1 | 10/2016 | Drake et al. |
| 2016/0354109 A1 | 12/2016 | Guggenheimer et al. |
| 2016/0354110 A1 | 12/2016 | Guggenheimer et al. |
| 2017/0172666 A1 | 6/2017 | Govari et al. |
| 2017/0238803 A1 | 8/2017 | Kankaria |
| 2017/0238808 A1 | 8/2017 | Simpson et al. |
| 2017/0273711 A1 | 9/2017 | Simpson et al. |
| 2018/0042520 A1 | 2/2018 | Patel et al. |
| 2018/0192880 A1 | 7/2018 | Patel et al. |
| 2018/0200488 A1 | 7/2018 | Drake et al. |
| 2018/0207417 A1 | 7/2018 | Zung et al. |
| 2018/0256039 A1 | 9/2018 | Smith et al. |
| 2018/0256187 A1 | 9/2018 | Patel et al. |
| 2018/0364024 A1 | 12/2018 | Baca et al. |
| 2019/0021679 A1 | 1/2019 | Christensen |
| 2019/0021760 A1 | 1/2019 | Newhauser et al. |
| 2019/0029714 A1 | 1/2019 | Patel et al. |
| 2019/0110809 A1 | 4/2019 | Rosenthal et al. |
| 2019/0159796 A1 | 5/2019 | Simpson et al. |
| 2019/0209206 A1 | 7/2019 | Patel et al. |
| 2019/0313941 A1 | 10/2019 | Radjabi |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| EP | 2942028 A1 | 11/2015 |
| JP | S62-275425 A | 11/1987 |
| JP | 03502060 A | 2/1990 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |

(56) References Cited

FOREIGN PATENT DOCUMENTS

| | | |
|---|---|---|
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A1 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |
| WO | WO2015/074018 A1 | 5/2015 |
| WO | WO2015/101747 A1 | 7/2015 |
| WO | WO2015/120146 A1 | 8/2015 |
| WO | WO2015/165736 A1 | 11/2015 |
| WO | WO2017/007853 A1 | 1/2017 |
| WO | WO2017/132247 A1 | 8/2017 |
| WO | WO2018/094041 A1 | 5/2018 |
| WO | WO2019/204797 A1 | 10/2019 |

OTHER PUBLICATIONS

Wikipedia; Hinge; 4 pages; retrieved from the internet (https://en.wikipedia.org/w/index.php?title=Hinge&oldid=479569345) on Jun. 9, 2021.

Smith et al.; U.S. Appl. No. 17/189,123 entitled "Optical pressure sensor Assembly," filed Mar. 1, 2021.

Kankaria; U.S. Appl. No. 17/209,162 entitled "Optical coherence tomography with graded index fiber for biological Imaging," filed Mar. 22, 2021.

Newhauser et al.; U.S. Appl. No. 17/209,168 entitled "Occlusion-crossing Devices," filed Mar. 22, 2021.

Sharma et al.; Common-path optical coherence tomography with side-viewing bare fiber probe for endoscopic optical coherence tomography; vol. 78; 113102; 5 pages; Nov. 6, 2007.

Patel et al.; U.S. Appl. No. 16/801,047 entitled "Micro-molded anamorphic reflector lens for image guided therapeutic/diagnostic Catheters," filed Feb. 25, 2020.

Aziz et al.; Chronic total occlusions—a stiff challenge requiring a major breakthrough: is there light at the end of the tunnel?; Heart; vol. 91; suppl. III; pp. 42-48: Jun. 2005.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Leitgeb et al.; Performance of fourier domain vs time domain optical coherence tomography; Optics Express; 11(8); pp. 889-894; Apr. 21, 2003.

Linares et al.; Arbitrary single-mode coupling by tapered and nontapered grin fiber lenses; Applied Optics; vol. 29; No. 28; pp. 4003-4007; Oct. 1, 1990.

Muller et al.; Time-gated infrared fourier-domain optical coherence tomography; CFM5; San Jose, California; CLEO May 4, 2008; 2 pages.

Rollins et al.; Optimal interferometer designs for optical coherence tomography; Optics Letters: 24(21); pp. 1484-1486; Nov. 1999.

Sharma et al.; Optical coherence tomography based on an all-fiber autocorrelator using probe-end reflection as reference: CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Stamper et al.; Plaque characterization with optical coherence tomography. Journal of the American College of Cardiology. 47(8); pp. 69-79; Apr. 18, 2006.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Fernandez et al., U.S. Appl. No. 16/305,136 entitled "Catheter device with detachable distal End," filed Nov. 28, 2018.

Tachibana et al.; U.S. Appl. No. 16/372,112 entitled "Atherectomy catheter drive Assemblies," filed Apr. 1, 2019.

Patel et al.; U.S. Appl. No. 16/490,903 entitled "Atherctomy Catheter," filed Jul. 2, 2019.

Black et al; U.S. Appl. No. 16/506,851 entitled "Optical coherence tomography for biological Imaging," filed Jul. 9, 2019.

(56) References Cited

OTHER PUBLICATIONS

Patel et al.; U.S. Appl. No. 16/516,093 entitled "High speed chronic total occlusion crossing Devices," filed Jul. 18, 2019.
Patel et al.; U.S. Appl. No. 17/046,066 entitled "Occlusion-crossing Devices," filed Oct. 8, 2020.
Simpson et al.; U.S. Appl. No. 17/075,548 entitled "Identification of elastic lamina to guide interventional Therapy," filed Oct. 20, 2020.
Smith et al.; U.S. Appl. No. 16/941,310 entitled "Chronic total occlusion crossing devices with Imaging," filed Jul. 28, 2020.
Spencer et al.; U.S. Appl. No. 16/943,446 entitled "Catheter-based off-axis optical coherence tomography imaging System," filed Jul. 30, 2020.
Bayer Material Science: ; Snap-Fit Joints for Plastics; 26 pages; retrieved from the Internet: ( https://web.archive.org/web/20121119232733if_/http://fab.cba.mit.edu:80/classes/S62.12/people/vernelle.noel/Plastic_Snap_fit_design.pdf) on Sep. 26, 2018.
Schmitt et al.; A new rotational thrombectomy catheter: System design and first clinical esperiences; Cardiovascular and Interventional Radiology; Sprinver-Verlag; 22(6); pp. 504-509; Nov. 1, 1999.

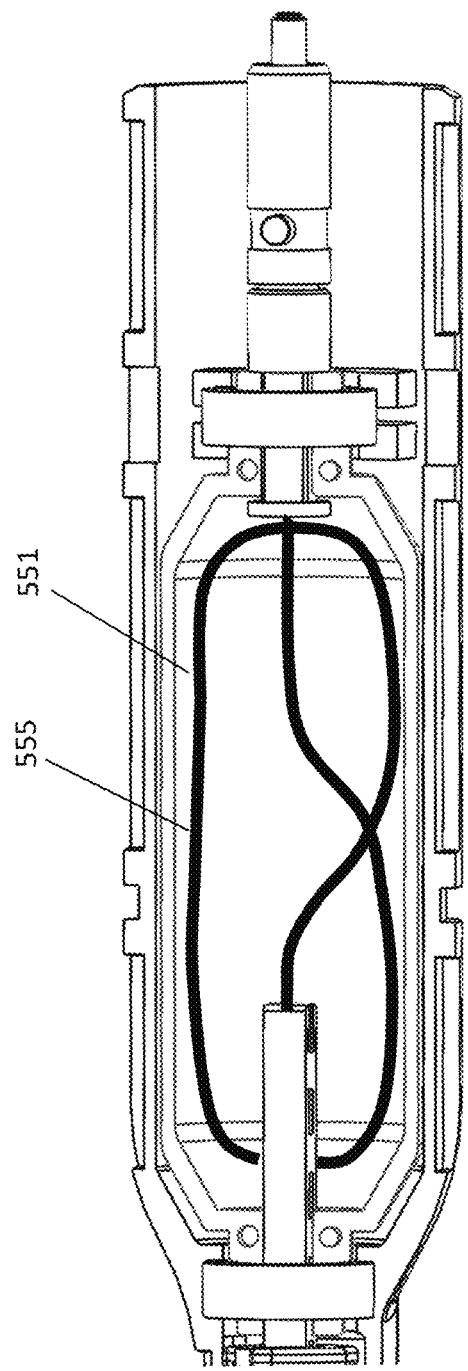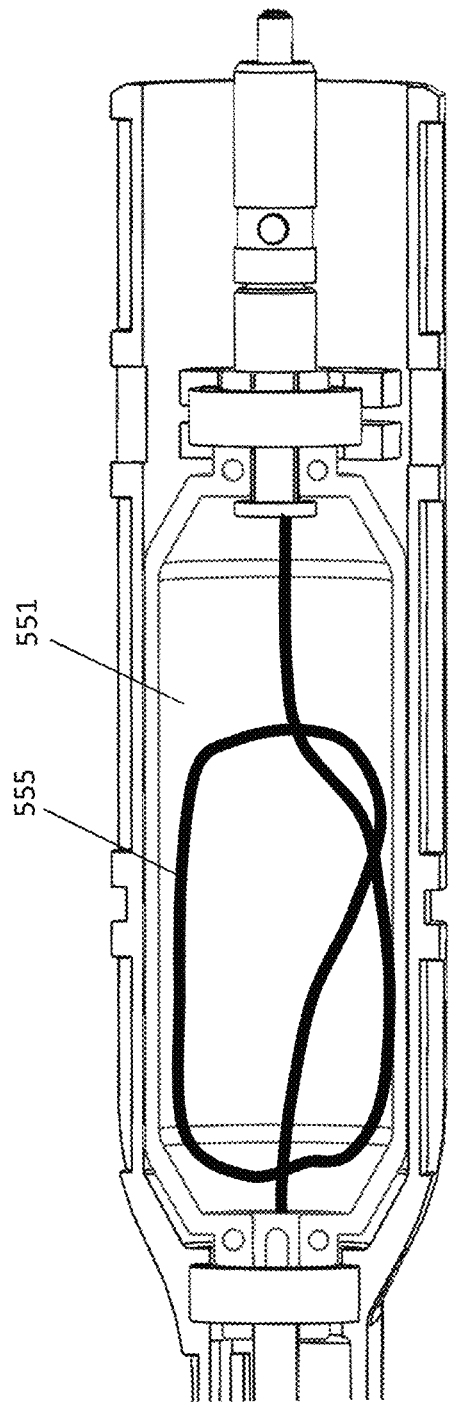
FIG. 5D
FIG. 5E

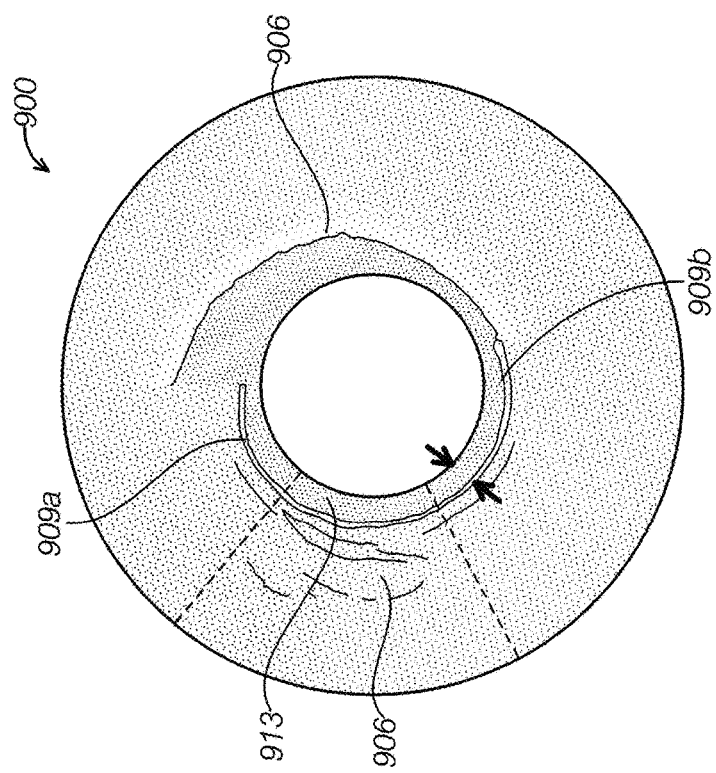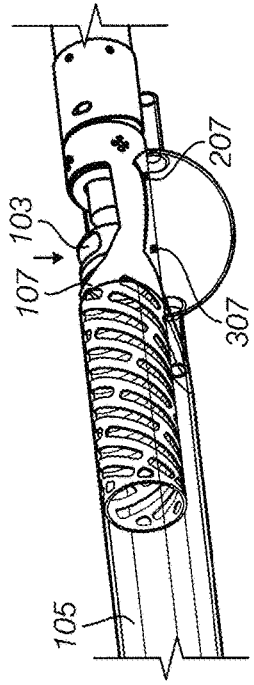
FIG. 9A
FIG. 9B
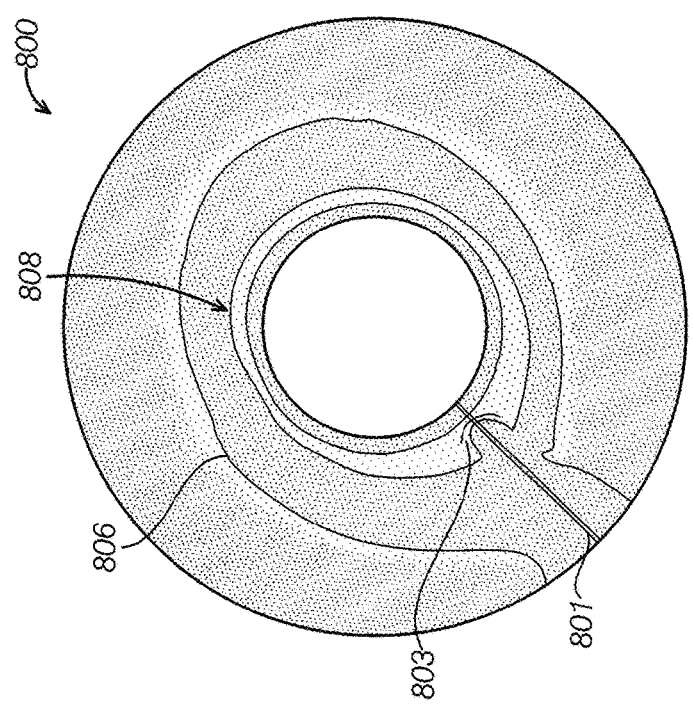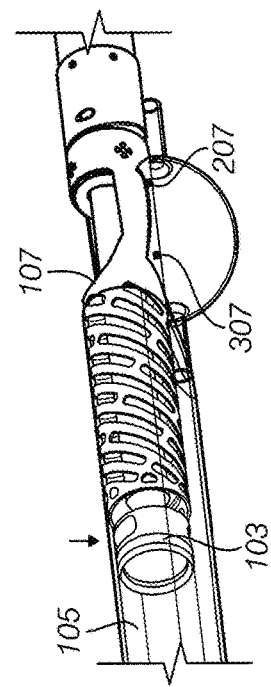
FIG. 8A
FIG. 8B

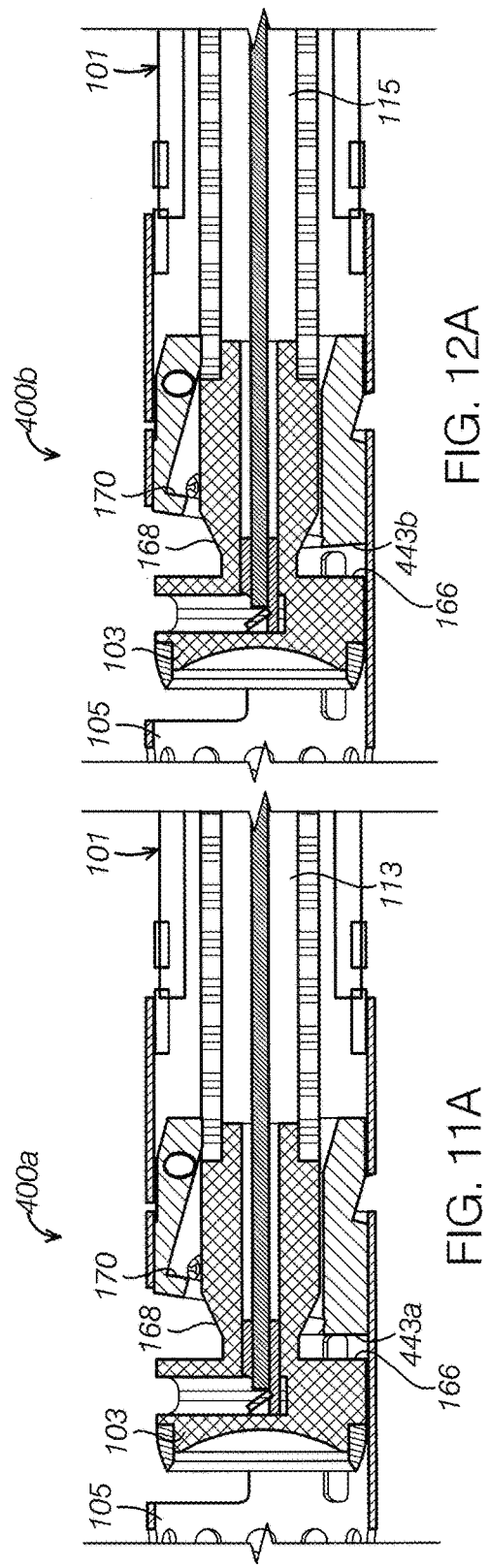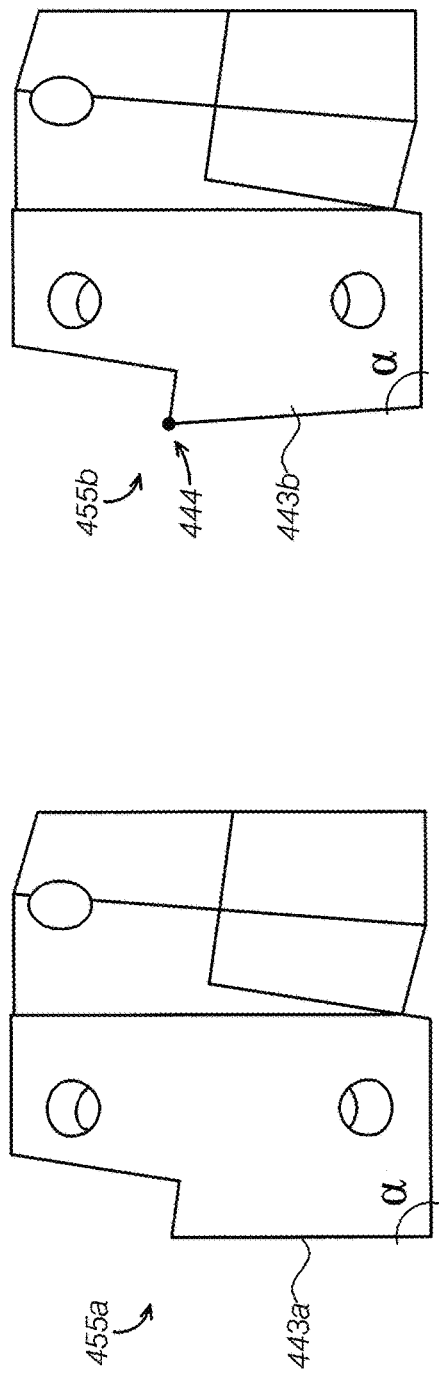

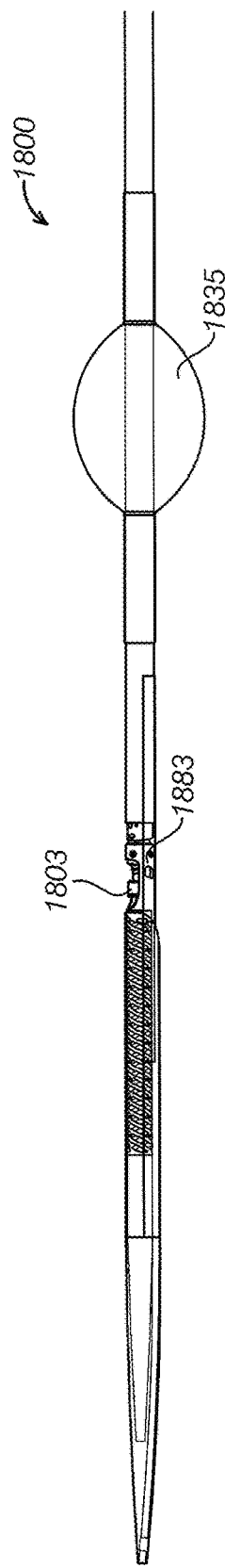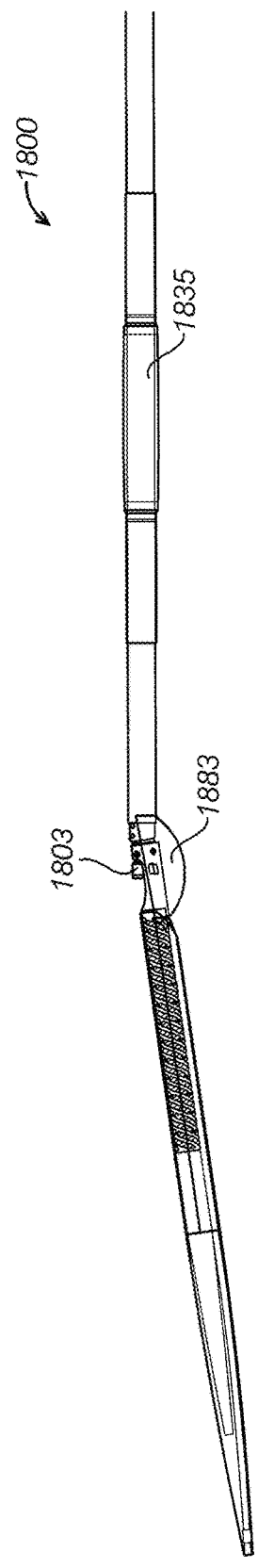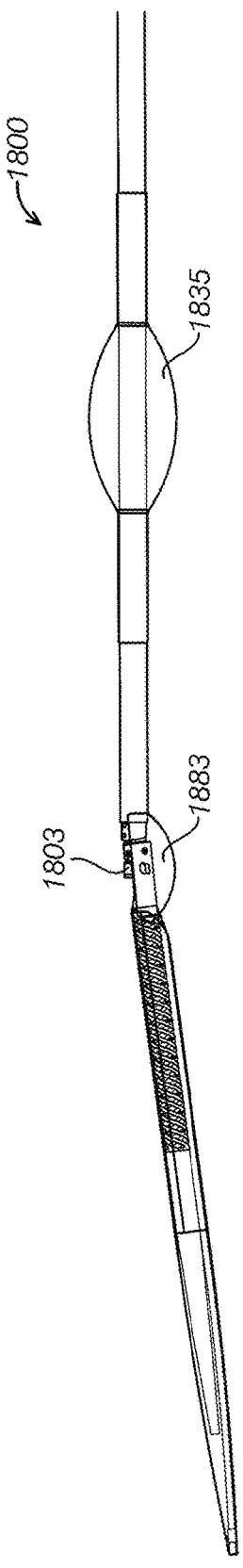

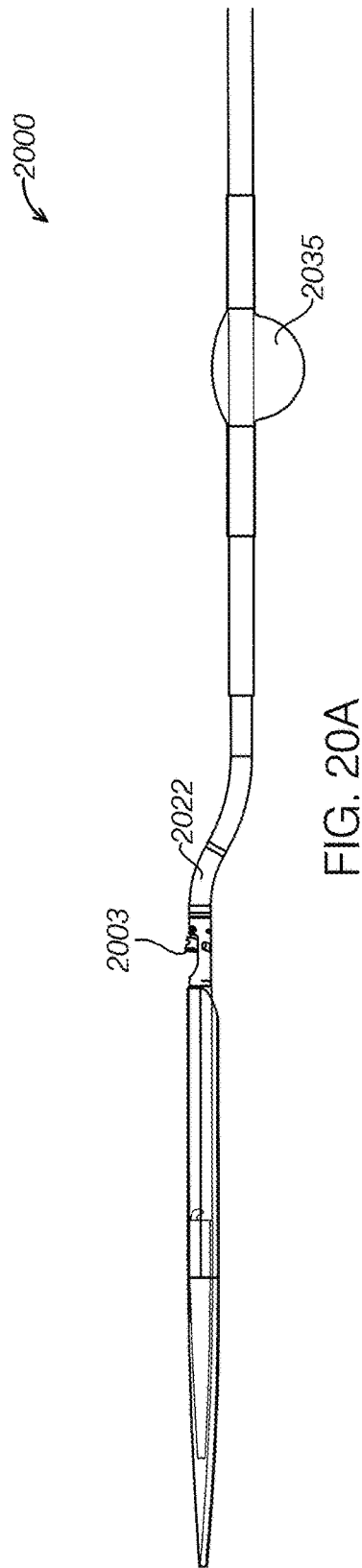
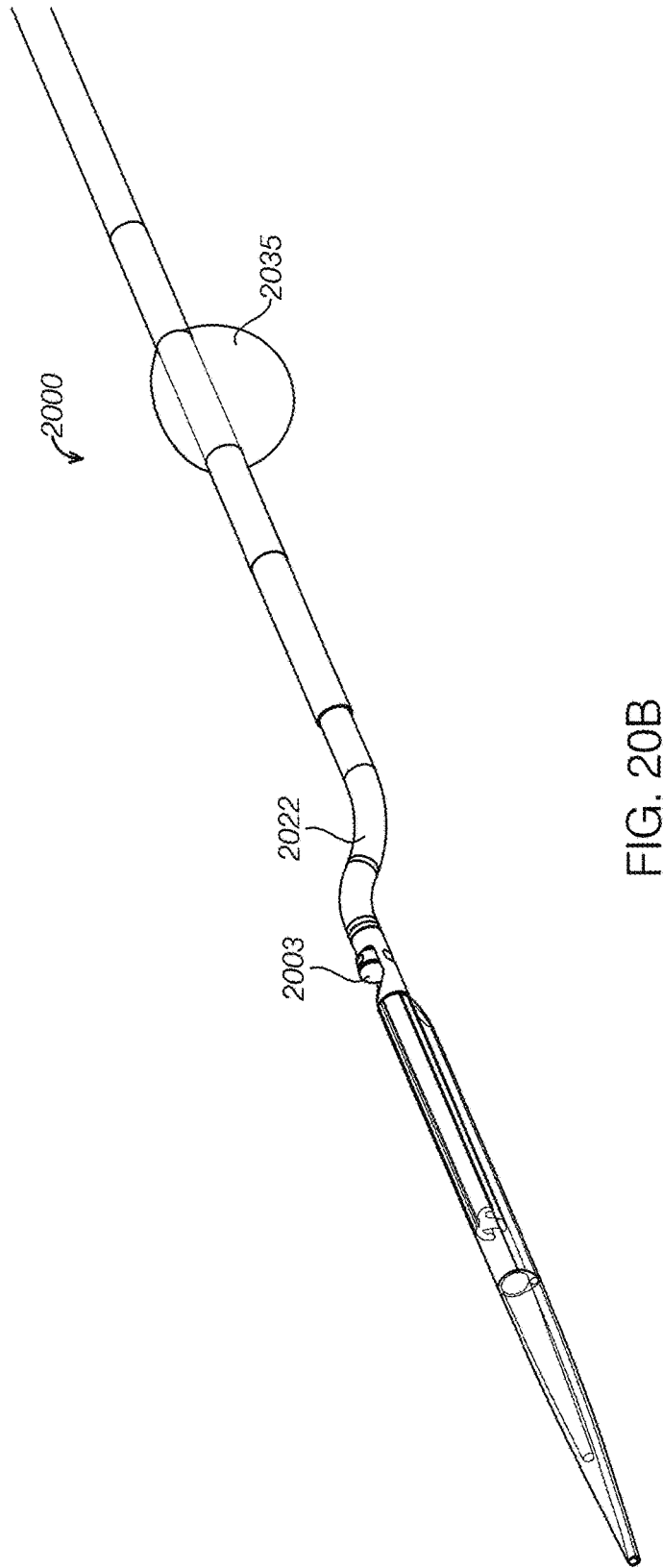

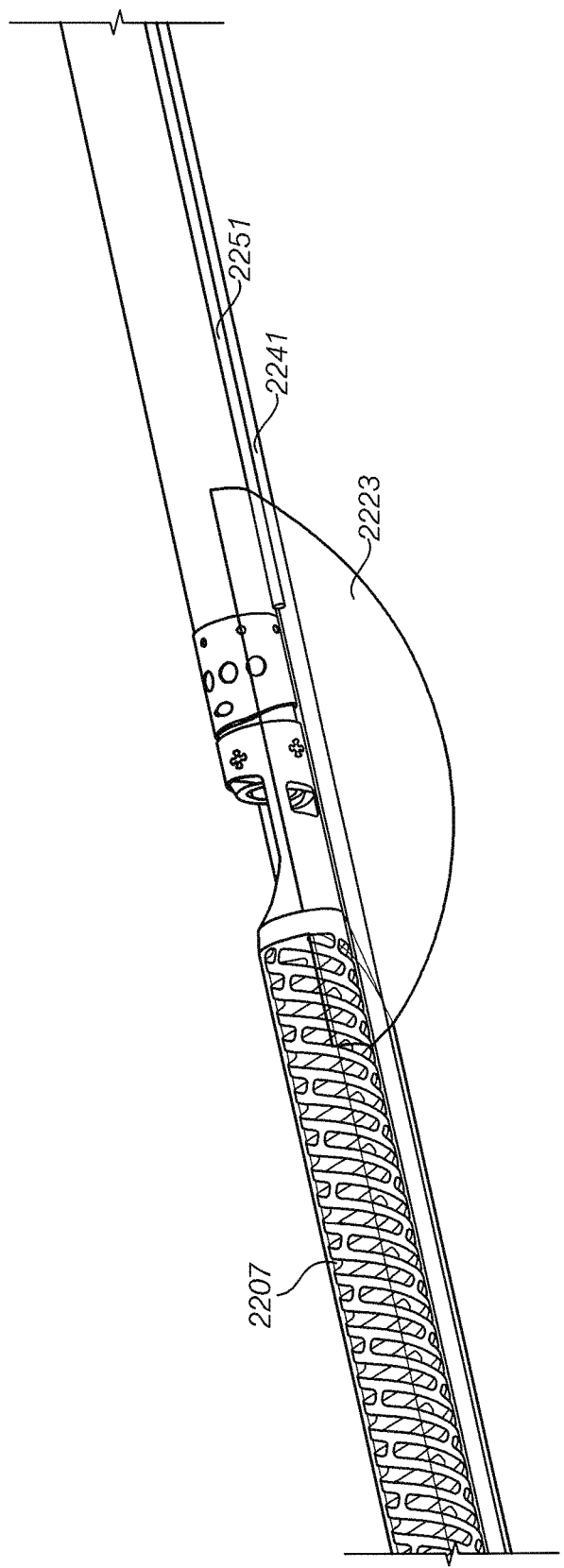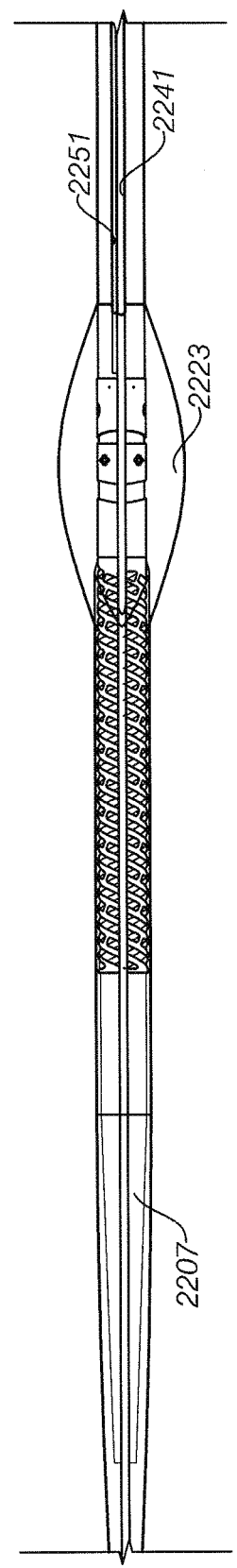
FIG. 23A
FIG. 23B

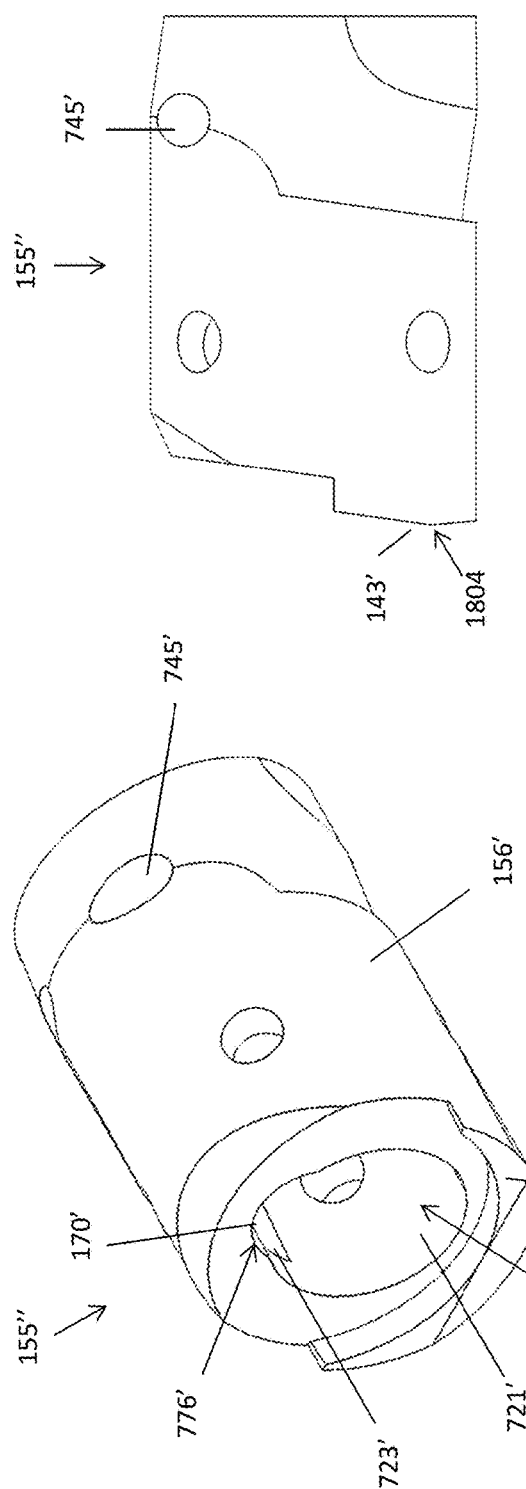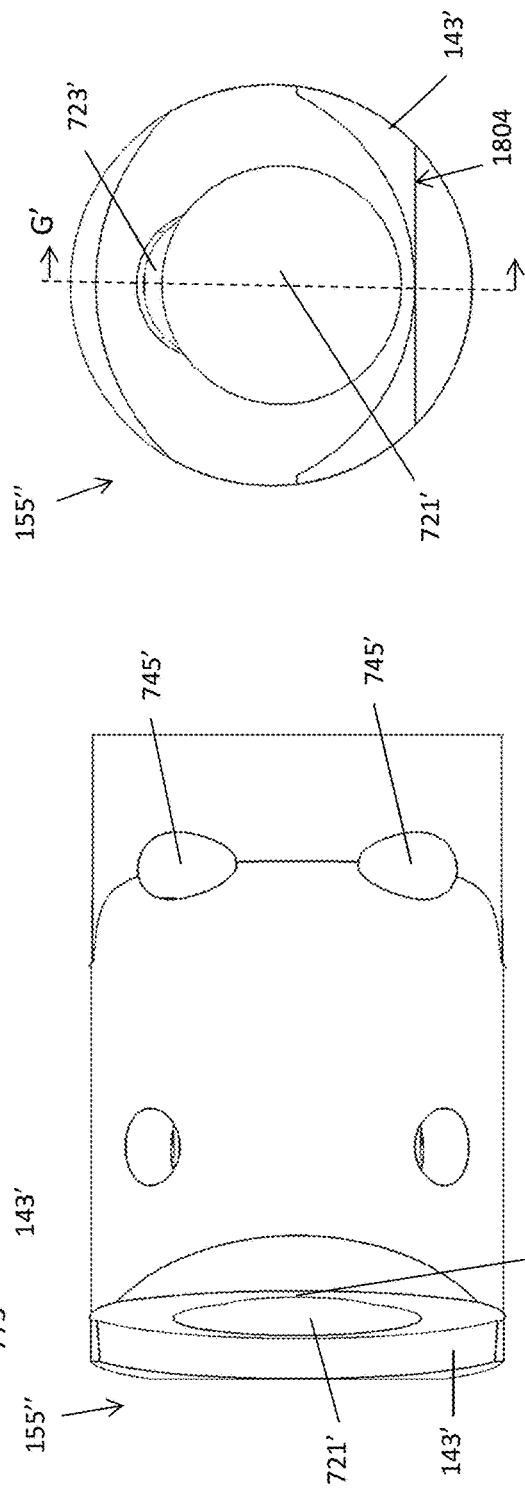

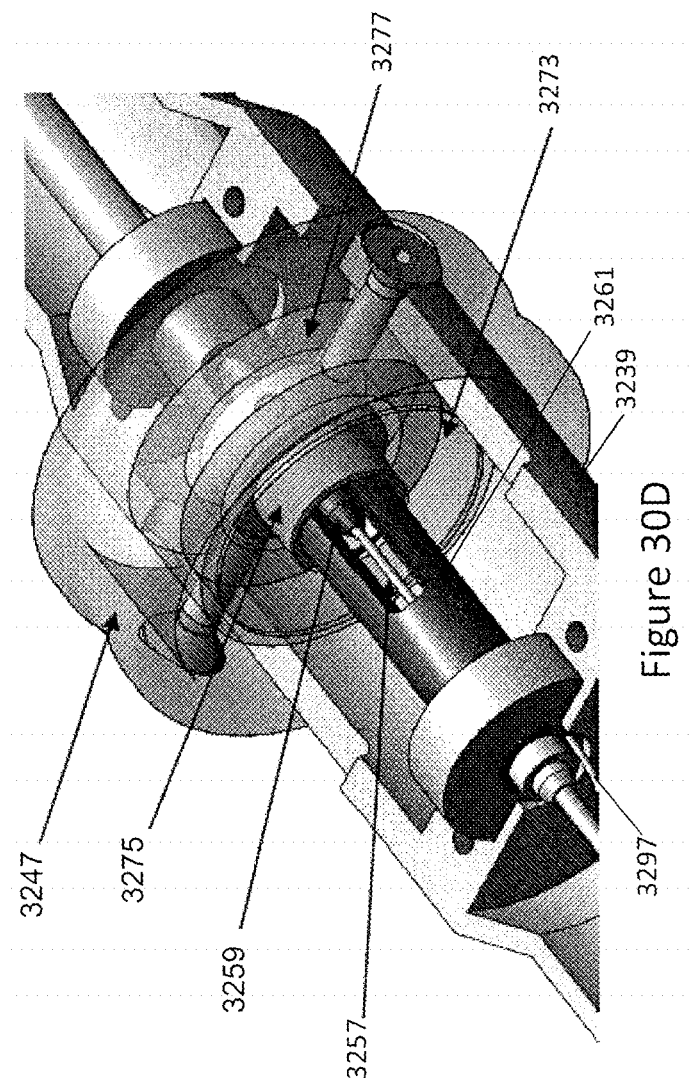

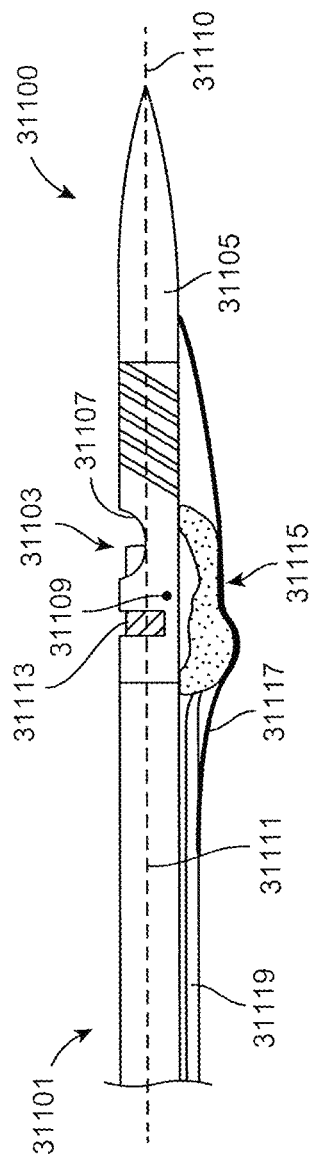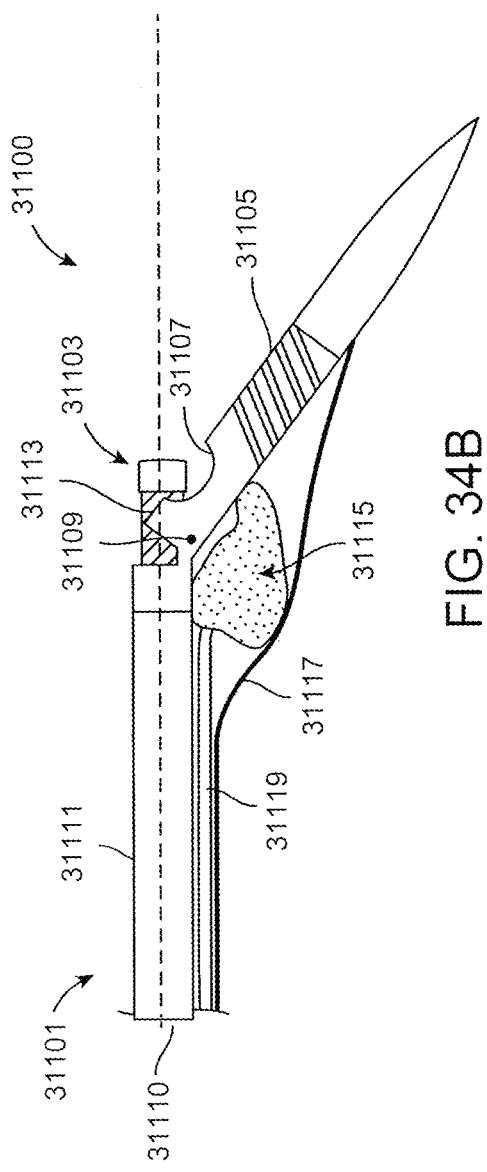

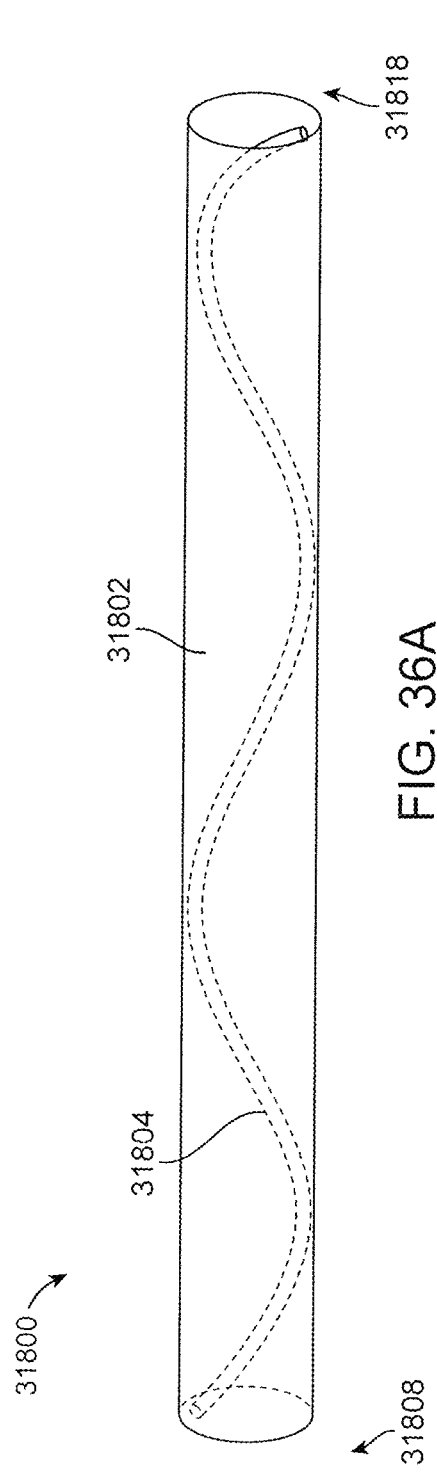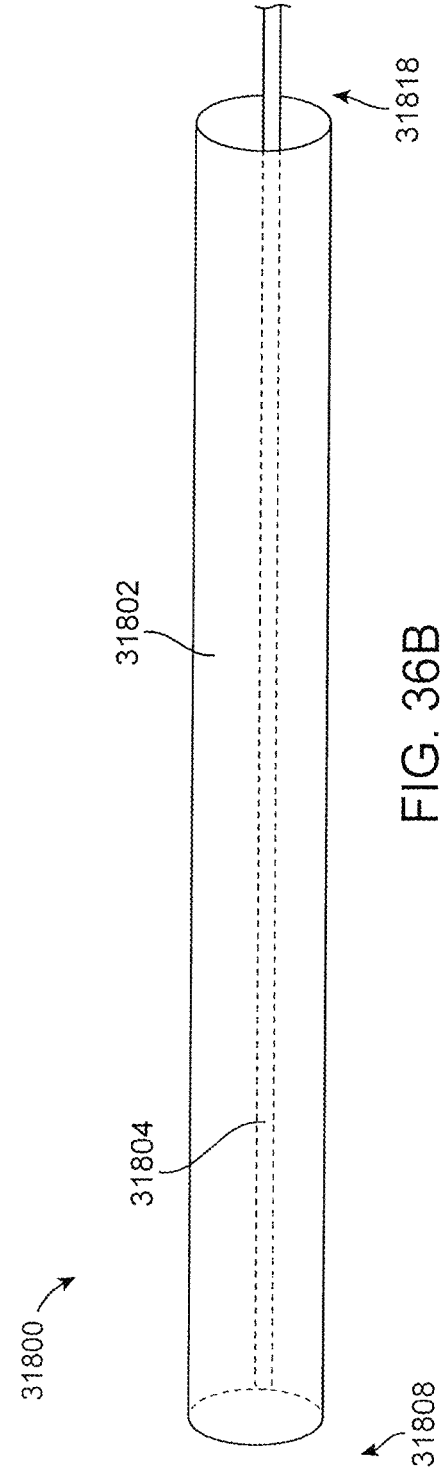

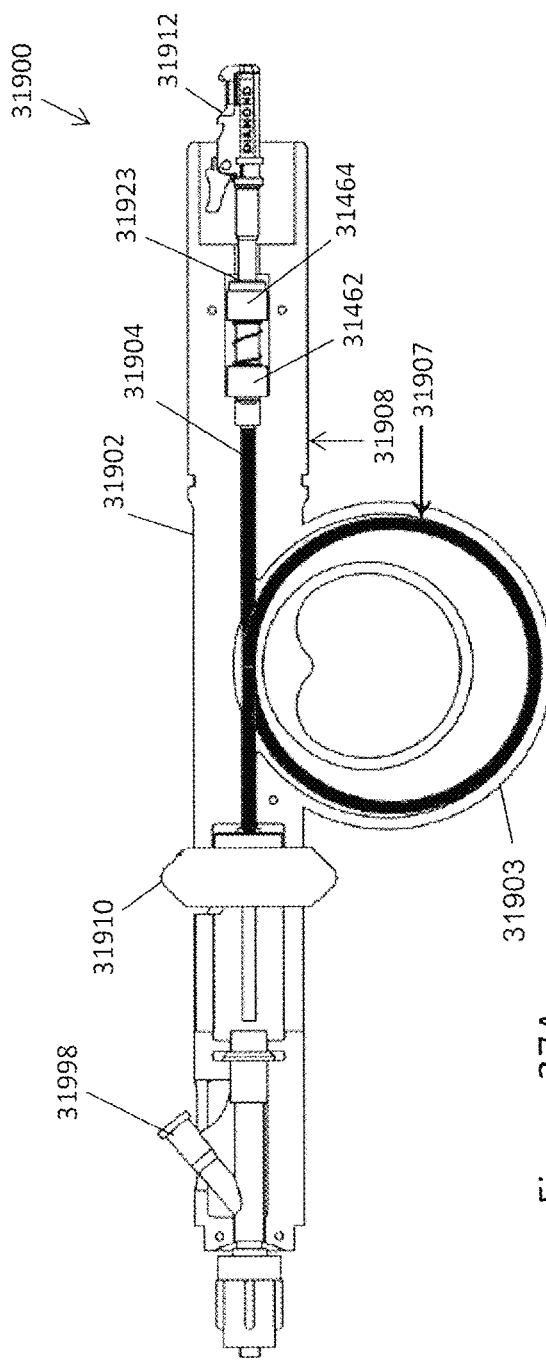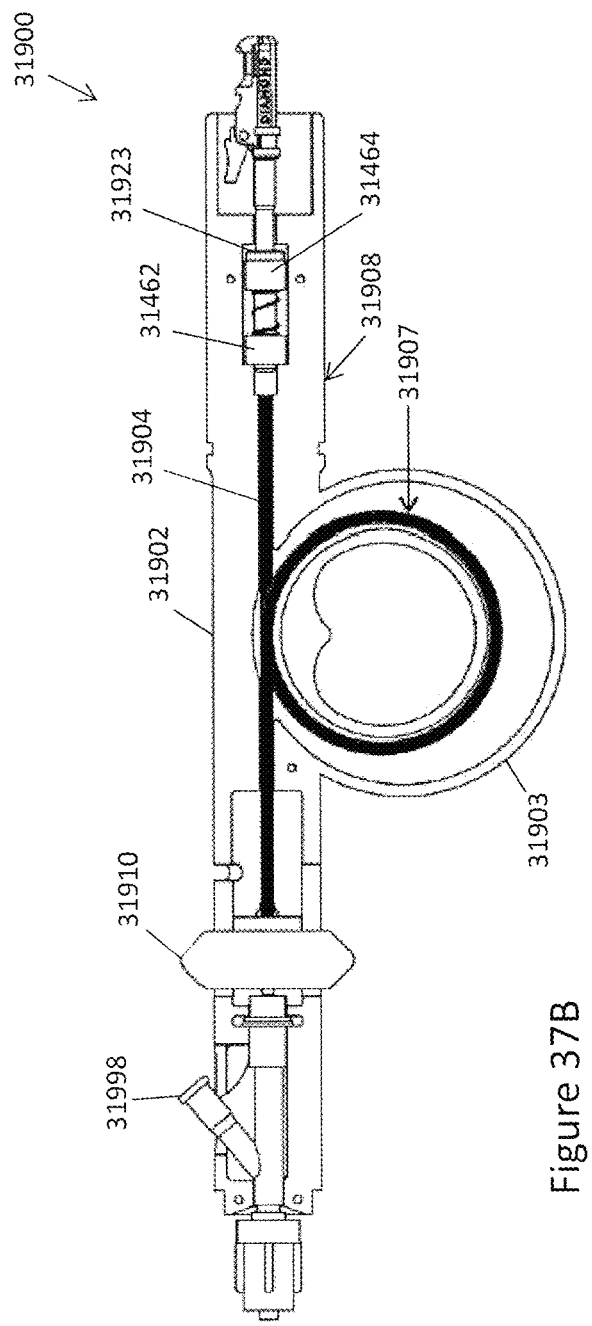
Figure 37A
Figure 37B

ATHERECTOMY CATHETERS AND OCCLUSION CROSSING DEVICES

CROSS REFERENCE TO RELATED APPLICATIONS

This application is a continuation-in-part of U.S. patent application Ser. No. 15/354,842, filed Nov. 17, 2016, titled "ATHERECTOMY CATHETERS AND OCCLUSION CROSSING DEVICES," now U.S. Pat. No. 10,470,795, which is a continuation of U.S. patent application Ser. No. 15/076,568, filed Mar. 21, 2016, titled "ATHERECTOMY CATHETERS AND OCCLUSION CROSSING DEVICES," now U.S. Pat. No. 9,498,247, which is a continuation-in-part of U.S. patent application Ser. No. 15/072,272, filed Mar. 16, 2016, titled "ATHERECTOMY CATHETERS DEVICES HAVING MULTI-CHANNEL BUSHINGS," now U.S. Pat. No. 9,592,075, which is a continuation-in-part of International Patent Application No. PCT/US2015/034613, filed Feb. 5, 2015, titled "ATHERECTOMY CATHETERS AND OCCLUSION CROSSING DEVICES", now International Publication No. WO 2015-120146, which claims priority to U.S. Provisional Patent Application No. 61/936,837, titled "ATHERECTOMY CATHETERS AND OCCLUSION CROSSING DEVICES," filed Feb. 6, 2014. Each of these applications is herein incorporated by reference in its entirety.

This application is also a continuation-in-part of U.S. patent application Ser. No. 15/457,960, filed Mar. 13, 2017, titled "ATHERECTOMY CATHETERS DEVICES HAVING MULTI-CHANNEL BUSHINGS," now U.S. Pat. No. 10,568,655, which is a continuation of U.S. patent application Ser. No. 15/072,272, filed Mar. 16, 2016, titled "ATHERECTOMY CATHETERS DEVICES HAVING MULTI-CHANNEL BUSHINGS," now U.S. Pat. No. 9,592,075, which is a continuation-in-part of International Patent Application No. PCT/US2015/034613, filed Feb. 5, 2015, titled "ATHERECTOMY CATHETERS AND OCCLUSION CROSSING DEVICES", which claims priority to U.S. Provisional Patent Application No. 61/936,837, filed Feb. 6, 2014, titled "ATHERECTOMY CATHETERS AND OCCLUSION CROSSING DEVICES," each of which is herein incorporated by reference in its entirety.

This application is also a continuation-in-part of U.S. patent application Ser. No. 14/424,277, filed Feb. 26, 2015, titled "BALLOON ATHERECTOMY CATHETERS WITH IMAGING," now U.S. Pat. No. 10,548,478, which claims priority to U.S. Provisional Patent Application No. 61/697,743, titled "BALLOON ATHERECTOMY CATHETERS WITH IMAGING," filed Sep. 6, 2012, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are atherectomy catheters and methods of using them.

BACKGROUND

Peripheral artery disease (PAD) and coronary artery disease (CAD) affect millions of people in the United States alone. PAD and CAD are silent, dangerous diseases that can have catastrophic consequences when left untreated. CAD is the leading cause of death in the United States while PAD is the leading cause of amputation in patients over 50 and is responsible for approximately 160,000 amputations in the United States each year.

Coronary artery disease (CAD) and Peripheral artery disease (PAD) are both caused by the progressive narrowing of the blood vessels most often caused by atherosclerosis, the collection of plaque or a fatty substance along the inner lining of the artery wall. Over time, this substance hardens and thickens, which can cause an occlusion in the artery, completely or partially restricting flow through the artery. Blood circulation to the arms, legs, stomach and kidneys brain and heart may be reduced, increasing the risk for stroke and heart disease.

Interventional treatments for CAD and PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Often, occlusion-crossing devices can be used to ease the passage of such devices through a blockage.

A significant body of scientific and clinical evidence supports atherectomy as a viable primary or adjunctive therapy prior to stenting for the treatment of occlusive arterial disease. Atherectomy offers a simple mechanical advantage over alternative therapies. By removing the majority of plaque mass (debulking), it creates a larger initial lumen and dramatically increases the compliance of the arterial wall. As a result, stent deployment is greatly enhanced.

Additionally, atherectomy provides several advantages related to the arterial healing response. When circumferential radial forces are applied to the vasculature, as in the case of angioplasty or stenting, the plaque mass is displaced, forcing the vessel wall to stretch dramatically. This stretch injury is a known stimulus for the cellular in-growth that leads to restenosis. By using atherectomy to remove the disease with minimal force applied to the vessel, large gains in lumen size can be created with decreased vessel wall injury and limited elastic recoiling. These effects have been shown to generate better acute results and lower restenosis rates.

Despite its advantages, atherectomy is not commonly performed due to the cost, complexity and limited applicability of available atherectomy devices. Many designs are unable to treat the wide range of disease states present in long complex lesions; luminal gain is often limited by the requirement of the physician to introduce multiple devices with increased crossing profiles; tissue collection is either unpredictable or considered unnecessary based on assumptions regarding small particle size and volumes; and optimal debulking is either not possible due to a lack of intravascular visualization or requires very long procedure times. Based on these limitations, current devices are likely to perform poorly in the coronary vasculature where safety and efficacy in de novo lesions, ostials, and bifurcations continue to pose great challenges.

In the past, atherectomy devices have focused on macerating or emulsifying the atherosclerotic plaque such that either it might be considered clinically insignificant enough to remain in the blood stream or that it can be aspirated proximally through small spaces in the catheter main body. When the plaque is not aspirated through the catheter to an external reservoir, the reliability of these devices to produce clinically insignificant embolization has been challenged. Aspiration necessitates that a vacuum be applied to a lumen or annular space within the catheter to remove emulsified tissue. In early clinical evaluations of aspiration, the presence of negative pressure at the distal working assembly caused the artery to collapse around the cutting element. This effect results in more aggressive treatment, dissections and/or perforations. In addition, options for post-procedural analysis of any removed disease are extremely limited or impossible using this methodology.

Other atherectomy devices include directional atherectomy devices, which use cup-shaped cutters that cut and "turn" the tissue distally into a storage reservoir in the distal tip of the device. This approach preserves the "as cut" nature of the plaque, but requires large distal collection elements. These large distal tip assemblies can limit the capability of the system to access small lesions and may cause additional trauma to the vessel.

Minimally invasive techniques can be enhanced through the use of on-board imaging, such as optical coherence tomography ("OCT") imaging. Images obtained from an atherectomy device, however, can be inaccurate due to the placement of the imaging sensor at a location that is far from the cutter. As a result, it can be difficult to visualize the tissue being cut. Moreover, minimally-invasive techniques can be inefficient, as often many devices are required to perform a single procedure. Moreover, currently available atherectomy devices also do not include, and are poorly adapted for use with, real time image guidance. Although intravascular diagnostic devices have consistently shown lesions that are significantly eccentric, the typical practice of physicians is to treat target lesions as if they contain concentric disease. This circumferential treatment approach virtually ensures that potentially native arterial wall and healthy vessel will be cut from the vasculature.

Further, several design challenges are presented by a single use, disposable, and single-direction imaging catheter, such as an atherectomy catheter. For example, obtaining a clear image can be difficult, as nonuniform rotational distortion ("NURD") can occur in the image as a result of the cutter vibrating or stalling as it encounters different types of tissue. Moreover, the imaging fiber, which runs from the static light source to the rotating distal tip, can become wound up as the catheter is in active (cutting) mode. Further, a motor can be required to drive the imaging assembly at the appropriate revolution rates for imaging, thereby significantly increasing the cost and complexity of the catheter.

Atherectomy catheter devices, occlusion-crossing devices, and the corresponding systems and methods that may address some of these concerns are described and illustrated below.

SUMMARY OF THE DISCLOSURE

In general, described herein are atherectomy catheters, systems including the atherectomy catheters, and methods of using the atherectomy catheters and systems. The atherectomy catheters can include on-board imaging, In particular, described herein are optical coherence tomography (OCT) catheters that may include one or more of the features illustrated, discussed and described herein in any combination. For example, described herein are catheters having a distal tip that can be deflected away from the long axis of the device at a hinge point that is offset (e.g., located on a side of the elongate body near the distal end of the elongate body). The distal tip may include a bushing that is hinged to the body and interacts with a necked region of a rotatable imaging and/or cutting assembly to displace and/or restore the distal tip. The catheter may be configured so that the distal tip is displaced by a first mechanism (e.g., a pneumatic mechanism, a pull tendon, etc.) and is restored by a second mechanism, such as the lateral motion of the imaging/cutting assembly. The device described herein may be configured so that the status of the distal tip (e.g., displacement, filling) may be detected or determined with the OCT imaging that also images the region around the perimeter of the imaging/cutting assembly of the catheter (e.g., the vessel). For example, the device may be configured so that the distal tip displacement is visible in the OCT images to provide direct feedback on the cutting status (ready to cut/not ready to cut) of the atherectomy device.

Also described herein are catheters configured to provide a mechanical advantage when driving a lateral cutting edge against the wall of a vessel that surrounds the catheter. For example, the atheterectomy device may include a pair of balloons at the distal end of the device that are separated slightly apart from each other; the first balloon that is located near the cutter pushes the cutter towards the wall of the vessel while the proximally located balloon pushes in an opposite direction, pivoting just the end region of the catheter against the wall of the vessel from the pivot point established by the second (e.g., fulcrum) balloon. As another example, the catheter can include a single C-shaped balloon configured to both urge the cutter against the wall and occlude the vessel.

Also described herein are catheters including high-powered flushing 'jets' that can be used to pack material (cut material) into the hollow nosecone, as well as to clear the imaging region. These jet flushing ports may also be configured to create a venturi effect that can be used to suck material into the nosecone and/or away from the imaging/cutting head and/or the distal end region of the elongate body.

Also described herein are techniques and structures for managing the optical fiber at the proximal end (e.g., the handle) of the catheter. In devices in which the optical fiber and drive shaft rotate and may move laterally (proximally/distally), an optical fiber management chamber at the proximal end of the device before the coupling region for coupling the optical fiber to the imaging system. The optical fiber management chamber may be cylindrical. The optical fiber management chamber typically includes a hollow space in which the fiber, as it moves laterally relative to the proximal coupling region, may safely bend. The optical fiber management chamber rotates with the optical fiber, so there is no relative rotational motion between the optical fiber management chamber and the optical fiber.

Also described herein are general occlusion crossing devices having cutting tips that may be swapped out.

In general, in one embodiment, an atherectomy catheter device includes an elongate body, a hollow distal tip, a drive shaft, a bushing, and a cutting and imaging assembly. The hollow distal tip extends from a distal end of the elongate body. The drive shaft extends distally to proximally within the elongate body. The bushing is coupled to the distal tip and has a hinge point connected to one side of the elongate body and an inner flange positioned distal to the hinge point. The cutting and imaging assembly is coupled to the drive shaft and has a distal cutting edge and a neck region that passes through the bushing. Distal movement of the drive shaft within the bushing causes the inner flange to move along the neck region of the cutting and imaging assembly, rotating the hollow distal tip and bushing about the hinge point and axially aligning the hollow distal tip with the elongate body to at least partially cover the distal cutting edge.

This and other embodiments can include one or more of the following features. The bushing can have distal end face. Proximal movement of the drive shaft within the bushing can cause a proximal surface of the cutting and imaging assembly to slide along at least a portion of the distal end face to pivot the bushing and hollow tip about the hinge point and expose the distal cutting edge. The distal end face can be angled relative to a central longitudinal axis of the elongate body. The angle can be greater than 90 degrees. The angle can be less than 90 degrees. The distal end face can be perpendicular to a central longitudinal axis of the elongate body. The bushing can further include a first channel therethrough and a second channel extending at an angle relative to the first channel. The second channel can overlap with the first channel, and the neck region can sit within the first channel when the hollow distal tip is aligned with the elongate body and through the second channel when the hollow distal tip is angled relative to the elongate body. The bushing can include a hinge channel formed through a top peripheral region of the bushing. The hinge channel can extend in a direction that is transverse to the first channel. The device can further include an optical fiber extending though the drive shaft and coupled to a reflector in the cutting and imaging assembly to form an optical coherence tomography (OCT) imaging sensor. The cutting and imaging assembly can be configured to rotate within the bushing. The cutting and imaging assembly can be configured to extend beyond the bushing and into the hollow distal tip to pack tissue into the hollow distal tip.

In general, in one embodiment, an atherectomy catheter device includes an elongate body, a hollow distal tip, a drive shaft, a bushing, and a cutting and imaging assembly. The hollow distal tip extends from a distal end of the elongate body. The drive shaft extends distally to proximally within the elongate body. The bushing is coupled to the hollow distal tip and has a hinge point connected to one side of the elongate body and a distal face that is angled at less than 90 degrees relative to a central longitudinal axis of the elongate body such that an inner distal edge is formed. The cutting and imaging assembly is coupled to the drive shaft and has a distal cutting edge and a proximal surface. Proximal movement of the drive shaft within the bushing causes the proximal surface of the cutting and imaging assembly to slide along the inner distal edge of the bushing to pivot the bushing and hollow distal tip about the hinge point to expose the distal cutting edge.

This and other embodiments can include one or more of the following features. The cutting and imaging assembly can further include a necked region configured to sit within the bushing. The bushing can further include a first channel through the bushing and a second channel extending at an angle relative to the first channel. The second channel can overlap with the first channel, and the neck region can sit within the first channel when the hollow distal tip is aligned with the elongate body and through the second channel when the hollow distal tip is angled relative to the elongate body. The bushing can include a hinge channel formed through a top peripheral region of the bushing. The hinge channel can extend in a direction that is transverse to the first elongate channel. The device can further include an optical fiber extending though the drive shaft and coupled to a reflector in the cutting and imaging assembly to form an optical coherence tomography (OCT) imaging sensor. The cutting and imaging assembly can be configured to rotate within the bushing. The cutting and imaging assembly can be configured to extend beyond the bushing and into the hollow distal tip to pack tissue into the hollow distal tip.

In general, in one embodiment, an atherectomy catheter device includes an elongate body, a hollow distal tip, a drive shaft, an optical coherence tomography fiber, and a cutting and imaging assembly. The hollow distal tip extends from a distal end of the elongate body. The drive shaft extends distally to proximally within the elongate body. The optical coherence tomography fiber runs along a central longitudinal axis of the drive shaft an entire length of the drive shaft. The cutting and imaging assembly is coupled to the drive shaft and has a distal cutting edge and a slot configured to hold a distal end of the fiber therein. The slot has a length that is equal to or greater than a radius of the cutting and imaging assembly such that the optical fiber extends from the drive shaft straight through the cutting and imaging assembly into the slot without bending.

This and other embodiments can include one or more of the following features. Proximal or distal movement of the drive shaft can cause the hollow distal tip to move off-axis of the elongate body to expose the distal cutting edge. The device can further include a reflective element positioned within the slot that can be configured to radially direct light from the optical fiber out of the elongate body. The distal end of the optical fiber can be less than 3 mm from the distal cutting edge. The optical fiber can be fixed to the slot, but otherwise be free to float within the cutting and imaging assembly and the drive shaft. The cutting and imaging assembly can be configured to rotate relative to the elongate body and the hollow distal tip. The cutting and imaging assembly can be configured to extend into the hollow distal tip to pack tissue into the hollow distal tip.

In general, in one embodiment, an atherectomy catheter device includes an elongate body, a hollow distal tip, a bushing, a cutting and imaging assembly, and a C-shaped balloon. The elongate body extends distally to proximally. The hollow distal tip extends from a distal end of the elongate body. The bushing is coupled to the hollow distal tip and is hinged at a side of the elongate body. The cutting and imaging assembly has a distal cutting edge and an imaging sensor. The C-shaped (crescent-shaped) balloon is wrapped around portions of the elongate body, hollow distal tip, and bushing, while leaving the distal cutting edge exposed. The balloon is configured to urge the distal cutting edge against a vessel wall and occlude blood flow therearound.

This and other embodiments can include one or more of the following features. The balloon can be further configured to displace the distal tip relative to the elongate body to expose the distal cutting edge. A guidewire lumen can extend within the balloon for an entire length of the balloon. The imaging sensor can be an optical coherence tomography imaging sensor. Proximal or distal movement of the drive shaft can cause the hollow distal tip to move off-axis of the elongate body about the hinge point to expose the distal cutting edge.

In general, in one embodiment, an OCT imaging atherectomy catheter device having a plurality of imaging positions includes an elongate body, a hollow distal tip, and a rotatable cutting and imaging assembly. The elongate body extends distally to proximally. The hollow distal tip extends from a distal end of the elongate body and is hinged at a side of the elongate body. The rotatable cutting and imaging assembly is coupled to a rotatable and axially moveable drive shaft that extends distally to proximally within the elongate body and has an OCT imaging sensor that is proximally adjacent to a distal cutting edge. The rotatable cutting and imaging assembly is configured to panoramically image biological tissue surrounding the catheter through the hollow distal tip when the rotatable cutting and imaging assembly is positioned at a first position that is within the hollow distal tip. The rotatable cutting and imaging assembly is further configured to image a portion of the biological tissue surrounding the catheter and a displacement of the hollow distal tip relative to the elongate body from a second position that is proximal to the first position to indicate whether the distal cutting edge is exposed.

This and other embodiments can include one or more of the following features. The catheter can further include a first imaging window and a second imaging window. An angle between the first imaging window and the second imaging window can further indicate whether the distal cutting edge is exposed. The imaging sensor can be aligned with the first and second windows when in the second position. The device can further include a third imaging window. The cutting and imaging assembly can have a third position wherein the imaging sensor is aligned with the third imaging window. The OCT imaging sensor of the rotatable cutting and imaging assembly can include an optical fiber and a reflector within the rotatable cutting and imaging assembly. The distal tip can include a bushing at a proximal end. The bushing can be hinged to the elongate body.

In general, in one embodiment, an atherectomy catheter device configured to drive a rotatable cutting assembly against a vessel wall includes a flexible elongate body, a hollow distal tip, a rotatable cutting assembly, a first balloon, and a fulcrum balloon. The hollow distal tip extends from a distal end of the elongate body and is hinged at a side of the elongate body. The rotatable cutting assembly is coupled to a rotatable and axially moveable drive shaft that extends distally to proximally within the elongate body and has a distal cutting edge. The first balloon is near the distal end region of the elongate body and is configured to drive the distal cutting edge of the rotatable cutting assembly laterally into a vessel wall by pushing against the vessel wall in a first direction. The fulcrum balloon is positioned proximally to the first balloon and is configured to expand to push against the vessel wall in a direction that is opposite the first direction. The fulcrum balloon is less than 100 cm from the first balloon.

This and other embodiments can include one or more of the following features. The device can further include an optical coherence tomography (OCT) sensor on the cutting assembly proximally adjacent to the distal cutting edge. The first balloon can be opposite a lateral opening formed in a side of the catheter between the distal tip and the elongate body. The first balloon can be opposite the distal cutting edge of the rotatable cutting assembly when the distal tip bends away from the elongate body to expose the distal cutting edge. The fulcrum balloon can be less than 75 cm from the first balloon. The fulcrum balloon can be less than 50 cm from the first balloon.

In general, in one embodiment, an atherectomy catheter device includes an elongate body, a hollow distal tip, a bushing, a cutting and imaging assembly, and a plurality of jet channels within the bushing. The hollow distal tip extends from a distal end of the elongate body. The bushing is coupled to the distal tip and hinged at a side of the elongate body. The cutting and imaging assembly is coupled to a rotatable and axially moveable drive shaft that extends distally to proximally within the elongate body and includes a distal cutting edge. The plurality of jet channels within the bushing are directed distally and coupled with a fluid line extending though the elongate body. Fluid sent through the jet channels is configured to pack tissue cut by the distal cutting edge into the hollow distal tip.

This and other embodiments can include one or more of the following features. The plurality of jet channels can include two channels extending along an inner circumference of the bushing. The jet channels can be positioned to create a venturi effect at the distal end of the cutting and imaging assembly.

In general, in one embodiment, an atherectomy device includes an elongate body, a distal tip, a rotatable cutting and imaging assembly, an optical fiber, and a handle attached to the elongate body. The distal tip extends from a distal end of the elongate body and is hinged at a side of the elongate body. The rotatable cutting and imaging assembly is coupled to a rotatable and axially movable drive shaft that extends distally to proximally within the elongate body. The cutting and imaging assembly has an OCT imaging sensor. The optical fiber extends from the OCT imaging sensor and proximally through the drive shaft. The handle attached to the elongate body includes a cylindrical fiber holding chamber and an optical fiber coupling region. The cylindrical fiber holding chamber is at the proximal end of the catheter and is configured to rotate with the drive shaft and optical fiber. The fiber holding chamber has an inner region into which the optical fiber extends. The optical fiber coupling region is configured to couple the optical fiber to a light source. The optical fiber and drive shaft are configured to move axially within the handle relative to the cylindrical fiber holding chamber and optical fiber coupling region. The optical fiber is configured to bend within the fiber holding chamber as the optical fiber and drive shaft move axially.

This and other embodiments can include one or more of the following features. The handle can further include a driveshaft tensioning spring configured such that, when the driveshaft is moved proximally, the spring can compress to apply a controlled tensile load on the driveshaft. The elongate body can further include a balloon connected thereto and a balloon inflation lumen extending along the elongate body. The handle can include an inflation chamber therein configured to connect to the balloon inflation lumen. The elongate body can be configured to rotate independently of the balloon inflation chamber.

In particular, described herein are atherectomy catheter devices including a C-shaped (apposition) balloon and a second (occluding) balloon. In some variations only the C-shaped balloon is included. For example, described herein are atherectomy catheter devices including: an elongate body extending distally to proximally along a longitudinal axis; a nosecone extending from a distal end of the elongate body, wherein the nosecone is hinged to the elongate body at a hinge region on first lateral side of the device; a cutting assembly having a distal cutting edge; a cutting window on the first lateral side of the device at a proximal end of the nosecone through which the distal cutting edge may be exposed; a first balloon configured to urge the distal cutting edge against a vessel wall, wherein the first balloon is coupled proximally of the hinge region on the elongate body and coupled distally of the cutting window on the nosecone, so that the first balloon does not extend over the cutting window; wherein the first balloon, when inflated, has a C-shaped cross-sectional profile and a radius of curvature that is larger than a radius of curvature of the cutting assembly; and a second balloon on the elongate body proximal to the first balloon and configured to occlude blood flow through the vessel.

The nosecone may be referred to herein as a distal tip region, and may be hollow, substantially hollow (e.g., along >50% of its length, >60% of its length, >70% of its length, etc.) or it may not be hollow. The nosecone is typically hinged or otherwise deflectable out of the longitudinal axis of the elongate body to expose the cutting edge of the cutter so that the device can cut the side of a vessel. As mentioned, the nosecone may be hinged, e.g., to the elongate body, at a hinge region on first lateral side of the device. The hinge region may be a hinge point or a hinge pin that extends through a laterally offset side of the elongate body. The hinge region is a hinge point on the first lateral side of the elongate body.

The nosecone may be a single piece or it may be formed of multiple, connected, pieces. For example, the nosecone may be connected via a bushing, as described in greater detail herein, and the bushing hinged to the elongate body.

The first balloon may span the hinge region. For example, as mentioned above, the first balloon may be attached to a region that is proximal to the hinge region (on the elongate body) and distal to the hinge region (on the nosecone). The first balloon may also be oriented so that it expands (e.g., pushing) just one side of the catheter device (the side opposite the hinge region and/or the cutting window) to both drive the cutter against the wall of a vessel and to help displace the nosecone and expose the cutting edge of the cutter.

For example, the cutting assembly may be a cutting and imaging assembly, and may include an imaging sensor thereon. Any appropriate imaging sensor (e.g., ultrasound, optical, and in particular OCT) imaging sensor may be used. When an OCT imaging sensor is used the OCT imaging sensor may include a mirror (reflector) and an interface with the end of a fiber optic. The imaging sensor may rotate with the cutter.

In general, the first balloon has a C-shaped cross-section (when taken transverse to the elongate longitudinal axis of the device, particularly near the proximal and distal ends of the balloon). In general, the first balloon has a tapered distal end and a tapered proximal end. The C-shaped balloons described herein may also be referred to as having a C-shape (crescent shape), and may have a crescent-shaped profile over at least a part of their length. This shape results in a radially-asymmetric expansion of the first balloon that drives the cutter window and/or cutter against the vessel wall. For example, the first balloon may be coupled proximally of the hinge region on the elongate body by wrapping around half (e.g., 50%) or more (e.g., 60%, 70%, 75%, 80%, 85%, 90%, etc.) of the circumference of the elongate body. The first balloon may be coupled distally of the cutting window on the nosecone by wrapping around half (e.g., 50%) or more (e.g., 60%, 70%, 75%, 80%, 85%, 90%, etc.) of the circumference of the nosecone. As mentioned, the first balloon may displace the nosecone relative to the elongate body to expose the distal cutting edge when inflated.

In general, the first balloon and the second balloon may be connected a single inflation lumen, and may be configured to be inflated with gas (e.g., $CO_2$, air, etc.), liquid (saline, etc.) or the like. It may be particularly beneficial to inflate with a gas as this may enhance the compliance. The first and/or second balloon may be inflated with an inflation pressure of less than 5 psi. The first and second balloons may have different compliances. For example, the second balloon may be more compliant than the first balloon; alternatively the first balloon may be more compliant than the second balloon. In some variations it may be beneficial for the second balloon to be more compliant than the first balloon, as it may inflate first even when sharing an inflation lumen; the disparity in compliance may also allow the first balloon to be driven against the vessel wall more effectively.

Any of these apparatuses (device and systems) may include a guidewire lumen extending within the first (and second) balloon for an entire longitudinal length of the first balloon. Thus, the guidewire may pass between the body of the atherectomy catheter and the balloon(s).

In general, the atherectomy catheters described herein may open and/or close the nosecone to expose or cover the cutting edge (distal-facing cutting edge) of a cutter by pulling proximally and pushing distally on the cutter assembly (cutting and imaging assembly or just cutting assembly). A drive shaft may be coupled to the cutting and imaging assembly and may be pulled (or in some variations pushed) to to cause the nosecone to move off-axis relative to the elongate body about the hinge region to expose the distal cutting edge through the cutting window. As mentioned, displacing the tip by pulling the drive shaft may be assisted by inflation/deflation of the C-shaped balloon.

In general the second balloon is proximal to the first balloon and is an occluding balloon which may help occlude blood flow through the vessel when inflated. The second balloon may extend circumferentially around elongate body. For example, the second balloon may be configured to block the flow of blood, which may prevent interference in imaging and/or cutting. The first (C-shaped) balloon and the second balloon may be spaced apart to optimize the occlusive ability of the second (occlusion) balloon and the displacement of the distal nosecone and apposition of the cutter to the vessel by the first (apposition) balloon. For example, the second balloon may be less than 100 cm (e.g., less than 90 cm, less than 85 cm, less than 80 cm, less than 75 cm, less than 70 cm, etc.) from the first balloon and/or between 10 cm and 100 cm (e.g., between 10 cm and 80 cm, between 10 cm and 75 cm, between 20 cm and 80 cm, between 20 cm and 75 cm, between 30 cm and 75 cm, between 40 cm and 75 cm, between 50 cm and 75 cm, etc.).

The first (C-shaped) balloon may be centered to optimize its ability to drive the cutter against the vessel wall. For example, the longitudinal center of the balloon may be positioned opposite the cutting window (or cutter, when extended). The diameter of the C-shaped balloon, when inflated/expanded, may be between about 0.5 and 5× (e.g., between 1× and 5×, between 2× and 5×, between 3× and 5×, etc.) the diameter of the nosecone and/or distal end of the elongate body of the catheter. For example, the first balloon may be configured to have an expanded diameter of between 2 mm and 6 mm.

For example, described herein are atherectomy catheter devices including: an elongate body extending distally to proximally along a longitudinal axis; a nosecone extending from a distal end of the elongate body, wherein the nosecone is hinged at a hinge region to the elongate body on a first lateral side of the elongate body; a cutting and imaging assembly having an imaging sensor thereon and a distal cutting edge; a first balloon configured to urge the distal cutting edge against a vessel wall, wherein the first balloon is coupled to the elongate body at a proximal end and to the nosecone at a distal end, wherein the first balloon, when inflated, has a C-shaped profile and a radius of curvature that is larger than a radius of curvature of the cutting and imaging assembly; and a second balloon distal to the first balloon and configured to occlude blood flow through the vessel, wherein the second balloon is more compliant than the first balloon.

For example, an atherectomy catheter device may include: an elongate body extending distally to proximally along a longitudinal axis; a hollow nosecone extending from a distal end of the elongate body, wherein the nosecone is hinged at a hinge region to the elongate body on a first lateral side of the elongate body; a cutting and imaging assembly having an optical coherence tomography (OCT) imaging sensor thereon and a distal cutting edge; a cutting window on the first lateral side at a proximal end of the nosecone through which the distal cutting edge may be exposed; a first balloon configured to urge the distal cutting edge against a vessel wall, wherein the first balloon is coupled proximally of the hinge region on the elongate body by wrapping around half or more of the circumference of the elongate body, and coupled distally of the cutting window on the hollow nosecone by wrapping around half or more of the circumference of the nosecone, so that the first balloon does not extend over the cutting window; wherein the first balloon, when inflated, has a C-shaped cross-sectional profile perpendicular to the longitudinal axis and a radius of curvature that is larger than a radius of curvature of the cutting and imaging assembly; and a second balloon proximal to the first balloon and configured to occlude blood flow through the vessel.

In general, in one embodiment, a method of performing atherectomy includes: (1) inserting an atherectomy device into a blood vessel, the atherectomy device comprising an elongate body, a cutter, and a C-shaped (e.g., crescent-shaped) balloon; (2) inflating the C-shaped balloon to urge the cutter against a wall of the blood vessel; and (3) while the balloon is inflated, simultaneously rotating the cutter and translating the atherectomy device distally to remove plaque from the wall of the blood vessel.

This and other embodiments can include one or more of the following features. The device can further include a driveshaft extending through the elongate body and attached to the cutter, and a hollow distal tip extending from a distal end of the elongate body and hinged at a side hinge point of the elongate body. The method can further include translating the driveshaft to deflect the hollow distal tip at the hinge point to expose the cutter. The balloon can extend over the hinge point and can be wrapped around substantially all of the circumference of the catheter device except at a cutting window of the device such that the distal cutting edge is exposed. The method can further include imaging the blood vessel with an imaging sensor attached to the cutter. The imaging sensor can be an optical coherence tomography imaging sensor. Inflating the balloon can further occlude blood flow through the blood vessel. Inflating the balloon can further include inflating to a pressure of less than 5 psi. The balloon can be compliant. The balloon can have a tapered distal end and a tapered proximal end. A center of the balloon can be substantially opposite to the distal cutting edge. Inflating the balloon can include inflating to an expanded diameter of between 2 mm and 6 mm.

Also described herein are atherectomy catheter devices having a multi-channeled bushings. Any of these atherectomy catheter devices may include: an elongate body; a tip extending from a distal end of the elongate body; a drive shaft extending within the elongate body; a bushing comprising a bushing body, a hinge point on a side of the bushing body, a first channel extending proximally to distally through the bushing body, a second channel extending proximally to distally through the bushing body, overlapping with the first channel and having a diameter of the second channel that is less than a diameter of the first channel, and wherein the second channel is angled between 1° and 45° relative to the first channel, a first opening at a distal end of the bushing body into the first channel, and a second opening at the distal end of the bushing body into the second channel, wherein the first and second openings overlap; and a cutter having a distal cutting head with a cutting edge, an elongate cylindrical body, and a neck region extending between the distal cutting edge and the elongate cylindrical body, wherein the drive shaft is coupled to the elongate cylindrical body; further wherein distal movement of the drive shaft extends the cylindrical body of the cutter within the first channel of the bushing and drives the tip about the hinge point to axially align the tip with the elongate body and at least partially cover the cutting edge, while proximal movement of the drive shaft extends the neck region of the cutter within the second channel of the bushing and drives the tip about the hinge point to angle the tip relative to the elongate body and at least partially expose the cutting edge.

Any of these bushings may also or alternatively comprise an inner flange positioned distal to the hinge, wherein distal movement of the drive shaft extends the cylindrical body of the cutter within the first channel of the bushing and drives the neck region against the inner flange portion to drive the tip about the hinge point to axially align the tip with the elongate body. The inner flange may include a face that is angled relative to the long axis of the elongate body. For example the inner flange may be angled at an angle of between about 2° (degrees) and about 90° (e.g., between about 5° and about 45°, between about 5° and 30°, etc.).

Any of these devices may include outer flange at the distal end of the bushing, wherein proximal movement of the drive shaft extends the neck region of the cutter within the second channel of the bushing and drives the distal cutting head against the outer flange portion to drive the tip about the hinge point to angle the tip relative to the elongate body. The outer flange may include a face that is angled relative to the long axis of the elongate body. For example, the outer flange may be angled at an angle of between about 2° and about 90° (e.g., between about 5° and about 45°, between about 5° and about 30°, etc.).

In any of these devices, the second channel may be angled relative to the first channel between about 2° and 45°, between about 2° and 30°, between about 2° and 20°, etc.

In any of these devices, the hinge point may be one of a pair of hinge points that are on either side of the bushing body and offset from a midline along a distal-to-proximal axis of the bushing body. The hinge point or hinge points may be part of a hinge channel formed through a top peripheral region of the bushing body, further wherein the hinge channel extends in a direction that is transverse to the first channel. The hinge point is generally located toward the proximal end of the bushing and may be positioned longitudinally along the proximal-to-distal axis of the bushing within the proximal 40%, 30%, 20%, 10% of the proximal end of the bushing.

Any of the apparatuses (e.g., catheter devices, atherectomy devices, etc.) described herein may be configured to provide imaging, including optical coherence tomography imaging. For example, and of these apparatuses may include an optical fiber extending though the drive shaft and coupled to a reflector in the cutter to form an optical coherence tomography (OCT) imaging sensor.

In general the cutter (which may also be referred to as a cutting assembly and/or cutting an imaging assembly) may be configured to rotate within the bushing. For example, the elongate cylindrical body of the cutter may be configured to rotate within the bushing.

The tip of any of these devices may be a hollow tip and may be configured for packing cut tissue (e.g., in conjunction with the cutter). For example, the cutter may be configured to extend beyond the bushing and into the tip to pack tissue into the tip.

An atherectomy catheter device having a multi-channeled bushing may include: an elongate body; a tip extending from a distal end of the elongate body; a drive shaft extending within the elongate body; a bushing comprising a bushing body, a pair of hinge points on either side of the bushing body that are offset from a midline along a distal-to-proximal axis of the bushing body, an inner flange positioned distal to the hinge points, a first channel extending proximally to distally through the bushing body, a second channel extending proximally to distally through the bushing body and having a diameter along a length of the second channel that is less than a diameter along a length of the first channel, and wherein the first and the second channels overlap, and wherein the second channel is angled between 1° and 45° relative to the first channel, a first opening at a distal end of the bushing body into the first channel, and a second opening at a distal end of the bushing body into the second channel, wherein the first and second openings overlap, and an outer flange portion distal to the inner flange portion; and a cutter having a distal cutting head with a cutting edge, an elongate cylindrical body, and a neck region extending between the distal cutting edge and the elongate cylindrical body, wherein the drive shaft is coupled to the elongate cylindrical body; further wherein distal movement of the drive shaft extends the cylindrical body of the cutter within the first channel of the bushing, drives the neck region against the inner flange portion and drives the tip about the hinge points to axially align the tip with the elongate body at least partially covering the cutting edge, while proximal movement of the drive shaft extends the neck region of the cutter within the second channel of the bushing, drives the distal cutting head against the outer flange portion, and drives the tip about the hinge points to angle the tip relative to the elongate body and at least partially expose the cutting edge.

An atherectomy catheter device having a multi-channeled bushing may include: an elongate body; a hollow distal tip extending from a distal end of the elongate body; a drive shaft extending within the elongate body; a bushing comprising a bushing body, a pair of hinge points on either side of the bushing body that are offset from a midline along a distal-to-proximal axis of the bushing body, an inner flange positioned distal to the hinge points a first channel extending proximally to distally through the bushing body, a second channel extending proximally to distally through the bushing body and having a diameter along a length of the second channel that is less than a diameter along a length of the first channel, and wherein the first and the second channels overlap, and wherein the second channel is angled between 1° and 45° relative to the first channel, a first opening at a distal end of the bushing body into the first channel, and a second opening at a distal end of the bushing body into the second channel, wherein the first and second openings overlap, and an outer flange portion distal to the inner flange portion; a cutter having a distal cutting head with a cutting edge, an elongate cylindrical body, and a neck region extending between the distal cutting edge and the elongate cylindrical body, wherein the drive shaft is coupled to the elongate cylindrical body; further wherein distal movement of the drive shaft extends the cylindrical body of the cutter within the first channel of the bushing and drives the hollow distal tip about the hinge points to axially align the hollow distal tip with the elongate body at least partially covering the cutting edge, while proximal movement of the drive shaft extends the neck region of the cutter within the second channel of the bushing and drives the hollow distal tip about the hinge points to angle the hollow distal tip relative to the elongate body and at least partially expose the cutting edge.

Also described herein are atherectomy catheter devices having a multi-channeled bushings. Any of these atherectomy catheter devices may include: an elongate body; a tip extending from a distal end of the elongate body; a drive shaft extending within the elongate body; a bushing comprising a bushing body, a hinge point on a side of the bushing body, a first channel extending proximally to distally through the bushing body, a second channel extending proximally to distally through the bushing body, overlapping with the first channel and having a diameter of the second channel that is less than a diameter of the first channel, and wherein the second channel is angled between 1° and 45° relative to the first channel, a first opening at a distal end of the bushing body into the first channel, and a second opening at the distal end of the bushing body into the second channel, wherein the first and second openings overlap; and a cutter having a distal cutting head with a cutting edge, an elongate cylindrical body, and a neck region extending between the distal cutting edge and the elongate cylindrical body, wherein the drive shaft is coupled to the elongate cylindrical body; further wherein distal movement of the drive shaft extends the cylindrical body of the cutter within the first channel of the bushing and drives the tip about the hinge point to axially align the tip with the elongate body and at least partially cover the cutting edge, while proximal movement of the drive shaft extends the neck region of the cutter within the second channel of the bushing and drives the tip about the hinge point to angle the tip relative to the elongate body and at least partially expose the cutting edge.

Any of these bushings may also or alternatively comprise an inner flange positioned distal to the hinge, wherein distal movement of the drive shaft extends the cylindrical body of the cutter within the first channel of the bushing and drives the neck region against the inner flange portion to drive the tip about the hinge point to axially align the tip with the elongate body. The inner flange may include a face that is angled relative to the long axis of the elongate body. For example the inner flange may be angled at an angle of between about 2° (degrees) and about 90° (e.g., between about 5° and about 45°, between about 5° and 30°, etc.).

Any of these devices may include outer flange at the distal end of the bushing, wherein proximal movement of the drive shaft extends the neck region of the cutter within the second channel of the bushing and drives the distal cutting head against the outer flange portion to drive the tip about the hinge point to angle the tip relative to the elongate body. The outer flange may include a face that is angled relative to the long axis of the elongate body. For example, the outer flange may be angled at an angle of between about 2° and about 90° (e.g., between about 5° and about 45°, between about 5° and about 30°, etc.).

In any of these devices, the second channel may be angled relative to the first channel between about 2° and 45°, between about 2° and 30°, between about 2° and 20°, etc.

In any of these devices, the hinge point may be one of a pair of hinge points that are on either side of the bushing body and offset from a midline along a distal-to-proximal axis of the bushing body. The hinge point or hinge points may be part of a hinge channel formed through a top peripheral region of the bushing body, further wherein the hinge channel extends in a direction that is transverse to the first channel. The hinge point is generally located toward the proximal end of the bushing and may be positioned longitudinally along the proximal-to-distal axis of the bushing within the proximal 40%, 30%, 20%, 10% of the proximal end of the bushing.

Any of the apparatuses (e.g., catheter devices, atherectomy devices, etc.) described herein may be configured to provide imaging, including optical coherence tomography imaging. For example, and of these apparatuses may include an optical fiber extending though the drive shaft and coupled to a reflector in the cutter to form an optical coherence tomography (OCT) imaging sensor.

In general the cutter (which may also be referred to as a cutting assembly and/or cutting an imaging assembly) may be configured to rotate within the bushing. For example, the elongate cylindrical body of the cutter may be configured to rotate within the bushing.

The tip of any of these devices may be a hollow tip and may be configured for packing cut tissue (e.g., in conjunction with the cutter). For example, the cutter may be configured to extend beyond the bushing and into the tip to pack tissue into the tip.

An atherectomy catheter device having a multi-channeled bushing may include: an elongate body; a tip extending from a distal end of the elongate body; a drive shaft extending within the elongate body; a bushing comprising a bushing body, a pair of hinge points on either side of the bushing body that are offset from a midline along a distal-to-proximal axis of the bushing body, an inner flange positioned distal to the hinge points, a first channel extending proximally to distally through the bushing body, a second channel extending proximally to distally through the bushing body and having a diameter along a length of the second channel that is less than a diameter along a length of the first channel, and wherein the first and the second channels overlap, and wherein the second channel is angled between 1° and 45° relative to the first channel, a first opening at a distal end of the bushing body into the first channel, and a second opening at a distal end of the bushing body into the second channel, wherein the first and second openings overlap, and an outer flange portion distal to the inner flange portion; and a cutter having a distal cutting head with a cutting edge, an elongate cylindrical body, and a neck region extending between the distal cutting edge and the elongate cylindrical body, wherein the drive shaft is coupled to the elongate cylindrical body; further wherein distal movement of the drive shaft extends the cylindrical body of the cutter within the first channel of the bushing, drives the neck region against the inner flange portion and drives the tip about the hinge points to axially align the tip with the elongate body at least partially covering the cutting edge, while proximal movement of the drive shaft extends the neck region of the cutter within the second channel of the bushing, drives the distal cutting head against the outer flange portion, and drives the tip about the hinge points to angle the tip relative to the elongate body and at least partially expose the cutting edge.

An atherectomy catheter device having a multi-channeled bushing may include: an elongate body; a hollow distal tip extending from a distal end of the elongate body; a drive shaft extending within the elongate body; a bushing comprising a bushing body, a pair of hinge points on either side of the bushing body that are offset from a midline along a distal-to-proximal axis of the bushing body, an inner flange positioned distal to the hinge points a first channel extending proximally to distally through the bushing body, a second channel extending proximally to distally through the bushing body and having a diameter along a length of the second channel that is less than a diameter along a length of the first channel, and wherein the first and the second channels overlap, and wherein the second channel is angled between 1° and 45° relative to the first channel, a first opening at a distal end of the bushing body into the first channel, and a second opening at a distal end of the bushing body into the second channel, wherein the first and second openings overlap, and an outer flange portion distal to the inner flange portion; a cutter having a distal cutting head with a cutting edge, an elongate cylindrical body, and a neck region extending between the distal cutting edge and the elongate cylindrical body, wherein the drive shaft is coupled to the elongate cylindrical body; further wherein distal movement of the drive shaft extends the cylindrical body of the cutter within the first channel of the bushing and drives the hollow distal tip about the hinge points to axially align the hollow distal tip with the elongate body at least partially covering the cutting edge, while proximal movement of the drive shaft extends the neck region of the cutter within the second channel of the bushing and drives the hollow distal tip about the hinge points to angle the hollow distal tip relative to the elongate body and at least partially expose the cutting edge.

In general, in one embodiment, an atherectomy catheter includes an elongate flexible catheter body, a cutter near the distal end of the catheter body, a drive shaft connected to the cutter and extending within the catheter body, an imaging element near the distal end of the catheter body and an imaging shaft connected to the imaging element and extending within the catheter body. The cutter and the imaging element are mechanically isolated, and the drive shaft is configured to be axially translated relative to the imaging shaft and the catheter body.

This and other embodiments can include one or more of the following features. The drive shaft and imaging shaft can be decoupled along the length of the catheter body. The drive shaft and imaging shaft can be coupled at a proximal end of the device. The atherectomy catheter can include a handle configured to transmit torque simultaneously to the proximal end of the drive shaft and the imaging shaft, and the drive shaft and imaging shaft can be coupled within the handle. The handle can include a translation mechanism configured to translate the drive shaft without translating the imaging shaft. The atherectomy catheter can include an inflatable element configured to urge the cutter against a vessel wall. The atherectomy catheter can include an elongate distal tip connected to the catheter body, and the elongate distal tip can include a cutting window therein, the cutting window sized and dimensioned so as to cause tissue to invaginate within the cutting window. The imaging element can include an optical fiber, and the optical fiber can be coupled to the imaging shaft only at a distal end of the imaging shaft. The imaging element can include an optical coherence tomography imaging element. The drive shaft and imaging shaft can be concentric, and the drive shaft can extend within the imaging shaft. The drive shaft and the imaging shaft both can extend substantially along a central axis of the catheter body. The imaging element can include an optical fiber, and the optical fiber can extend off-axis along the length of the catheter body. The optical fiber can be configured to rotate within the imaging shaft without wrapping around the drive shaft. The drive shaft and imaging shaft can be parallel. The imaging shaft can extend off-axis relative to the elongate body. The drive shaft can extend on-axis relative to the elongate body. The atherectomy catheter can include a handle configured to transmit torque simultaneously to the proximal end of the drive shaft and the imaging shaft. The handle further can include a rotation knob configured to allow rotation of the elongate body up to three rotations. The knob can include a rotation limiter, the rotation limiter can be configured to allow rotation of up to a set amount between one and three rotations while not lengthening the elongate body. The drive shaft and imaging shaft can be concentric, and the imaging shaft can extend within the drive shaft. A distal end of the drive shaft can include a clear annular portion connected to the cutter. The imaging element can be configured to be axially aligned with the clear annular portion for imaging. The clear annular portion can include sapphire, polycarbonate, glass, or acrylic.

In general, in one embodiment, an atherectomy catheter includes an elongate flexible catheter body. The atherectomy catheter includes a drive shaft extending within the catheter body, the drive shaft having a cutter attached thereto. The atherectomy catheter includes an elongate distal tip connected to the catheter body at a hinge point. The atherectomy catheter includes an inflatable body linked to the elongate flexible catheter body and to the elongate distal tip such that inflation of the inflatable body axially deflects the elongate distal tip away from the elongate flexible catheter body at the hinge point to expose the cutter. The inflatable body is linked to the elongated flexible catheter body and the elongated distal tip with a sling extending along an outer surface of the balloon and attached to the elongated flexible catheter body and the elongate distal tip.

This and other embodiments can include one or more of the following features. The atherectomy catheter can include a biasing mechanism configured to return the elongate distal tip to a position approximately axially aligned with the catheter body. The biasing mechanism can include a wedge activated by placing axial force on the drive shaft. The elongate distal tip can include a cutting window therein, and the cutting window can have an asymmetric shape configured to prevent the cutter from hitting a distal edge of the cutting window. The atherectomy catheter can include an imaging element attached to the cutter and configured to rotate therewith. The imaging element can be an optical coherence tomography imaging element. The imaging element can include an optical fiber, and the optical fiber can extend through the drive shaft substantially on-axis with the catheter body.

In general, in one embodiment, an atherectomy assembly includes an elongate flexible catheter body. The atherectomy assembly includes a drive shaft extending within the catheter body. The drive shaft has a rotatable cutter attached thereto and is axially movable with respect to the elongate flexible catheter body. The atherectomy assembly includes an optical fiber attached to the cutter and configured to rotate therewith. The atherectomy assembly includes a handle having a distal end attached to the elongate body and a proximal end configured to connect the optical fiber to a light source. The handle is configured such the optical fiber is axially movable with respect to the distal end and axially fixed with respect to the proximal end.

This and other embodiments can include one or more of the following features. The handle can include a tube within which the optical fiber can reside. The optical fiber can be configured to wind within the tube. The tube can be shaped as a ring, and the optical fiber can be configured to conform to an outer perimeter of the tube when in a compressed configuration and to conform to an inner perimeter of the tube when in an extended configuration. The optical fiber can be configured to transmit an optical coherence tomography signal.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4B, 4C and 4D each show the catheter of FIG. 4A with various components removed to allow description of internal parts.

FIGS. 5A-5G illustrate exemplary embodiments of a handle for an atherectomy catheter.

FIG. 8A shows a panoramic OCT image of a blood vessel through the nosecone of an atherectomy catheter, as identified by the arrow in FIG. 8B.

FIG. 9A shows a panoramic OCT image of a blood vessel taken with an atherectomy catheter through the cutting window(s) when the nosecone is closed and the cutter is in a passive position, as identified by the arrow in FIG. 9B.

FIGS. 11A and 11B show another embodiment of an atherectomy catheter having a cutter engaging distal surface that is normal to the longitudinal axis of the catheter. FIG. 11A shows a cross-section of the catheter while FIG. 11B shows a side view of the bushing.

FIGS. 12A and 12B show another embodiment of an atherectomy catheter having a cutter engaging distal surface that is at an angle relative to the longitudinal axis so as to provide only a point of contact with the distal surface of the cutter. FIG. 12A shows a cross-section of the catheter. FIG. 12B shows a side view of the bushing.

FIGS. 18A-18C show an embodiment of an atherectomy catheter having an eccentric distal balloon and a concentric proximal balloon.

FIGS. 20A and 20B show an embodiment of an atherectomy catheter having a distal jog and a proximal eccentric balloon.

FIGS. 23A and 23B show an embodiment of an atherectomy catheter with a guidewire lumen and an inflation lumen extending parallel along the side of the catheter.

FIGS. 24A-24D show perspective, side, top and front views, respectively, of a bushing for an embodiment of an atherectomy device.

FIG. 24E is a bottom view of the bushing of FIGS. 24A-24D, while

FIGS. 28A, 28C, 28E, and 28G show perspective views in which the bushing is shown partially transparent as the cutter is exposed by pulling it proximally. FIGS. 28B, 28D, 28F, and 28H show corresponding respective end front-end view of the assemblies of FIGS. 28A, 28C, 28E, and 28G.

FIG. 29A is an outer view of the device with the cutter in a proximal (cutting) position. FIG. 29B is a cross-section of the device of FIG. 29A. FIG. 29C shows the device with the inflatable element in an expanded configuration.

FIGS. 30A-30D show a handle for use with the atherectomy device of FIGS. 29A-29C. FIG. 30A is an external view of the handle. FIG. 30B shows a view of the handle of FIG. 30A with the outer shell removed. FIG. 30C shows a close-up of the handle with the drive bridge removed. FIG. 30D shows a view of a bearing extending within the handle.

FIG. 31A is an outer view of the device with the cutter in a proximal (cutting) position. FIG. 31B is a cross-section of the device of FIG. 31A. FIG. 31C is a cross-section through the outer shaft of the device of FIG. 31A. FIG. 31D shows the inflatable element of the device. FIG. 31E shows a close-up view of the imaging portion of the device.

FIG. 32A shows the break-out port of the handle for management of the drive shaft, imaging shaft, and balloon inflation lumen. FIG. 32B shows is a diagram of the handle components.

FIG. 33A shows the inner portions of the knob. FIG. 33B show the inner portions of the knob with the spiral track in transparent. FIG. 33C shows the inner portions with a sleeve in transparent. FIG. 33D shows the inner portions and sleeve with an outer portion in transparent. FIG. 33E shows the inner portions with a slide in transparent that is in the proximal-most position. FIG. 33F shows the inner portions with a slide in transparent that is in the distal-most position.

FIGS. 34A-34B show a variation of an atherectomy catheter having an inflatable element configured to deflect the nosecone away from the catheter body at a hinge point to expose a cutter. FIG. 34A shows a variation of a distal end of an atherectomy catheter with the nosecone in a closed position. FIG. 34B shows a variation of a distal end of the atherectomy catheter with the nosecone in an open position. This embodiment includes a balloon mechanism configured to open the nosecone when the balloon is inflated.

FIG. 34C shows the activation mechanism in an open position. FIG. 34D shows the activation mechanism in a closed position.

FIGS. 36A-36B show a first embodiment of a handle configured such that the inner drive shaft can be extended axially at the distal end without requiring axial movement of the drive shaft at the proximal end. FIG. 36A shows the drive shaft in the compressed configuration. FIG. 36B shows the drive shaft in the extended configuration.

FIGS. 37A-37B shows a second embodiment of a handle configured such that the inner drive shaft can be extended axially at the distal end without requiring axial movement of the drive shaft at the proximal end. FIG. 37A shows the drive shaft in the compressed configuration. FIG. 37B shows the drive shaft in the extended configuration.

FIG. 41A is an outer view of the device. FIG. 41B includes a transparent outer shaft and nosecone so as to show the drive shaft and imaging element therein. FIG. 41C shows the drive shaft and cutter in an extended (distal) packing position. FIG. 41D is a cross-section of the device.

DETAILED DESCRIPTION

Figure 1A:
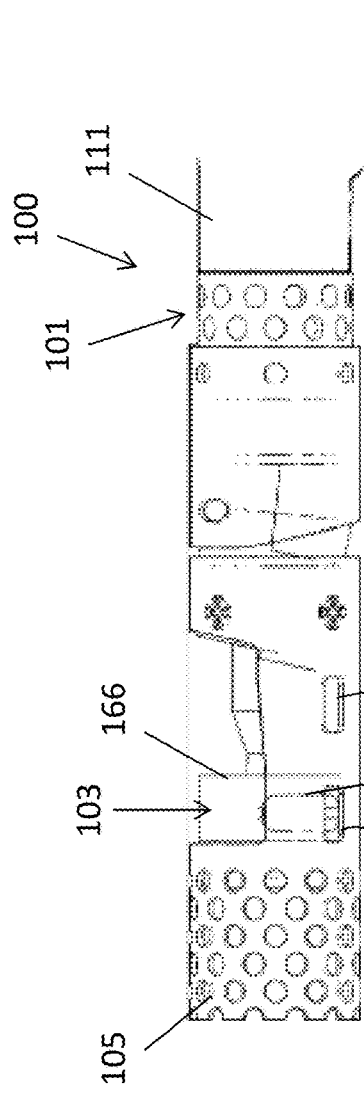
FIGS. 1A illustrates a side perspective view of the end of an exemplary atherectomy device having an offset hinged region, a bushing, and an imaging/cutting assembly with a neck region that engages the bushing.
Figure 1B:
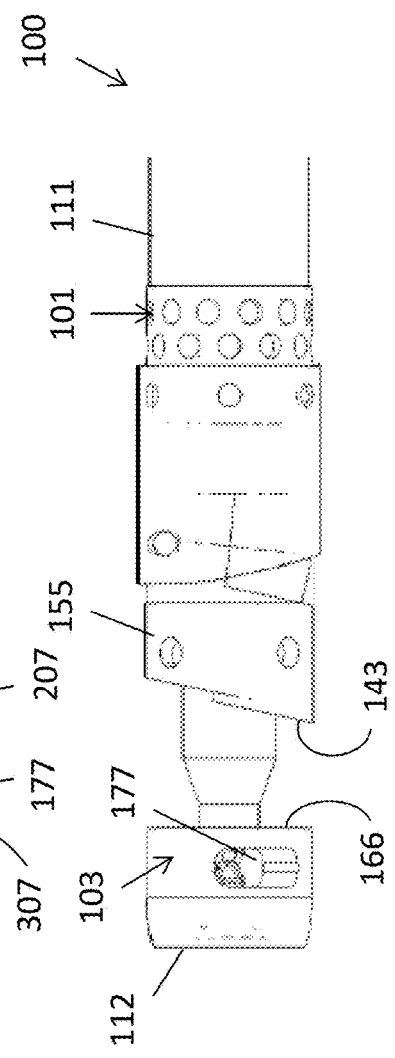
FIG. 1B shows the catheter of FIG. 1A with the housing for the hollow distal tip removed.
Figure 1C:
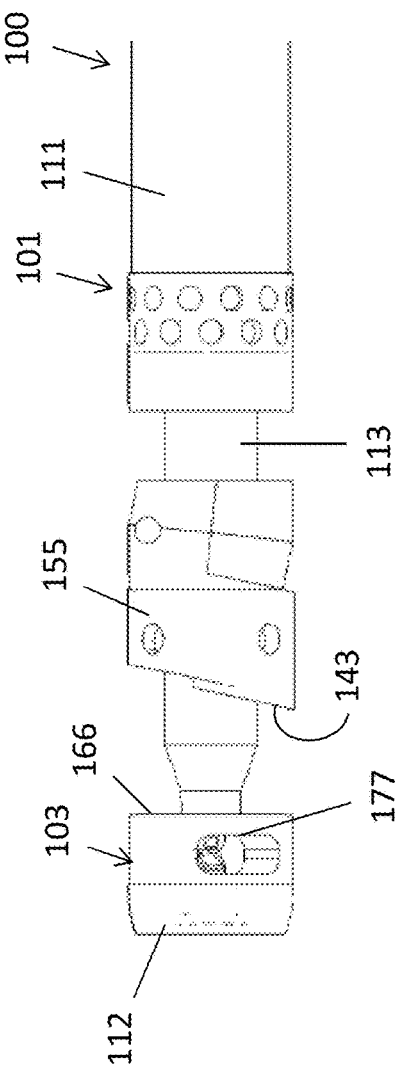
FIG. 1C shows the catheter of FIG. 1A and FIG. 1B with the proximal connector to the outer sleeve of the elongate body removed, showing the bushing and rotatable drive shaft.

Described herein are atherectomy catheters and occlusion-crossing catheters. In general, the atherectomy catheters can include a rotatable cutter connected to a drive shaft. Further, the atherectomy catheters can include on-board imaging, such as optical coherence tomography (OCT) imaging. The atherectomy catheters can include a distal housing (nosecone) configured to hold excised tissue. The drive shaft can be moved distally to pack the excised tissue into the nosecone.

The atherectomy catheters described herein can include a catheter shaft with a drive chassis on the end. The drive chassis includes a stout torque coil ("imaging torqueing coil"/drive shaft) for rotating an imaging element, a cutter, and an imaging optical fiber in the center of the torque coil. Both the imaging elements and the cutter can be part of a head that rotates with the driveshaft. The head can rotate in a single direction (e.g., clockwise). The head can further slide distally/proximally by pushing or pulling the torque coil/drive shaft. As a result of the movement of the driveshaft, a nosecone configured to hold tissue can be displaced. In some embodiments, the nosecone can open and close using an off-axis hinge. In other embodiments, a cam member and cam slot can be used to open and close the nosecone.

In some embodiments, the atherectomy devices described herein can include an inflatable element configured to urge the cutter against the vessel wall. In some embodiments, the inflatable element can activate a hinge mechanism to hinge the nosecone off-axis with the catheter body, thereby exposing the cutter. In such embodiments, a biasing mechanism, such as a wedge, can optionally be used to realign the nosecone and the catheter body. In other embodiments, the inflatable element can urge the cutter against the vessel wall without a separate hinge mechanism. In such embodiments, the cutting window in the catheter can be sized so as to allow the tissue to invaginate within the cutting window and be excised by the rotatable cutter.

In some embodiments, the atherectomy devices described herein can be configured such that the imaging element and the cutter are driven by the same shaft. In other embodiments, there can be a separate imaging shaft and a separate drive shaft to separately control the distal rotation of the imaging element and the cutter, thereby advantageously reducing or eliminating nonuniform rotational distortion (NURD) in the resulting image. In such embodiments, the imaging and drive shafts can be driven by the same rotational mechanism at the proximal end. In such embodiments, the drive shaft and cutter can further advantageously be translated axially without requiring translation of the imaging shaft and imaging element.

Handles are also described herein for use with atherectomy devices. In some embodiments, the handle is configured to rotate an imaging shaft and a drive shaft concurrently while providing axial translation of only the drive shaft. In other embodiments, the handle is configured to provide axial movement of an optical fiber (with a drive shaft) at a distal end of the handle but not the proximal end of the handle.

FIGS. 1A-3 show an example of an atherectomy catheter 100 including a nosecone that deflects to expose a cutter. The atherectomy catheter 100 can include a catheter body 101 having an outer shaft 111, a cutter 103 at a distal end of the catheter body 101, and a nosecone 105 at a distal end of the catheter body 101. The nosecone 105 can further include a cutting window 107 through which the cutting edge 112 of the cutter 103 can be exposed. The nosecone 105 can be configured to deflect away from the longitudinal axis of the catheter body 101 about a hinge point 1109, as described further below. This deflection can expose the cutter 103 through the cutting window 107 and/or radially push the cutter 103 into a wall of the vessel in which the atherectomy catheter is inserted.

Referring to FIGS. 1A-2C, the cutter 103 can be positioned between the catheter body 101 and the nosecone 105 via a bushing 155. In some embodiments, the cutter 103 can be an annular cutter with a sharp distal edge 112. The cutter 103 can be attached to a drive shaft 113 configured to rotate the cutter 103. As described in greater detail below, the bushing 155 shown in FIGS. 1A-3 is just one example of a bushing. Other examples (see, e.g., FIGS. 7A-7G and 24A-24G) are shown and described below, and include different or alternative features that may be incorporated into any of these variations described herein.

Figure 2A:
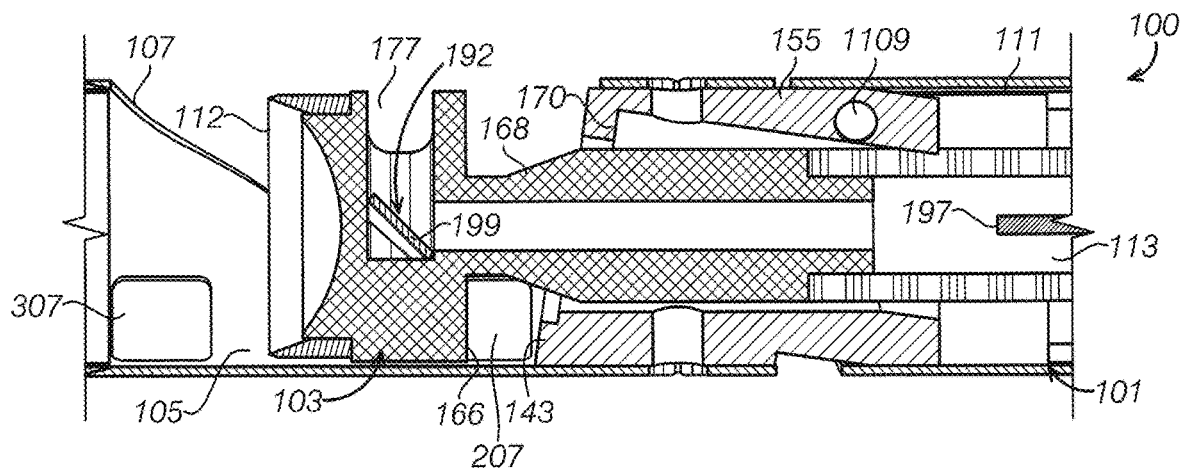
FIG. 2A shows a sectional view though an atherectomy catheter such as the one shown in FIGS. 1A-1C, with the distal tip in-line with the elongate (proximal) body region.
Figure 2B:
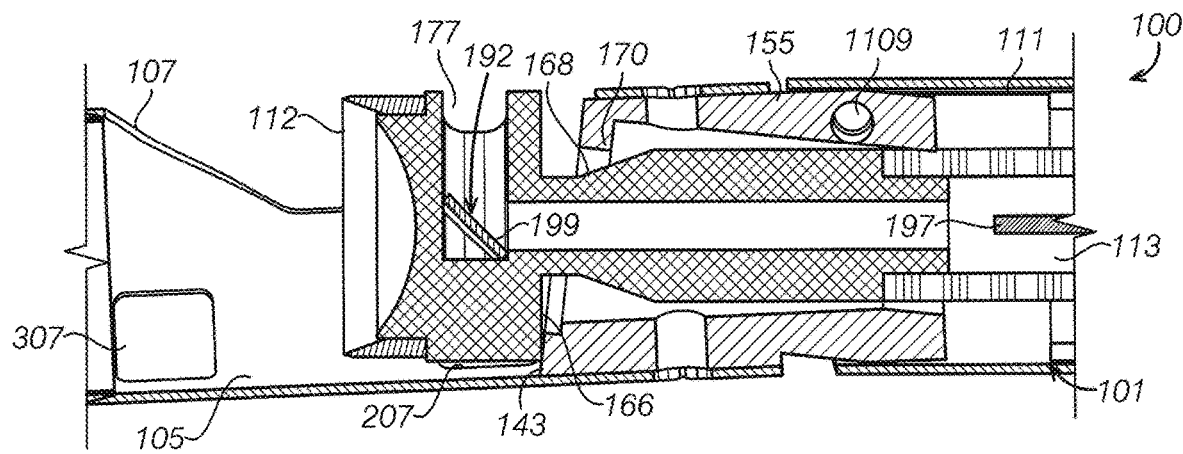
FIG. 2B shows the catheter of FIG. 2A as the tip beings to be displaced downward.

Further, referring still to FIGS. 2A and 2B, the atherectomy catheter 100 can include an imaging element 192, such as an OCT imaging element, within the cutter 103 and proximal to the cutting edge 112 of the cutter 103. The imaging element 192 can include an optical fiber 197 that runs substantially on-axis through the center of the elongate body, such as through the driveshaft 113, to transmit the OCT signal. Further, the optical fiber 197 can run straight throughout the catheter body 101 without bending. The optical fiber 197 can be attached at the distal end to the cutter 103, such as in a slot 177 in the cutter 103. The slot can have a length that extends at least to the center of the cutter 103 so as to allow the optical fiber 197 to remain on-axis without a bend through the length of the catheter body 101 and the cutter 103. Aside from the attachment to the cutter 103, the optical fiber 197 can be otherwise be free to float within the catheter body or drive shaft 113. In other embodiments, the optical fiber 197 can be attached to the drive shaft 113 along the length thereof.

Figure 2C:
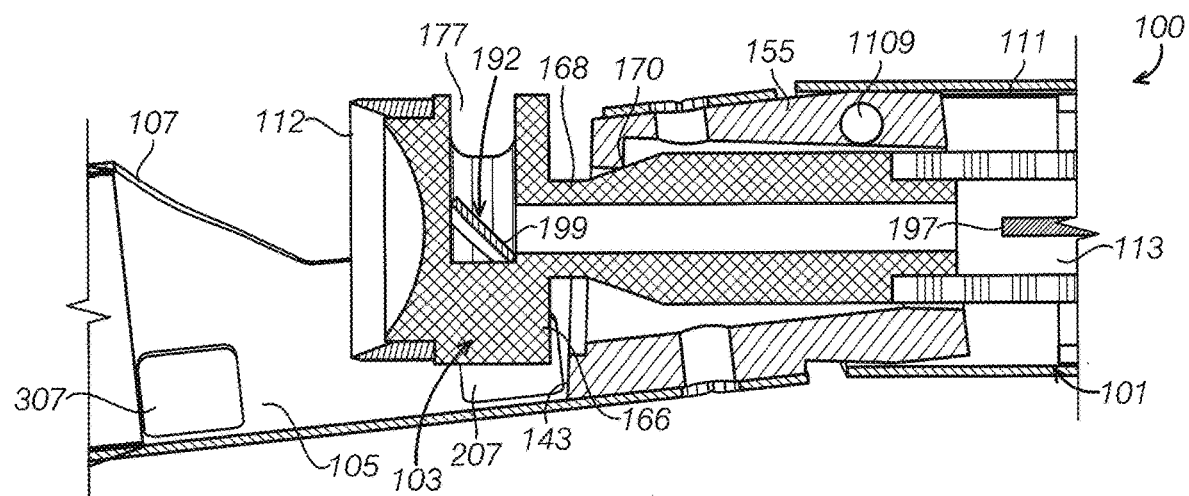
FIG. 2C shows the catheter of FIG. 2A with the tip fully displaced downward, exposing the cutting edge of the cutting/imaging assembly.

As shown in FIGS. 2A-2C, the imaging element 192 can include a reflective element 199, such as a mirror. The reflective element 199 can be located within the slot 177 in the cutter 103 to radially direct light from the optical fiber 197 into the adjacent tissue (through the cutter window 107). The reflective element 199 can be oriented at an angle relative to the axis of the optical fiber 197, such as at a 35-55 degree angle, e.g. 45 degree angle, to reflect light into the tissue. The distal end of the optical fiber 197 can be located less than 3 mm from the cutting edge, such as less than 1 mm from the cutting edge, such as less than 0.5 mm. By having the imaging element 192 close to the cutting edge, the resulting image can advantageously align with the portions of the vessel being cut.

In use, the outer shaft 111 can be configured to be turned, such as turned manually, to position the cutter window 107, cutter 103, and/or the imaging element 192 toward the desired location. The driveshaft 113 can then be rotated to rotate the cutter 103 and the imaging elements 197. Rotation of the cutter can provide cutting due to the rotational motion of the cutting edge and provide the rotation necessary to image the vessel wall via the imaging element. The drive shaft can be rotated at up to 2,000 rpm, such as approximately 1,000 rpm in a single direction, though rotation in both directions or at higher or lower speeds is possible.

Referring to FIGS. 2A-2C, the drive shaft 113 can further be configured to translate axially in the proximal and/or distal directions. Such axial movement of the drive shaft 113 can open and/or close the nosecone 105 about the hinge point 1109 (e.g., a pin in the bushing 155) to expose or conceal and protect the cutting edge 112 of the cutter 103. For example, the bushing 155 can include an inner flange 170 that extends radially inwards. The inner flange 170 can be positioned distal to the hinge point 1109. The bushing 155 can further include sloped outer distal surface 143 that angles radially inward from the distal end to the proximal end. Finally, the cutter 103 can include a proximal edge 166 and a tapered neck 168 that gets narrower from the driveshaft 113 to the head of the cutter 103. The interaction of these various elements can open and close the nosecone 105.

In one embodiment, proximal retraction of the drive shaft 113 opens the nosecone 105 to expose the cutter. For example, as the driveshaft 113 is pulled proximally, the proximal edge 166 of the cutter 103 is forced against the sloped distal surface 143 of the bushing 155. Because the sloped distal surface 143 angles radially inward from the distal end to the proximal end, the cutter 103 forces the bushing 155, and thus the nosecone 105, to deflect away from the longitudinal axis of the catheter body 101, thereby opening the nosecone 105 (see the transition from FIGS. 2A to 2B and 2B to 2C). The cutting window 107 can have an opening that is larger than the diameter of the cutter 103 and cutting edge 112 to allow the cutter 103 to protrude out of the nosecone 105 when the nosecone 105 is deflected.

In one embodiment, distal movement of the drive shaft 113 closes the nosecone 105. For example, as shown in FIGS. 2A-2C, when the drive shaft 113 is pushed distally, the tapered neck 168 of the cutter 103 will correspondingly move distally. The distal movement of the tapered neck 168 causes the inner flange 170 of the bushing 155 to drag along the widening edges of the tapered neck 168, thereby lifting the bushing 155, and correspondingly, closing the nosecone 105 (see the transition from FIGS. 2C to 2B and 2B to 2A). Because the hinge point is proximal to the inner flange 170, a mechanical advantage is achieved that allows for complete closing of the nosecone.

FIGS. 7A-7D show close-ups of the bushing 155. As shown, the bushing 155 can include two intersecting channels 721, 723 configured to hold the necked portion 168 of the imaging subassembly therein when the nosecone is in the open configuration (channel 723) and the closed configuration (channel 721). Channel 721 extends through a long distal to proximal axis of the bushing 155 while channel 723 extends at an angle relative to channel 721 and overlaps therewith. The bushing 155 can further include a hinge channel 745 formed through a top peripheral region of the bushing 155 so as to provide the pivot point 1109. The hinge channel 745 can be transverse to the channel 721.

Any of the bushings described herein may be referred to as multi-channel bushings, because they may include at least two overlapping channels, in which one of the channels is at an angle relative to the other.

For example, any of the apparatuses described herein may be atherectomy catheter devices that include a multi-channeled bushing. As shown and described in FIGS. 1A-2C, a catheter may include an elongate body 101 with a tip 105 (e.g., nosecone, distal tip, etc.) extending from a distal end of the elongate body, a drive shaft 113 extending within the elongate body, and a bushing pivotally connected to the elongate body and/or tip.

In general, a bushing 155' (as shown in FIGS. 7A-7G) may include a bushing body 156. The bushing body may be any appropriate material, including polymers (e.g., plastics, Polyether ether ketone, polyethylene, polypropylene, polystyrene, oolyester, polycarbonate, polyvinyl chloride, polyethersulfone, polyacrylate, polysulfone, polyetheretherketone, thermoplastic elastomers, silicone, parylene, fluoropolymers, etc.), metals (including alloys), and ceramics.

The bushing typically includes one or more (preferably two) hinge points 745 on a side of the bushing body. In FIGS. 7A-7G the hinge points are a hinge channel that extends perpendicular to the elongate axis of the bushing body through a region that is off-axis, meaning it is offset from a midline along a distal-to-proximal axis of the bushing body. The hinge point in this example is part of a hinge channel formed through a top peripheral region of the bushing body (extending transverse to the long axis of the bushing, including transverse to the two channels 721, 723 extending distally to proximally).

As mentioned, the bushing body may include a first channel 721 extending proximally to distally through the bushing body and a second channel 723 extending proximally to distally through the bushing body. The first and second channels overlap. In general, the first channel may have a diameter that is greater than or equal to the diameter of the second channel.

Figure 7A:
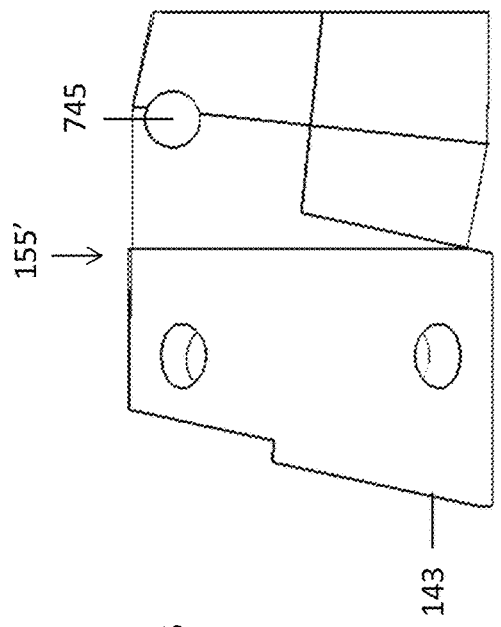
FIGS. 7A-7D show perspective, side, top and front views, respectively of a bushing for an atherectomy device.
Figure 7C:
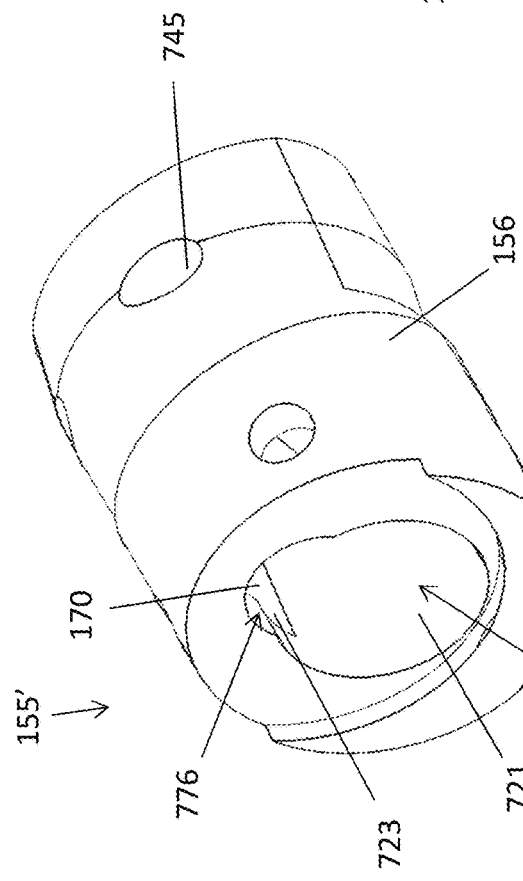
Figure 7B:
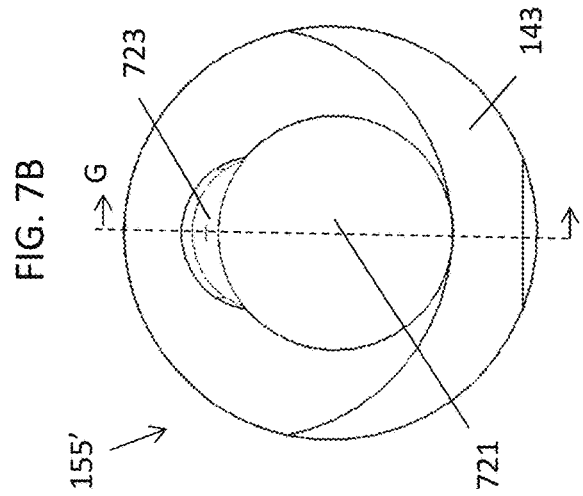
Figure 7D:
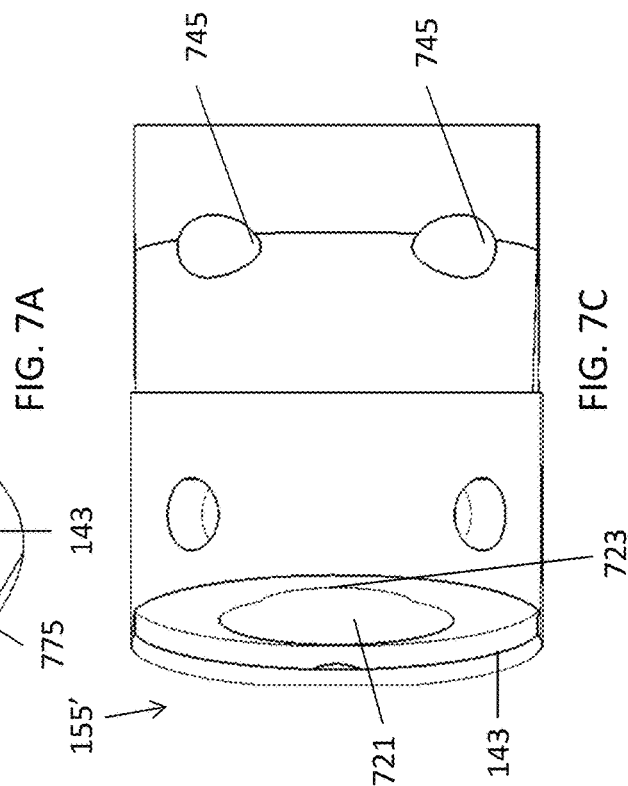
Figure 7F:
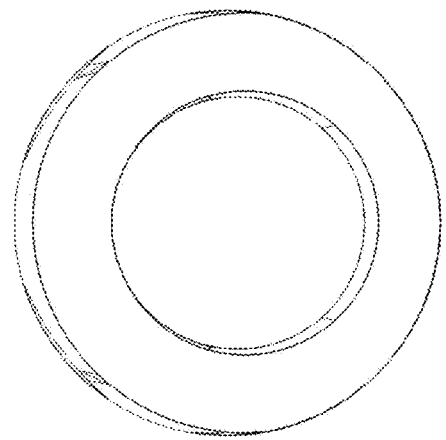
FIG. 7F is a back view.
Figure 7E:
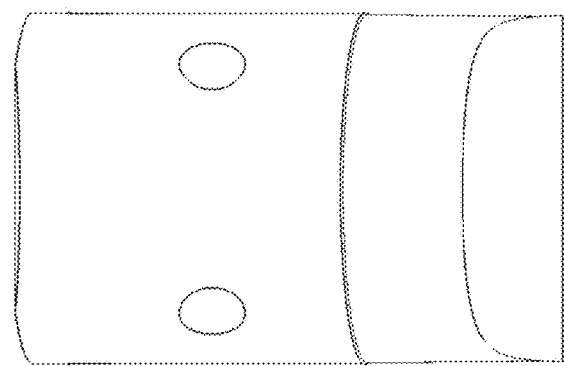
FIG. 7E is a bottom view.
Figure 7G:
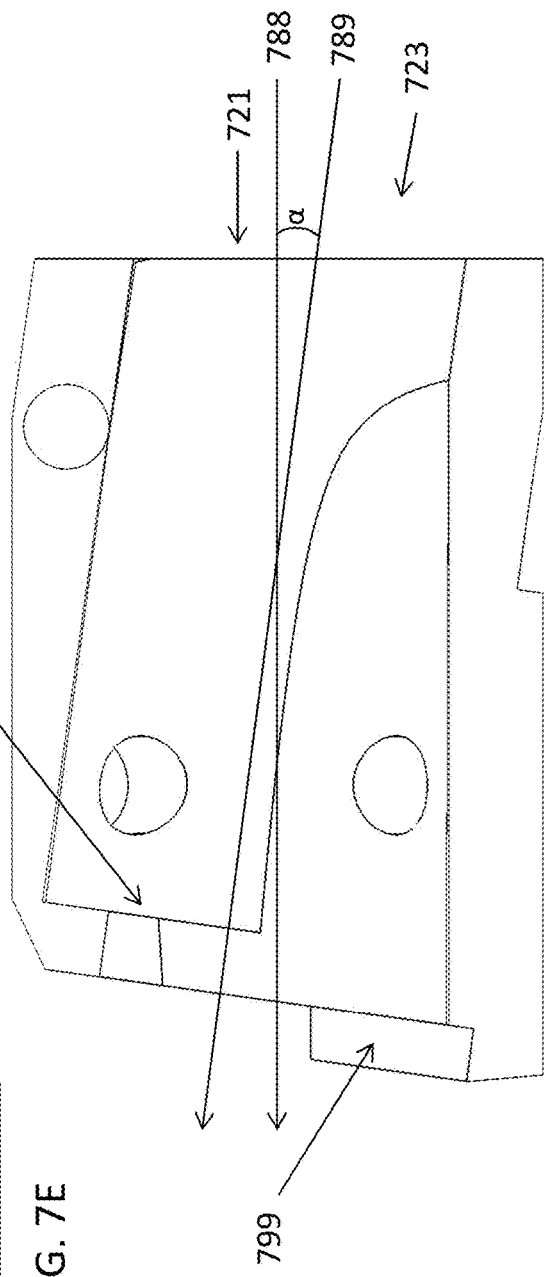
FIG. 7G is a sectional longitudinal view.

As mentioned, the long axis 788 of the first channel may extend through the bushing, proximally to distally. The long axis 789 of the second channel also extends through the bushing proximally to distally, overlapping with the first channel, as shown in FIG. 7G. In the longitudinal section (G) through the bushing shown in FIG. 7C, the first channel 721 overlaps with the second channel 723, and the angle (α) between the first and second channels is typically between about 1° and about 45° (e.g., between a lower angle of 2°, 3°, 4°, 5°, 7°, 10°, 12°, 15°, 17°, 20°, etc.) and an upper angle of 15°, 20°, 22°, 25°, 30°, 35°, 40°, 45°, 50°, 60°, etc., where the lower angle is always less than the upper angle).

The bushing may also include a first opening 775 at a distal end of the bushing body into the first channel (visible in FIG. 7A), and a second opening 776 at the distal end of the bushing body into the second channel, wherein the first and second openings overlap.

In general, any of these apparatuses may also include a cutter. The cutter 103 may generally include a distal cutting head 119 with a cutting edge 112, an elongate cylindrical body 123, and a neck region 168 extending between the distal cutting edge and the elongate cylindrical body, wherein the drive shaft is coupled to the elongate cylindrical body.

FIGS. 24A-24H and 25 illustrate another variation of a bushing that may be used with any of the atherectomy catheter devices described herein. As mentioned, the atherectomy catheters described herein may generally include an elongate body (not shown) to which a multi-channeled bushing is attached. The bushing typically makes the bending joint between the distal tip region and the more proximal elongate body or shaft. As described above, an internal torque shaft (which may be woven, or the like) may be connected (e.g., by soldering, crimping, etc.) to the proximal end of a cutter. The cutter may be positioned within the bushing, as will be described in greater detail with reference to FIGS. 27-27G, below. The bushing may be attached via hinge pin to the proximal elongate body, and in particular, the off-axis or off-center hinge point on the side of the bushing. Multiple hinge pins may be used or a single hinge pin may be used. The pin may secure the bushing to the covering forming the elongate body within which the drive shaft extends. The distal end of the proximal shaft may include an adapter to which the pin (hinge pin) may be attached, e.g., by welding, allowing the bushing to rotate about the off-center/off-axis hinging region. The distal end of the bushing may be connected to the nosecone forming the distal tip of the apparatus. The nosecone may be hollow to allow packing of cut material within it. The bushing may be connected to the nosecone by any appropriate manner, including crimping and/or welding and/or adhesive, etc.

Any of the exposed edges, such as the edges of the bushing, adapter, nosecone, etc. may be radiused (e.g., have a radiused edge) to prevent undesirable damage to the tissue.

Figure 25:
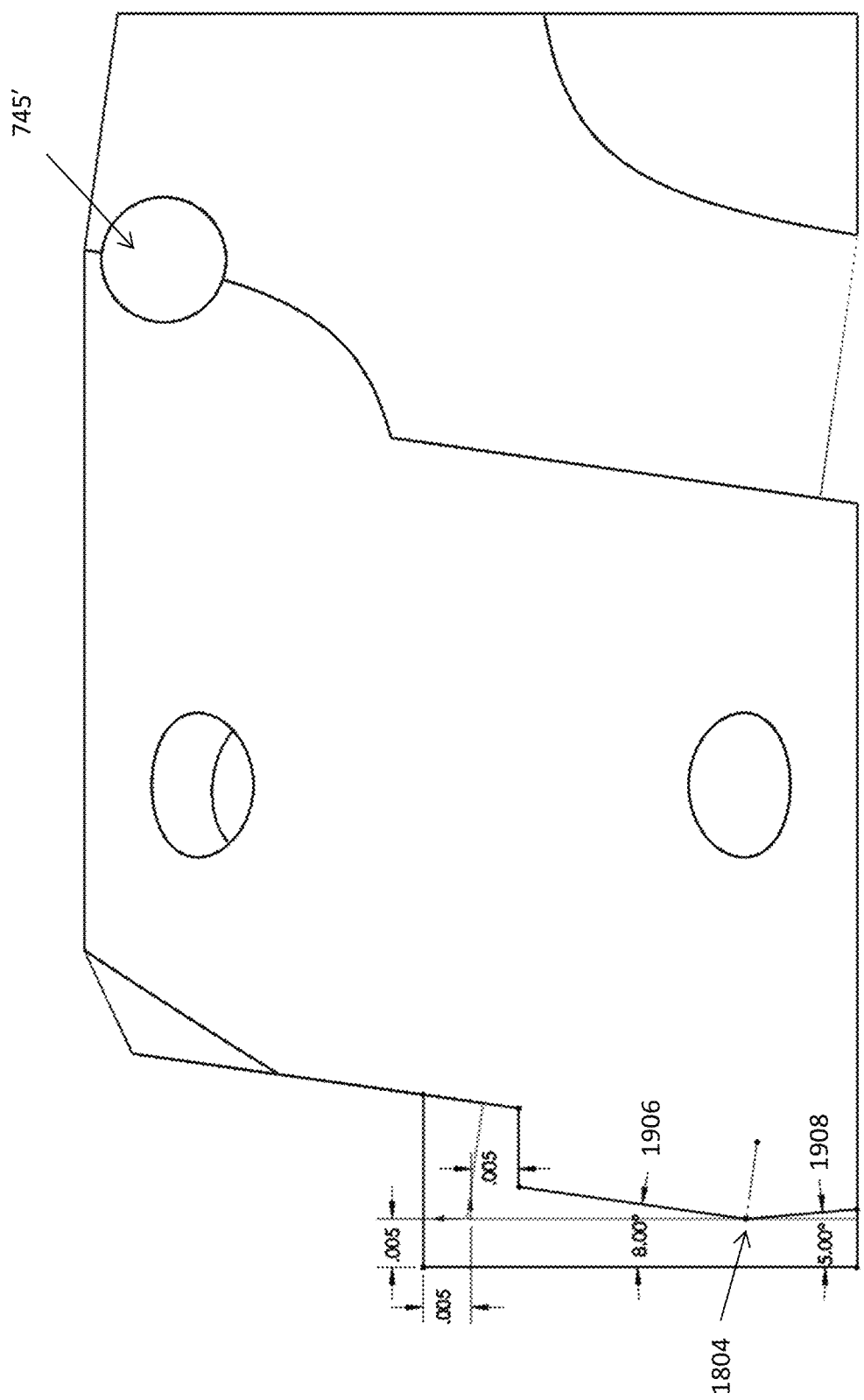
FIG. 25 is a side view, showing exemplary dimensions, of one variations of a bushing such as the bushing shown in FIGS. 24A-24H.
Figure 26B:
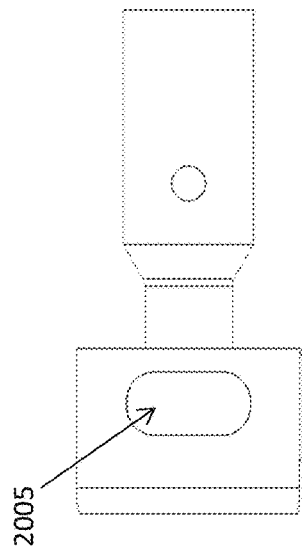
FIGS. 26A-26D illustrate perspective, top, side and bottom views, respectively, of an exemplary catheter having an eccentric distal cutting head with a cutting edge, an elongate cylindrical body, and a neck region.
Figure 26C:
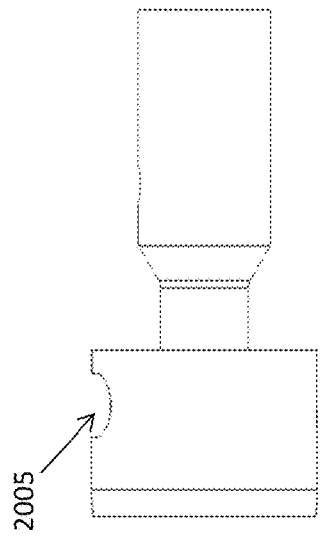
Figure 26D:
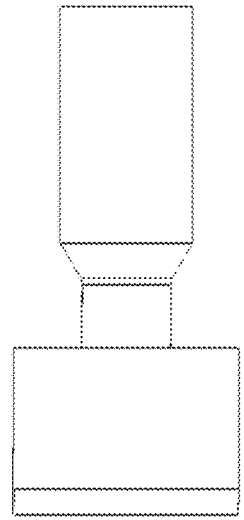
Figure 26A:
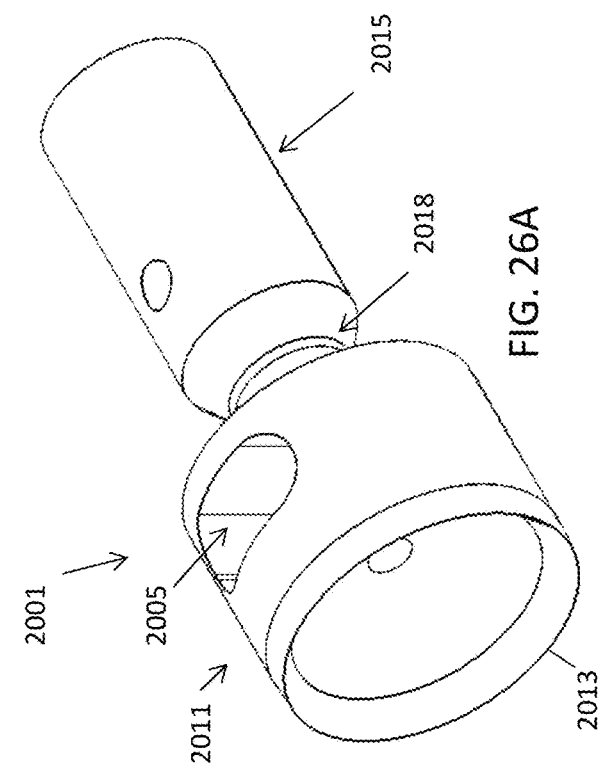

In any of the bushings described herein, including the example shown in FIGS. 24A-25, the bushing may include a bushing body, 156', a hinge point (or hinge channel 745' forming one or more hinge points) on a side of the bushing body, a first channel 721' having a first opening 775') extending proximally to distally through the bushing body, and a second channel 723' (having a second opening 776' that is overlapping, but not coextensive with the first channel opening) extending proximally to distally through the bushing body. The second channel generally has a diameter that is less than a diameter of the first channel, and the second channel may be angled between 1° and 45° relative to the first channel, as illustrated in FIG. 24G. The angle (α) between the long axis of the first channel 788' relative to the long axis of the second channel 789' is between 1° and 45° (shown in FIG. 24G is approximately 15°).

As shown in FIGS. 26A-26D, any of these apparatuses may include a cutter 2001 having a distal cutting head 2011 with a cutting edge 2013, an elongate cylindrical body 2015, and a neck region 2018 extending between the distal cutting edge 2013 and the elongate cylindrical body 2015. As mentioned, the drive shaft may be coupled to the elongate cylindrical body. The cutter may also be adapted to form the OCT lens/imaging window, as described herein. For example, in FIGS. 26B-26D, the cutter head includes a window region 2005 that is continuous with an internal passage through the cutter, into which an OCT lens may be formed at the distal end of an optical fiber. The lens may include a mirror (not shown) and/or OCT-transparent epoxy or resin holding the distal end of the fiber in position (not shown).

The distal-most edge of the bushing may be straight or curved line 1804 that is formed at the flange region so that the bushing may contact the back of the cutter at a point or line. This will be illustrated below with reference to FIGS. 28A-28H. For example, FIG. 24B illustrates a profile including the distal edge of the bushing. In this example, the distal end of the bushing includes a distal-most flange or rim 143 that forms a line or point 1804 between two angled surfaces. The surface extending on one side (e.g., upper surface 1906) of this line 1804 has an angle relative to the long axis of the first channel through the bushing that is approximately the same as or greater than the angle that the nosecone is deflected relative to the distal end of the elongate body of the apparatus when the cutter is exposed. This is illustrated, for example in FIG. 25, which includes exemplary dimensions (in inches and degrees). In FIG. 25, the distal most edge 1804 is formed by an angled upper surface 1906 of the partial flange and the oppositely-angled lower surface 1908 of the partial flange. The angle of this upper surface relative to the long axis of the first channel through the flange is shown as 8° degrees from the perpendicular of the long axis. Similarly, the angel of the lower surface 1908 relative to the long axis of the first channel through the flange is 5° degrees from the perpendicular of the long axis, as shown. This flange region 1809 extends around just the bottom of the distal end of the bushing, and may be sized to hold the cutter head of the cutter within the bushing distal end when the cutter is retracted fully proximally.

Because of the configuration of the bushing, including in particular the features described above, the bushing may be actuated to move tilt the distal tip of the catheter in-line with the elongate body or at an angle to the elongate body, as shown in FIGS. 2A-2C. In this example, distal movement of the drive shaft extends the cylindrical body of the cutter within the first channel of the bushing and drives the tip about the hinge point to axially align the tip with the elongate body and at least partially cover the cutting edge. In addition, proximal movement of the drive shaft extends the neck region of the cutter within the second channel of the bushing and drives the tip about the hinge point to angle the tip relative to the elongate body and at least partially expose the cutting edge. Alternatively or additionally, pushing the drive shaft distally may drive the neck region against the inner flange 798 (visible in the section shown in FIG. 7G), while pulling the drive shaft proximally may drive the proximal-facing (back, proximal side) of the cutter against an outer flange 143, which may include a sloped distal surface.

Figure 27:
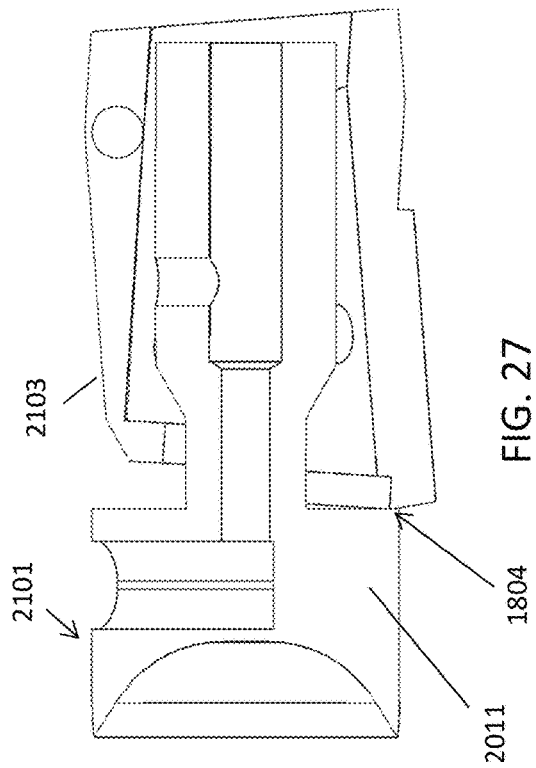
FIG. 27 is a sectional view through the long axis of the cutter engaging a bushing. In practice, the bushing may be connected to the balloon and a concentric proximal body portion of the tip of the atherectomy device (not shown) and pivotally connected to the shaft (proximal end) of the atherectomy device, and the cutter may be secured at the distal end to a torque shaft (not shown in FIG. 27).
Figure 28A:
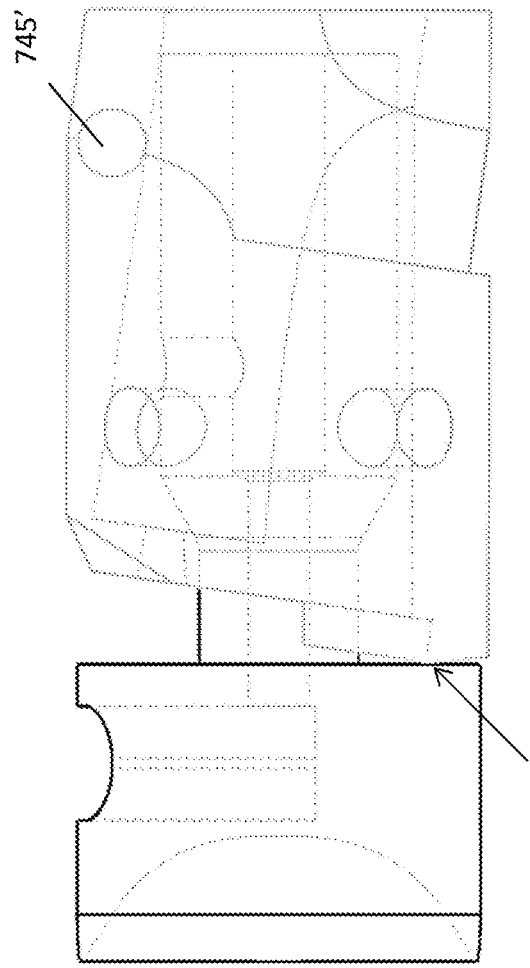
FIGS. 28A-28H illustrate relative movements of the bushing and cutter.
Figure 28C:
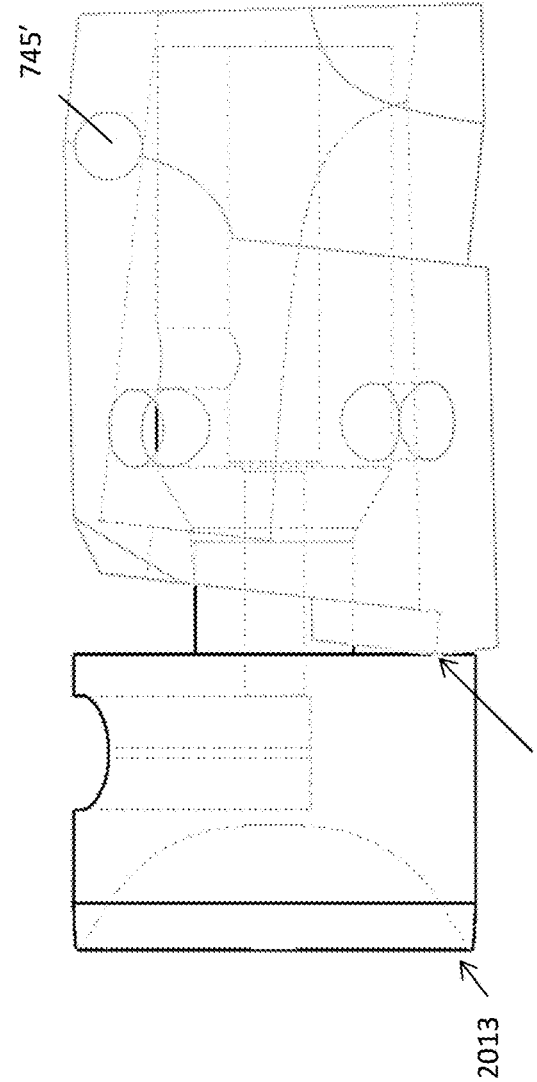
Figure 28B:
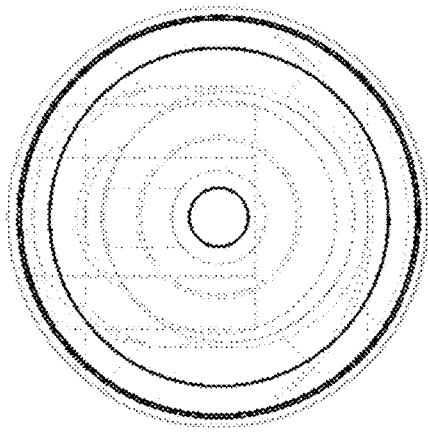
Figure 28D:
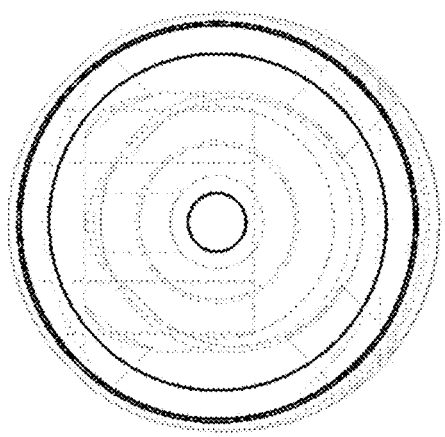
Figure 28E:
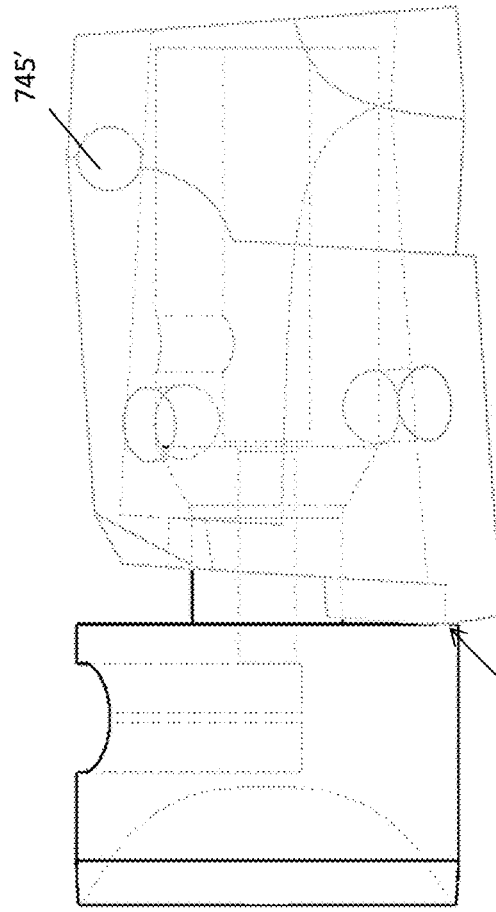
Figure 28G:
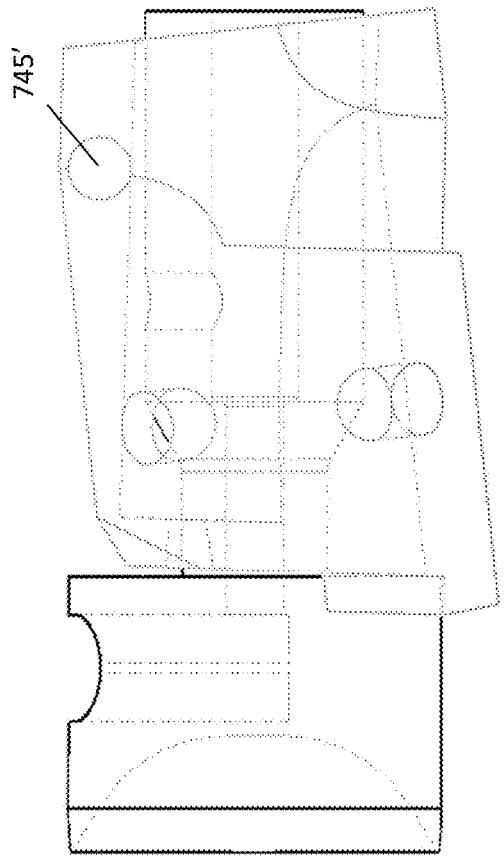
Figure 28F:
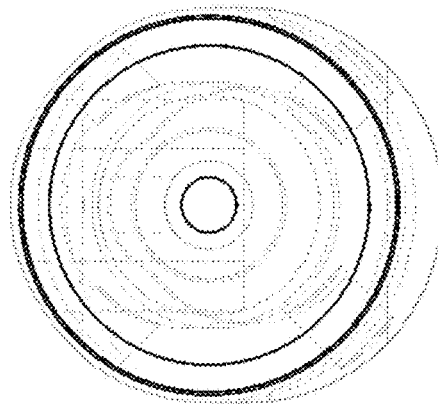
Figure 28H:
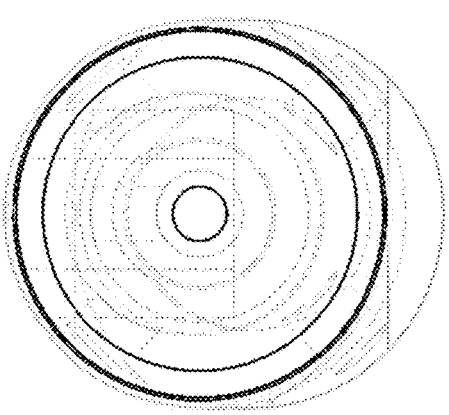

FIG. 27 illustrates one example of a cutter engaged 2101 with a bushing 2103. The bushing in this example is similar to the bushing shown in FIGS. 24A-24H. The bushing engages with the cutter head 2011 only at the distal-most point or line 1804 of the bushing. In this example, the bushing is a PEEK bushing, and the cutter is metal. In FIG. 28A, the back of the cutter head (rear of the cutter face) contacts the distal-most (leading) edge or point of the bushing 1804, when the cutter is pulled back to deploy the cutter and expose it for cutting. Pulling back on the torque shaft forces this distal/leading edge of the bushing against the back of the cutter, which may be rotating. In FIG. 28A, the tip (nose cone) of the atherectomy catheter is in the same line as the elongate axis, and the cutter is flush or nearly flush with the outer wall of the distal end of the catheter, preventing cutting within the vessel. As shown in FIG. 28B, the cutter and bushing are in line. At the start of pull-back of the cutter, e.g., by pulling the torque shaft, a moment is created that begins to tilt the bushing downward, as shown in FIG. 28C. In FIG. 28C, the leading edge of the bushing begins to ride up the rear face of the cutter, and the bushing (to which the nosecone is fixedly attached distally) beings to rotate about the off-axis hinge point 745' driving the nosecone (not shown) down, and beginning to expose the cutter's cutting edge 2013, which is also visible in the end view shown in FIG. 28D. This process continues, as shown in FIG. 28E; the moment arm between the leading edge 1804 of the bushing and the hinge point(s) 745' is sufficiently large so that the force applied by driving the cutter against the leading edge forces the nosecone down, until, as shown in FIG. 28G, the cutter head drops into the partial flange formed by the bushing, and is securely held in this seating position, as shown. Thus, the downward moment is applied so that the leading edge of the bushing rides along the rear face of the cutter until the cutter is seated. FIGS. 28G and 28H show the final position of the cutter (cutter head) seated on the ledge of the bushing.

To reverse this, the distal movement of the drive shaft extends the cylindrical body of the cutter within the first channel of the bushing and drives the tip (nosecone) about the hinge point to axially align the tip with the elongate body and at least partially cover the cutting edge. Similarly, to again deflect the nosecone, proximal movement of the drive shaft will again extend the neck region of the cutter within the second channel of the bushing and drives the tip about the hinge point to angle the tip relative to the elongate body and at least partially expose the cutting edge.

Other mechanisms of opening and closing the nosecone are possible. For example, as shown in FIGS. 4A-4D, in one embodiment, a catheter 200 (having similar features to catheter 100 except the opening and closing mechanisms) can include a cam slot 228 in the bushing 155 that angles toward the cutting window 107 from the proximal end to the distal end. Further, a cam member 290 can be attached to the cutter 103 and configured to extend through the cam slot 228. Thus, as the driveshaft 113, and thus cam member 290, are pushed distally, the cam member 290 will move within the angled cam slot 180. The movement of the cam member 290 within the angled cam slot 180 causes the bushing 155, and thus the nosecone 150, to drop down. Conversely, to close the nosecone, the driveshaft 113 can be pulled proximally, thereby causing the cam member 290 to ride within the cam slot 228 and pull the bushing 155 back into line with the elongate body 101.

Another mechanism of opening and closing a nosecone of an atherectomy catheter 400a,b is shown in FIGS. 11A and 11B and FIGS. 12A and 12B. The catheter 400a,b can have the same features as catheter 100 except that the outer distal surface 443a,b of the bushing 455a,b can be either normal to the longitudinal axis of the device (such that the angle α is 90 degrees), as shown in FIG. 11B or slanted radially outward from the distal end to the proximal end (such that the angle α is greater than 90 degrees and the angle with the longitudinal axis is less than 90 degrees), as shown in FIG. 12B. In the embodiment of FIGS. 12A and 12B, an angled space is provided between the proximal edge 166 of the cutter and the distal surface 443b such that the only point of contact is an inner radial edge 444 of the bushing 455b. The catheter 400a will open and close similarly to as described with respect to catheter 100. However, the catheter 500b will open slightly differently in that only the inner-most radial edge 444 will interact with the proximal edge 166 of the cutter 103, as opposed to the entire surface 443, when the driveshaft 113 is pulled proximally. Such a configuration can advantageously reduce friction while opening the nosecone 105. In some embodiments, the proximal edge 166 can be angled with respect to a longitudinal axis of the catheter; in such cases, the opposing surface 443 of the bushing 455 can be either parallel to or angled (acute or obtuse) with respect to the proximal edge 166.

Figure 3:
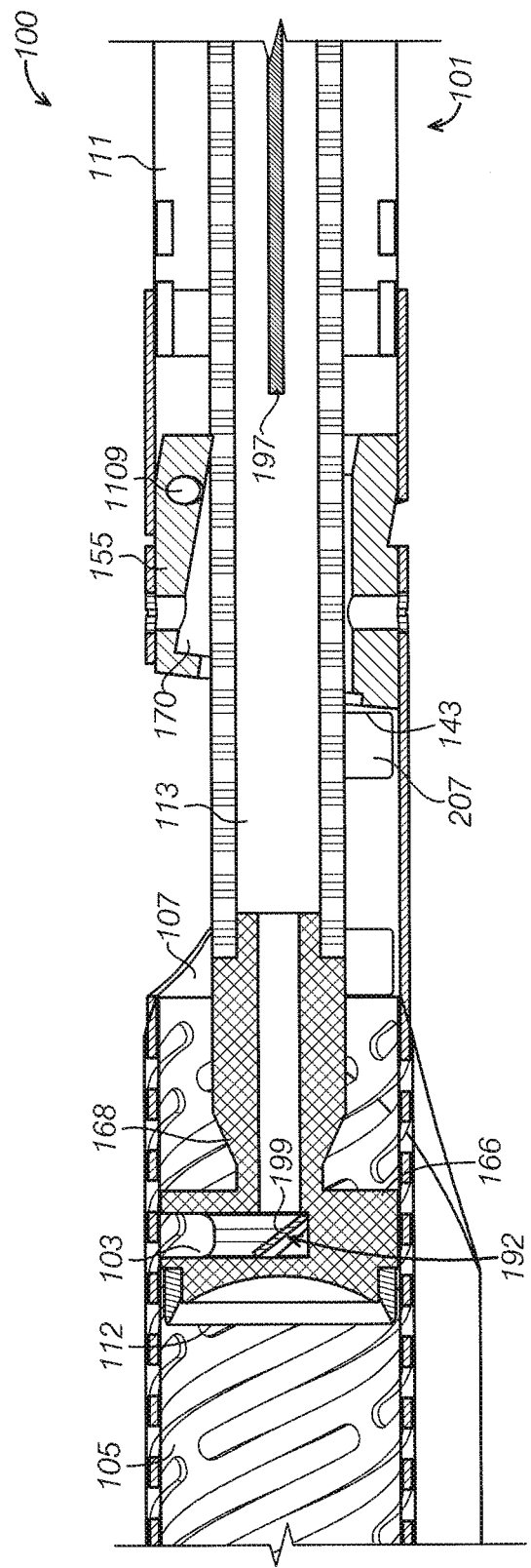
FIG. 3 shows a catheter with the cutting/imaging assembly extended distally into the distal tip region.
Figure 4A:
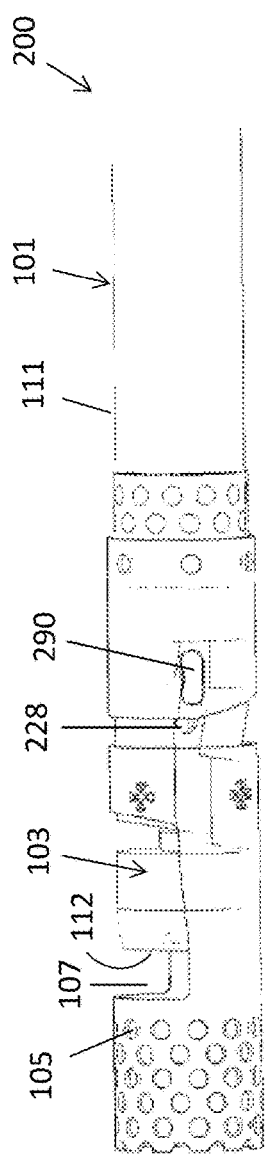
FIGS. 4A-4D illustrate another variation of an atherectomy catheter.
Figure 4B:
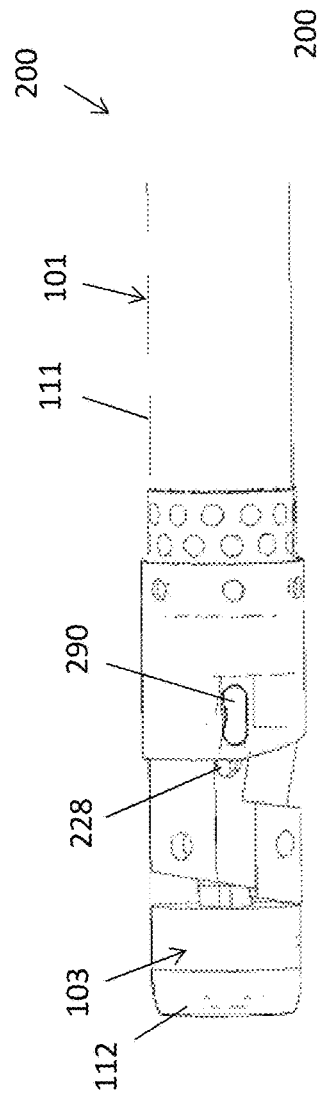
Figure 4C:
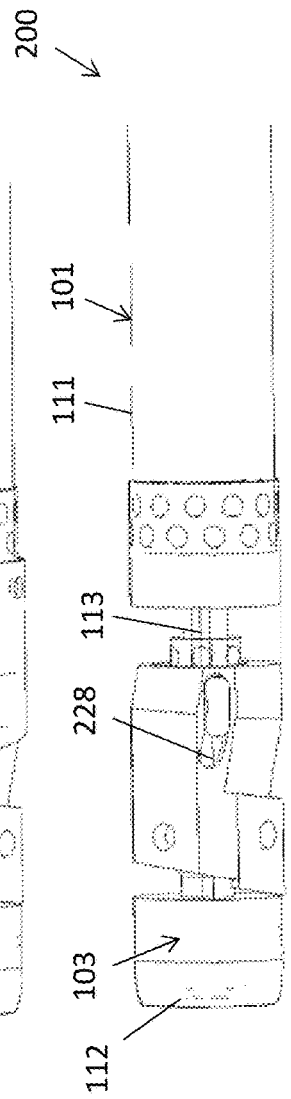
Figure 4D:
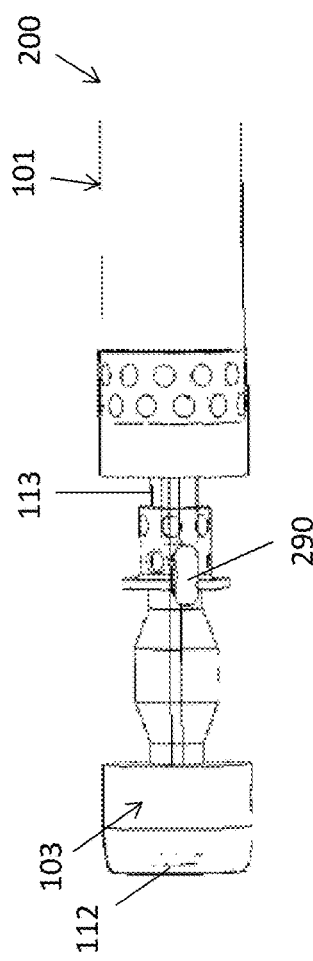

As shown in FIG. 3, the atherectomy catheter 100 (or 200 or 400) can further include a mechanism for packing tissue into the nosecone, such as by moving the drive shaft axially. In one embodiment, movement of the drive shaft 113 distally closes the nosecone 105. Moving the drive shaft 113 further distally will move the cutter 103 into a passive position (i.e., against a distal edge of the window 107) where the cutter 103 can be protected by the edge of the window 107 to avoid undesired cutting of the vessel during use. Moving the drive shaft 113 further distally will move the cutter 103 into the nosecone 105, thus packing tissue with a distal face of the cutter 103, as shown in FIG. 3. The cutter 103 can move more than 0.5 inches, such as more than 1 inch or more than 2 inches into the nosecone 105 to pack the tissue. In some embodiments, the nosecone 105 is formed of a material that is OCT translucent (e.g., non-metallic) so that panoramic OCT images can be taken therethrough.

Figure 16A:
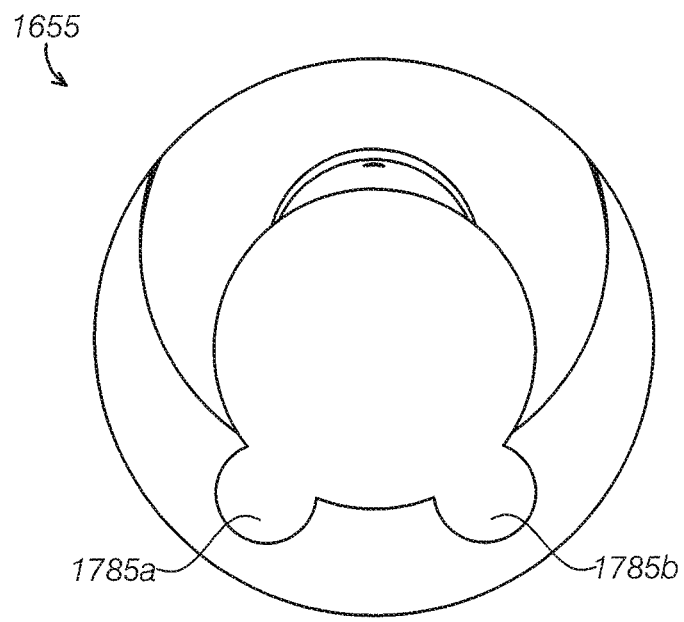
FIGS. 16A and 16B show a bushing having jet channels therethrough to assist in packing of tissue into the nosecone of an atherectomy catheter.
Figure 16B:
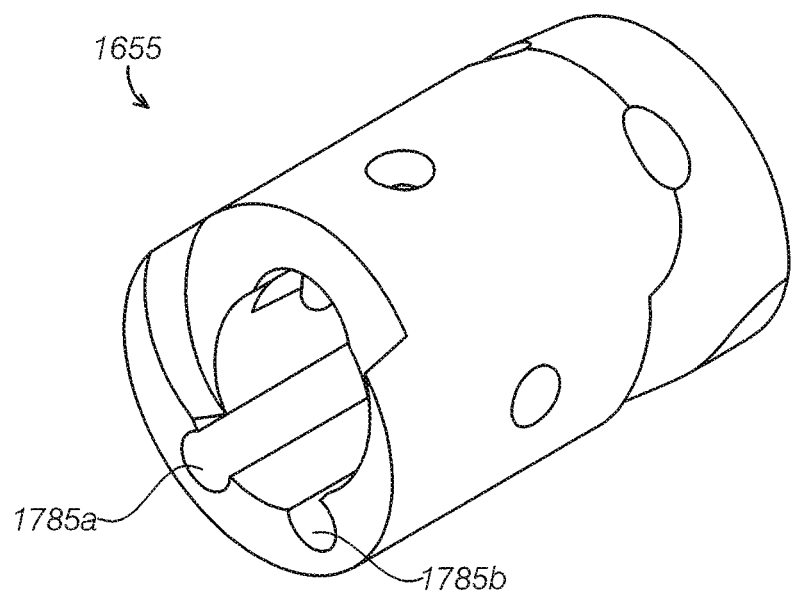

Referring to FIGS. 16A and 16B, in some embodiment a bushing 1655 can include all of the features of the bushings described 1655 above, but can additionally include jet channels 1785a,b cut into the inner circumference thereof and extending from the proximal end to the distal end. The jet channels 1785a,b can connect a fluid line within the elongate body 101 to the nosecone 105. Fluid flowing through the jet channels 1785a,b can increase speed and thus provide enough force to pack cut material into the nosecone and clear the imaging region within the nosecone. Further, the jet channels can create a venturi effect at the distal end of the bushing 1655, which can suck material into the nosecone and/or away from the imaging/cutting head and/or the distal end region of the elongate body.

In one embodiment, the atherectomy catheter 100 (or 200 or 400) includes a guidewire lumen in the nosecone 105, such as a monorail, for use in guiding the catheter. Advantageously, the guidewire lumen can be used as a marker during imaging.

In some embodiments of atherectomy catheters 100, 200, or 400, there can be one or more small imaging windows 207, 307 in the nosecone 105 opposite to the cutting window 107, as shown in FIGS. 1A and 2A-2C. These additional imaging windows 207 can provide more of a 180 degree view during imaging. Further, one set of windows 207 can be more proximal and configured to be axially aligned with the cutter 103 and the imaging element 192 when the nosecone is opened while the other set of windows 307 can be more distal and configured to be axially aligned with the cutter 103 and the imaging element 192 when the nosecone is closed and the cutter 103 is in the passive position. In some embodiments, the imaging windows 307, 207 have different shapes from one another to further help identify cutter position in the resulting OCT images.

Referring to FIGS. 8A-11B, the OCT image catheter with the device will vary depending upon the placement of the imaging device in the three different configurations (nosecone open, nosecone closed with cutter in cutting position, nosecone closed with cutter in packing position). Accordingly, a user can identify, simply by looking at the imaging display, whether the nosecone 105 is displaced and whether the cutter 103 is in the cutting or packing position.

For example, FIG. 8A shows a panoramic image 800 of a surrounding vessel when the cutter 103 (and, correspondingly, the imaging sensor) is in the cutting position, as shown in FIG. 8B. The wall of the nosecone 105 is displayed as the circular feature 808 in the image 800. Further, because the nosecone 105 is made of a clear material, the vessel tissue 806 can be imaged even through the nosecone 105. As can be seen in image 800, a 180 degree view of the tissue 806 can thus be obtained. The circular artifact 803 in the image (and here, the radial line 801) correspond to a guidewire and/or guidewire channel running alongside the nosecone 105.

In contrast to image 800, FIG. 9A shows a panoramic image 900 of a surrounding vessel when the cutter 103 is in the passive position and the nosecone 105 is closed, as shown in FIG. 9B. A 180 degree view of the vessel tissue 906 is shown on the right side of the image (taken through window 107) while the closed nosecone 909 is shown on the left side of the image (the lines 909a,b correspond to the bushing wall). The space 913 between the lines 909a,b through which tissue 906 can be seen on the left side of the image is taken through the additional window 307 in the bushing. Further, the distance between the arrows in image 900 indicates that the distal tip is "closed" (and close therefore close to the midline of the catheter).

Figure 10A:
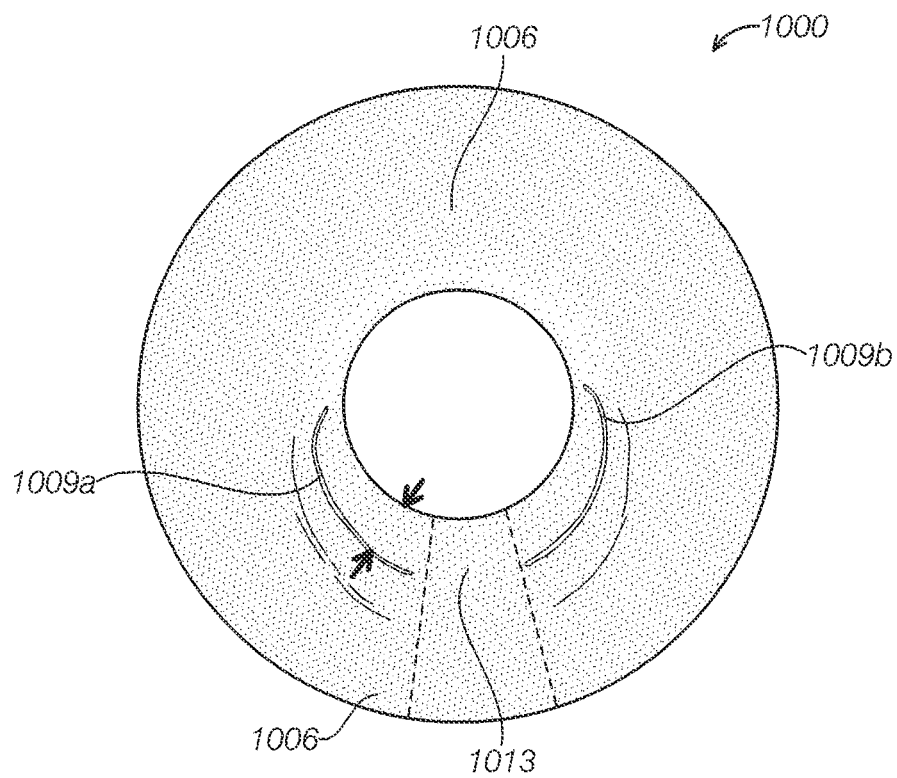
FIG. 10A shows a panoramic OCT image of a blood vessel taken with an atherectomy catheter through cutting window(s) when the nosecone is open, as identified by the arrow in FIG. 10B.
Figure 10B:
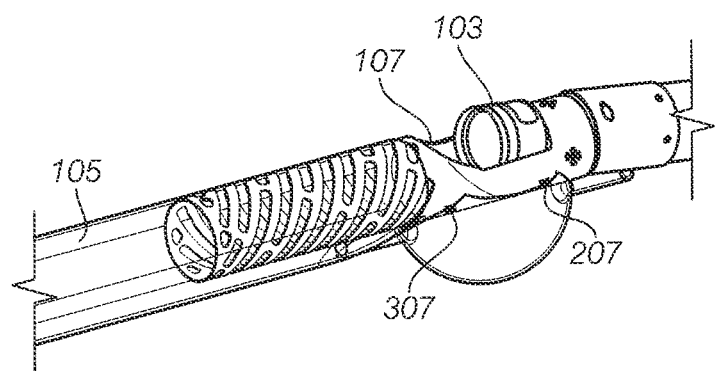

Finally, in contrast to image 900, FIG. 10A shows a panoramic image 1000 of a surrounding vessel when the cutter 103 is in the cutting position and the nosecone 105 is open, as shown in FIG. 10B. The vessel tissue 1006 (taken through window 107) is shown on the right side of the image while the closed nosecone 1009 is shown on the left side of the image (the lines 1009a,b correspond to the bushing wall). The space 1013 between the lines 1009a,b through which tissue 1006 can be seen is taken through the window 207. A comparison of the relative distance between the arrows in FIGS. 9A and 10A shows an increased distance between the catheter body and the nosecone, thereby suggesting to the operator that the nosecone 105 is in an open position. Further, in some embodiments, when the nosecone is open or closed, the image resulting from the window 207/307 will look different due to the angle change between the windows 207/307 and the imaging element 297 and/or the different shape of the windows 207/307.

In one embodiment, the atherectomy catheter 100 (or 200 or 400) includes a flush port close to the cutter 103. The flush port can be used to deliver flushing fluid to the region of imaging, thereby improving image quality. In some embodiments, the flushing can be activated through a mechanism on the handle of the device. The fluid can, for example, be flushed in the annular space between the catheter body 101 and the driveshaft 113. Further, in embodiments with jet channels in the bushing, the annular space can connect to the jet channels to provide fluid thereto.

Figure 6:
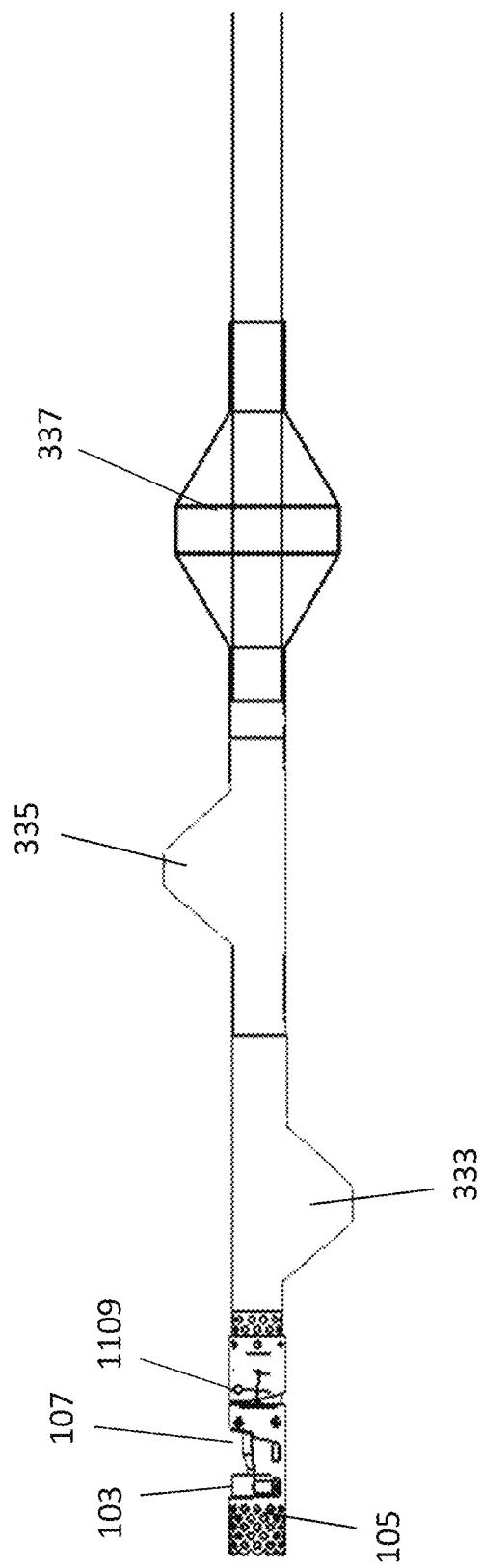
FIG. 6 shows one variation of a distal end of an atherectomy having a plurality of balloons that are arranged and may be used to provide a mechanical advantage in driving the cutting edge against the vessel wall.

Referring to FIG. 6, in some embodiments, the atherectomy catheters 100, 200, 400 can further include one or more eccentric balloons configured to help urge the cutter 103 into the tissue. In one embodiment (shown in FIG. 6), the catheter includes two eccentric balloons 333, 335. The first eccentric balloon 333, the distal-most balloon, can be positioned proximate to (overlapping with, just proximal of, or just distal of) the hinge point 1109. Further, the first balloon 333 can be biased to expand on the side of the catheter that is opposite to the cutting window 3107. The balloon 333 can urge the cutter 103 against the tissue by deflecting the cutter 103 up (relative to the position shown in FIG. 6) and into the tissue. The second eccentric balloon 335, proximal to the distal balloon 333, can be biased to expand on the on the same side of the catheter 100 as the cutting window 107. The second eccentric balloon 335 can further help drive the cutter 103 into the tissue by putting a downward force on a proximal portion of the catheter, resulting in an upwards force on the distal end of the catheter (e.g., due to torque from the relative position of the catheter and the balloon). In some embodiments, the first eccentric balloon 333 and/or the second eccentric balloon 335 can be annular. In some embodiments, the first and/or second eccentric balloons 333, 335 can help occlude the vessel, such as during imaging.

In some embodiments (and as shown in FIG. 6), a third balloon 337 can be used for occlusion. The third balloon 337 can be concentric with the shaft and can expand symmetrically therearound. In some embodiments, the third balloon 337 can be annular or spherical.

One or more of the balloons 333, 335, 337 can be configured so as to expand with little pressure, such as less than 5 psi, less than 4 psi, less than 3 psi, or less than 2 psi. This low pressure advantageously prevents the balloons 333, 335, 337 from pushing hard against the vessel wall, but still provides enough pressure to urge the cutter 103 into the tissue. The balloons 333, 335, 337 can further include tapered edges on the proximal and distal edges that allow the balloon to slide along the vessel and/or fit through tortuous regions.

In some embodiments, the balloons 333, 335, 337 can be compliant balloons. In other embodiments, the balloons 333, 335, 337 can be non-compliant. Further, the balloons 333, 335, 337 can have tapered proximal and distal ends to ease translation of the catheter through the vessel.

Figure 17A:
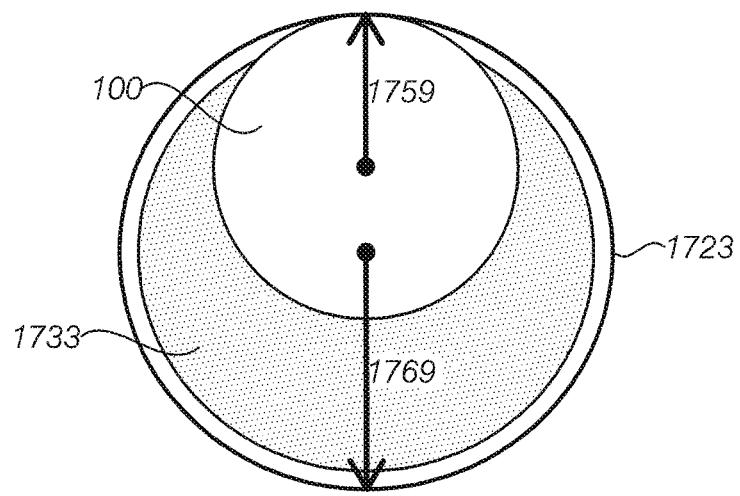
FIGS. 17A-17D show an atherectomy catheter with a C-shaped balloon.

Referring to FIGS. 17A-17D, in some embodiments, the atherectomy catheters 100, 200, 400 can include a C-shaped balloon 1733 configured to urge the cutter 103 into the tissue. The center of the balloon 1733 can be positioned substantially opposite to the blade of the cutter 103 and/or the cutting window of the atherectomy catheter 100 (or 200, 300). Referring to FIG. 17A, the balloon 1733 can have a C-shaped (e.g., crescent shape) when viewed down the axis of the catheter 100, i.e., can be wrapped around the catheter 100 so as to cover substantially the entire circumference of the catheter 100 except the cutter window or where the cutter 103 is exposed. The balloon, when inflated, may therefore form a kayak-like shape, with the distal and proximal end regions wrapping around the entire or substantially the entire circumference of a region of the nosecone (distal end of the balloon) and a region of the distal end of the elongate body at or proximal to the hinge region (proximal end of the balloon). By covering substantially the entire circumference of the catheter and/or nosecone, the ends of the balloon may cover cover more than 75% of the circumference of the catheter circumference, as shown in FIG. 17A (e.g., more than 80%, more than 85%, more than 90%, more than 95%, between 75-100%, between 80-100%, between 85-100%, between 90-100%, etc.). By using a balloon 1733 with such a shape, the gaps between the catheter 100 and the vessel 1723 are substantially reduced, advantageously negating or reducing the localized flushing required to displace blood from the visual field and improving cutter apposition. As is further shown in FIG. 17A, the radius of curvature 1769 of the expanded balloon 1733 is greater than the radius of curvature 1759 of the catheter 100 and/or the cutter. Again, this configuration both helps ensure that the substantially all of the exposed cutter 103 is pushed into the tissue and helps provide blood occlusion to increase the quality of the image.

In some embodiments, the balloon 1733 can be a compliant balloon. In other embodiments, the balloon 1733 can be non-compliant. Similar to as described above with respect to FIG. 6, the balloon 1733 can have a low inflation pressure, such as less than 5 psi, less than 4 psi, less than 3 psi, or less than 2 psi. Further, the balloon 1733 can have an expanded diameter of between 1 mm and 8 mm, such as between 2 mm and 7 mm or between 2 mm and 6 mm.

Figure 17B:
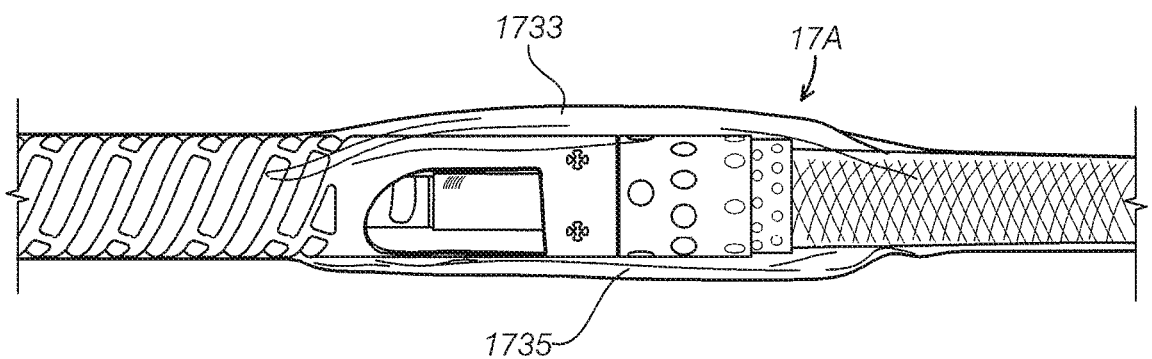
Figure 17C:
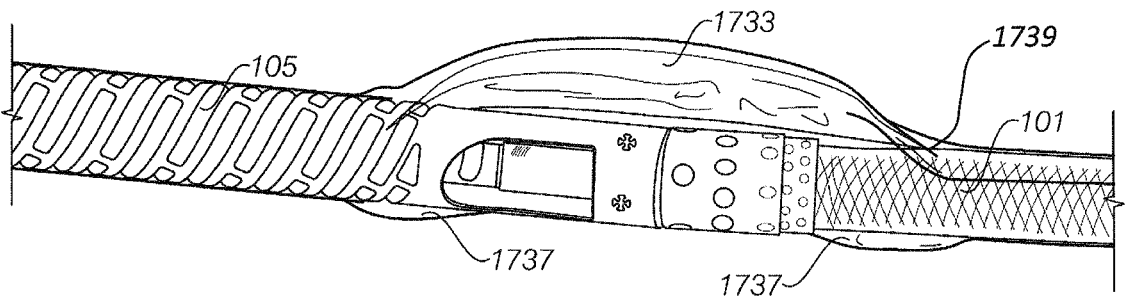
Figure 17D:
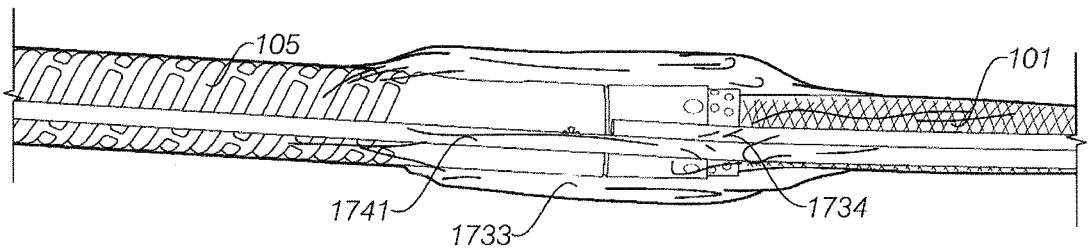

In one embodiment, to create the C shape, the balloon 1733 includes wide necks at both ends that are then wrapped around the nosecone 105 and elongate body 101 such that they cover at least half of the circumferential surface. FIG. 17B shows the wrapped balloon edges 1735 while FIG. 17C shows the wide necks 1737 fused at both ends. FIG. 17C shows an inflation port 1739 contained inside the balloon 1733 as well as a guidewire lumen 1741 that spans the length of the balloon 1733. In some embodiments, the balloon 1733 can be used to open or close the nosecone without requiring proximal or distal movement of the driveshaft.

In some embodiments, the C-shaped balloon 1733 can be configured to both urge the cutter 103 into the tissue and occlude blood flow to improve imaging. In other embodiments, the C-shaped balloon 1733 can be used only to urge the cutter 103 into the tissue. Optionally, one or more additional balloons can be used for occlusion of blood flow.

For example, another occlusion balloon, such as one of the balloons 333, 335, 337 described above, can be placed less than 2 inches from the balloon 1733, such as approximately 1.5 inches away, in order to occlude blood flow and improve imaging.

Additional balloon configurations are shown in FIGS. 18A-20B. Any of the balloons shown can be used in addition to, or instead of, any of the balloons described with respect to FIGS. 6 and 17A-17D.

FIGS. 18A-18C show an atherectomy catheter 1800, which can have features similar to any of the other atherectomy catheters described herein. The catheter 1800 includes a distal balloon 1833 and a proximal balloon 1835. The distal balloon 1833 is positioned opposite to the cutter 1803 and is biased to expand away from the cutter 1803 so as push the cutter 1803 into the vessel. The proximal balloon 1835 is annular and is configured to expand to occlude blood flow and improve imaging.

As shown in FIGS. 18A-18C, in some embodiments, the amount of inflation of one or more of the balloons can be varied. For example, as shown in FIG. 18A, the proximal balloon 1835 can be inflated fully while the distal balloon 1833 is deflated. In contrast, in FIG. 18B, the distal balloon 1833 can be fully inflated (thereby fully opening the nosecone 3807) while the proximal balloon 1835 can be deflated. Finally, as shown in FIG. 18C, one or both (here both) of the balloons 1833, 1835 can be partially inflated, for example for use in a small vessel.

Figure 19:
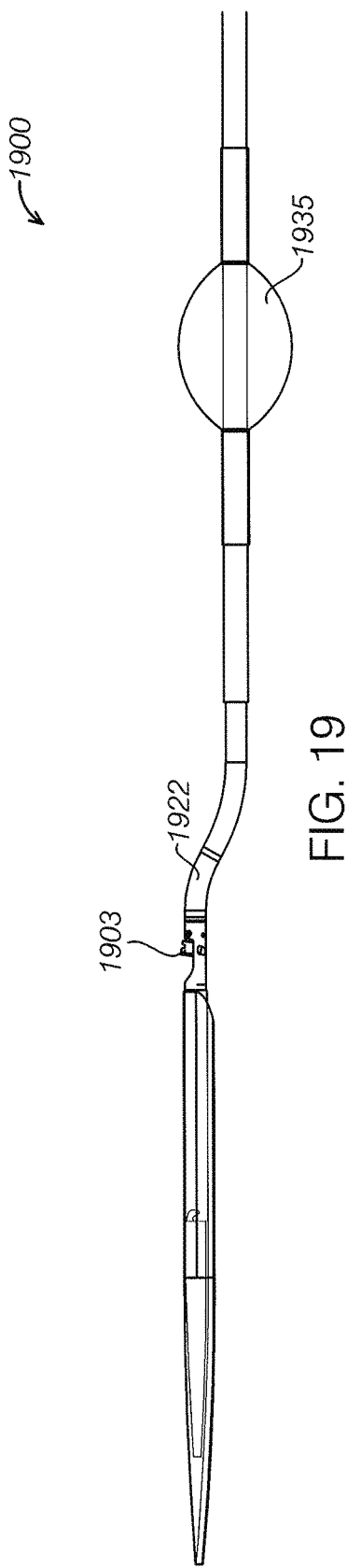
FIG. 19 shows an embodiment of an atherectomy catheter having a distal jog and a proximal concentric balloon.

FIG. 19 shows a catheter 1900 with a jog 3922 or fixed bend in the catheter to help with apposition of the cutter 1903 rather than a distal apposition balloon. A concentric proximal occlusion balloon 1935 extends proximal to the jog 3922.

FIGS. 20A and 20B shows a catheter 2000 with a jog 2022 or fixed bend and an eccentric occlusion balloon 2035. The eccentric occlusion balloon 2035, when inflated to the biased shape, can advantageously both provide occlusion of blood flow and help push the jog, and thus the cutter 2003, against the vessel wall.

Figure 21A:
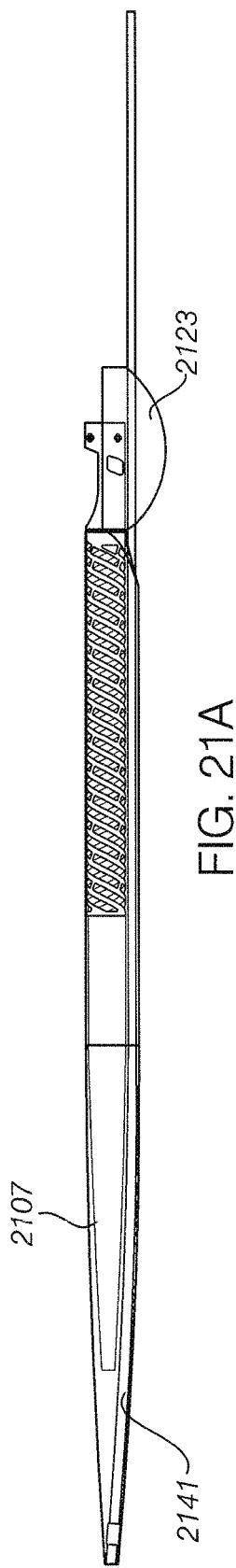
FIGS. 21A and 21B show an embodiment of an atherectomy catheter with a guidewire lumen extending through a balloon.
Figure 21B:
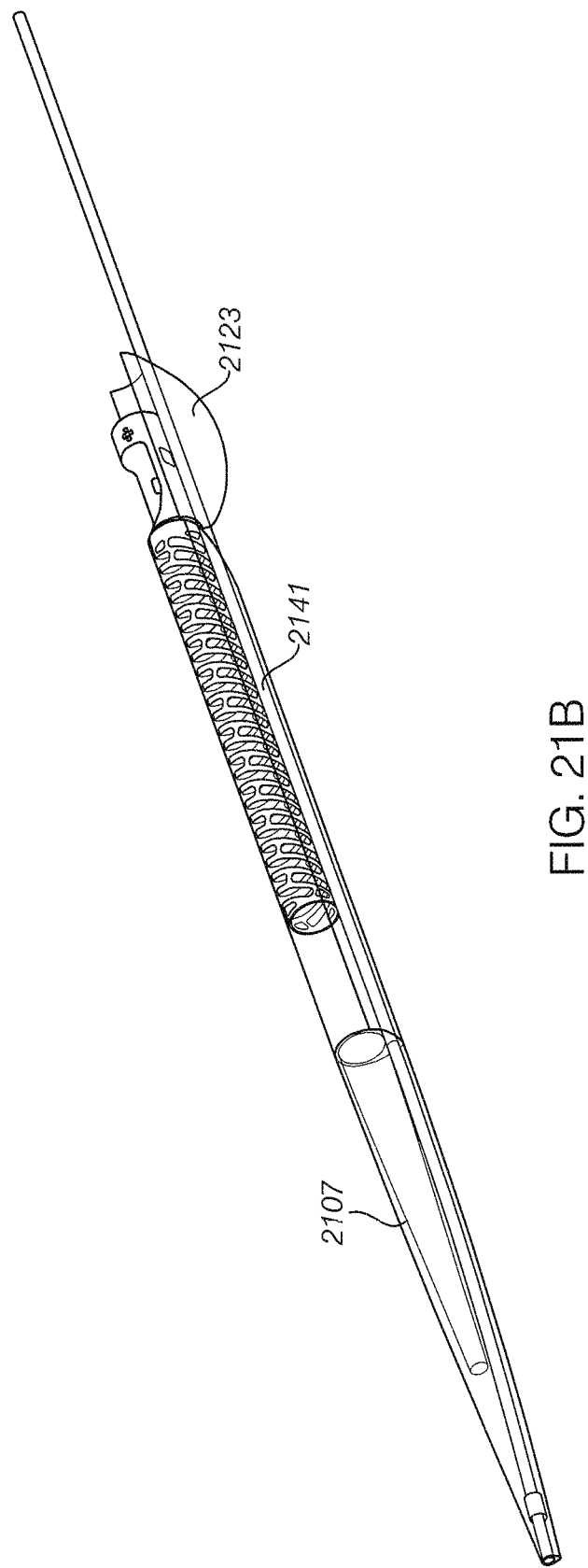

The catheters described herein can further include a guidewire lumen extending the length of the catheter. Referring to FIGS. 21A and 21B, a guidewire lumen 2141 can extend through one or more balloons (such as apposition balloon 2123 shown in FIGS. 229A and 21B) and through the distal tip 2107 or nosecone. As shown in FIGS. 21A and 21B, the guidewire lumen 2141 can extend along a side of the catheter that is opposite to the cutter.

Figure 22:
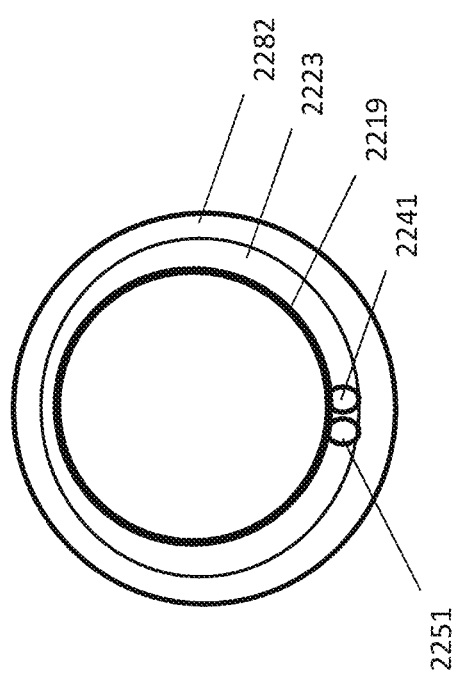
FIG. 22 shows a cross section of an exemplary atherectomy catheter.
Figure 24F:
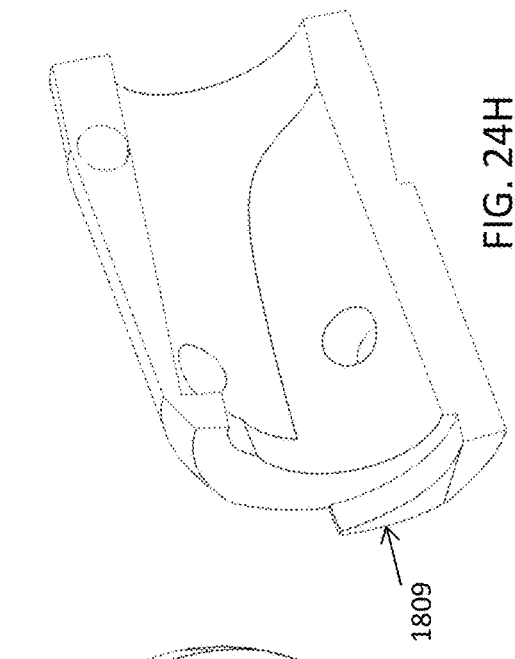
FIGS. 24F and 24G are back and sectional views (taken through the midline of the long axis, G' in FIG. 24D), respectively.
Figure 24H:
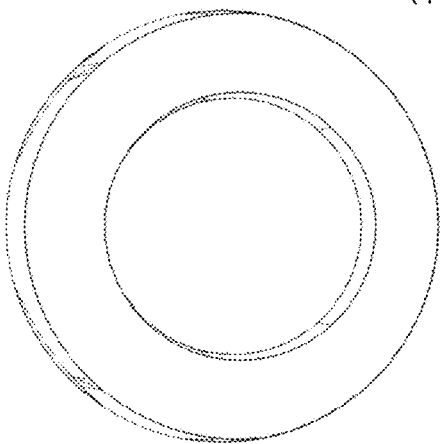
FIG. 24H is a perspective view of the sectional view shown in FIG. 24G.
Figure 24E:
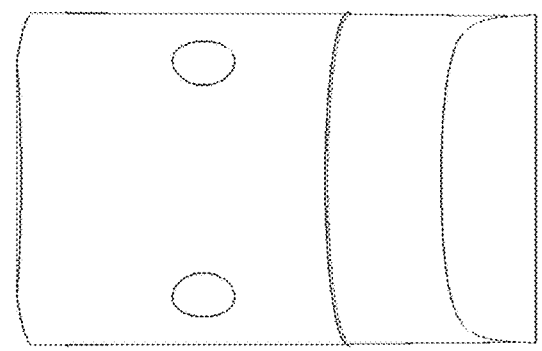
Figure 24G:
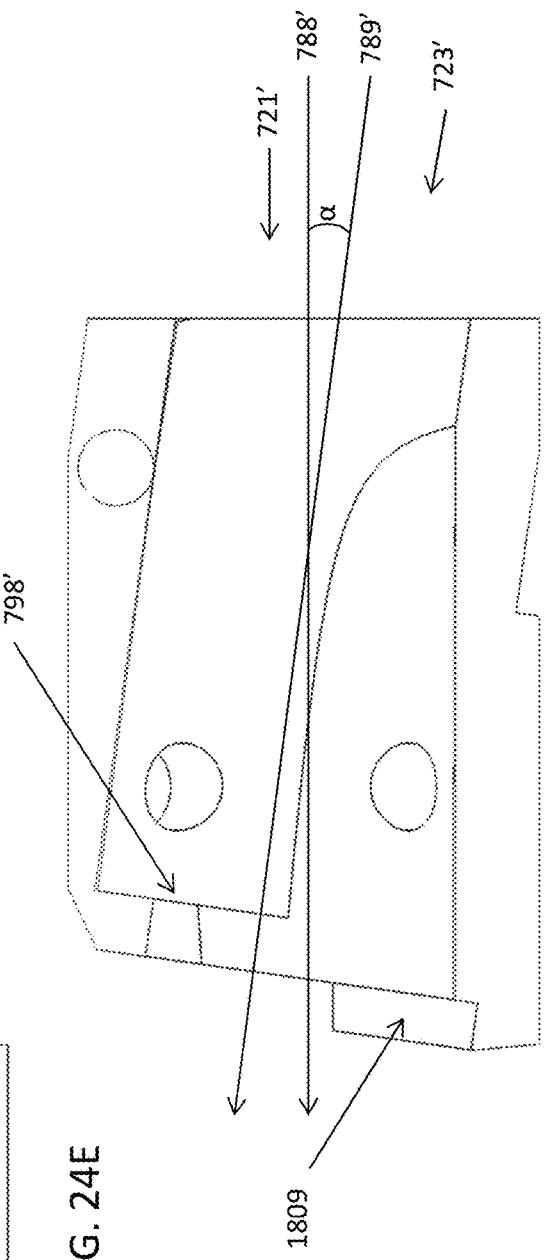

Referring to FIG. 22, in some embodiments, the guidewire lumen 2241 is fused to the torque shaft 2219 with a laminate layer 2223, such as a polyether block amide (e.g., Pebax®) layer. A balloon 2282 (such as a distal occlusion balloon) can then extend around the laminate layer 2223. Advantageously, the balloon 2282 can seal against the smooth laminate layer 2223, thereby preventing leaking that might otherwise occur when the balloon seals directly against the guidewire lumen. The balloon 2282 can be an occlusion balloon and/or an apposition balloon. In some embodiments, such as for apposition, the balloon 2282 extends only partially around the laminate layer 2223 to make a crescent shape.

Referring still to FIG. 22, the catheters described herein can further include an inflation lumen 2251 running from the proximal end (for attachment to a gas or inflation fluid source) to the distal-most balloon. As shown in FIG. 22, the inflation lumen 2251 can also be underneath the laminate layer 2223. Referring to FIGS. 23A and 23B, the inflation lumen 2251 can extend proximate to, and parallel with, the guidewire lumen 2241. The inflation lumen 2251 can terminate in the distal-most balloon 2223 while the guidewire can extend through the balloon 2223 and along the distal tip 2207. In some embodiments, a single inflation lumen can be used to inflate more than one balloon. The inflation lumen can thus pass through the proximal balloon(s), provide an opening (such as a hole or slit) thereto for inflation and terminate at the distal-most balloon. In embodiments where the inflation lumen is used to fill more than one balloon, the compliancy and/or elasticity of the balloons can be selected such that the balloons inflate in the desired sequence. For example, referring to FIGS. 18A-18C, the proximal balloon 1835 can be more compliant or elastic than the distal balloon 1833. As such, the proximal balloon 1835 will inflate before the distal balloon 1833, providing occlusion (and therefore imaging) before apposition (and cutting).

In use, all of the balloons described herein for use with the atherectomy catheters can be fully inflated both while the cutter is rotated and while the catheter is translated distally (e.g., to move to a new location and/or to cut long strips of tissue). That is, because the balloons can have tapered proximal and/or distal ends, can be compliant, and and/or can have a low inflation pressure, the balloons can easily move along the vessel when inflated while still providing the desired apposition and/or occlusive effects.

Figure 5A:
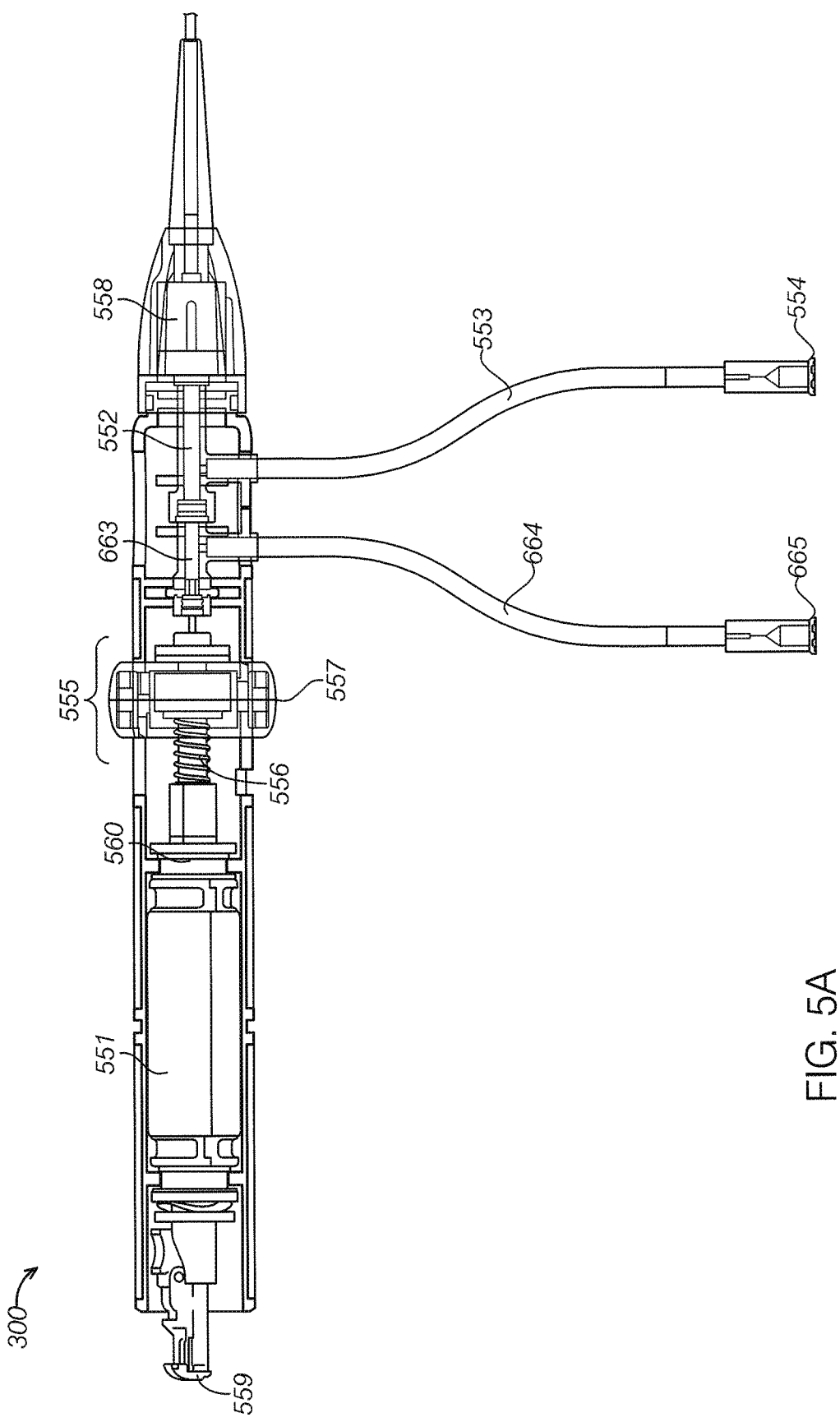

Referring to FIG. 5A, a handle 300 can be used to control the rotation or translation of the driveshaft for the catheter 100, 200, or 400. The handle 300 can advantageously allow the optical fiber to move distally and proximally with the cutter as it is driven without requiring the fiber to move at a proximal location, e.g., without requiring movement of the optical fiber assembly within the drive assembly. Thus, the handle 300 can be design to completely account for movement of the drive shaft. An exemplary driveshaft management system 555 is shown in FIG. 5. The driveshaft management system 555 allows the user to position the driveshaft distally or proximally as the driveshaft is simultaneously spinning at a high speed. In some embodiments, the driveshaft can be configured such that it is fully tensioned before the driveshaft management system 555 is positioned at its most proximal position. That is, the driveshaft management system 555 can include a driveshaft tensioning spring 556. The spring 556 can be configured such that, as the user positions the slideable user ring 557 (or button) proximally, the driveshaft is fully tensioned and the driveshaft management system 555 is moved proximally, causing the spring 556 to compress and apply a controlled tensile load on the driveshaft. This fiber management system 555 advantageously enhances performance of the catheter by tensioning the driveshaft with a pre-determined load to properly position the cutting and imaging component against the bushing at the distal end of the catheter, improving cutting and imaging of the catheter.

The driveshaft management system 555 can transmit torque originating from a drive assembly, as described further below. Connection to the drive assembly can be made at the optical connector 559. Torque can thus be transmitted from the optical connector 559, through the fiber cradle 551, to the drive key 560, through the driveshaft management system 555, and then directly to the catheter driveshaft, all of which can rotate in conjunction. The fiber cradle 551 can include a set of components (i.e., a pair of pieces to make the whole fiber cradle) that houses the proximal end of the optical fiber and transmits torque within the driveshaft system. The fiber cradle components can be thin-walled by design, thereby creating a hollow space inside. Within this hollow space of the fiber cradle 551, the optical fiber can be inserted or withdrawn as the device driveshaft is positioned proximally or distally. As the fiber is inserted into the fiber cradle 551 when the user ring 557 is positioned proximally, the fiber is able to coil within the internal space of the fiber cradle 551 while maintaining imaging throughout its length to the distal tip. Conversely, as the fiber is withdrawn from the fiber cradle 551 when the user ring 557 is positioned distally, the coiled section of fiber is able to straighten while maintaining imaging throughout its length to the distal tip.

Figure 5B:
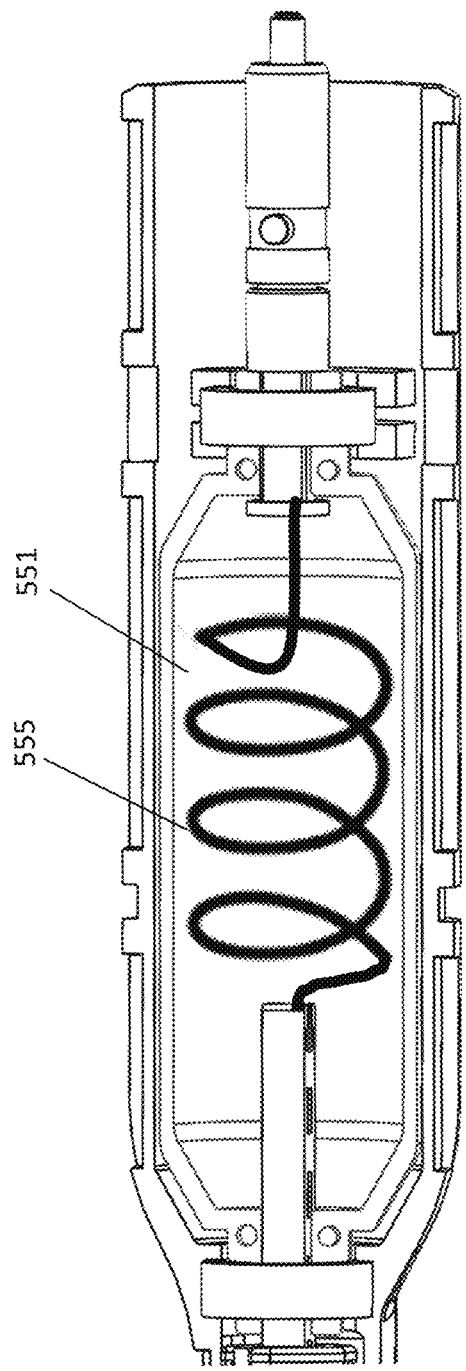
Figure 5C:
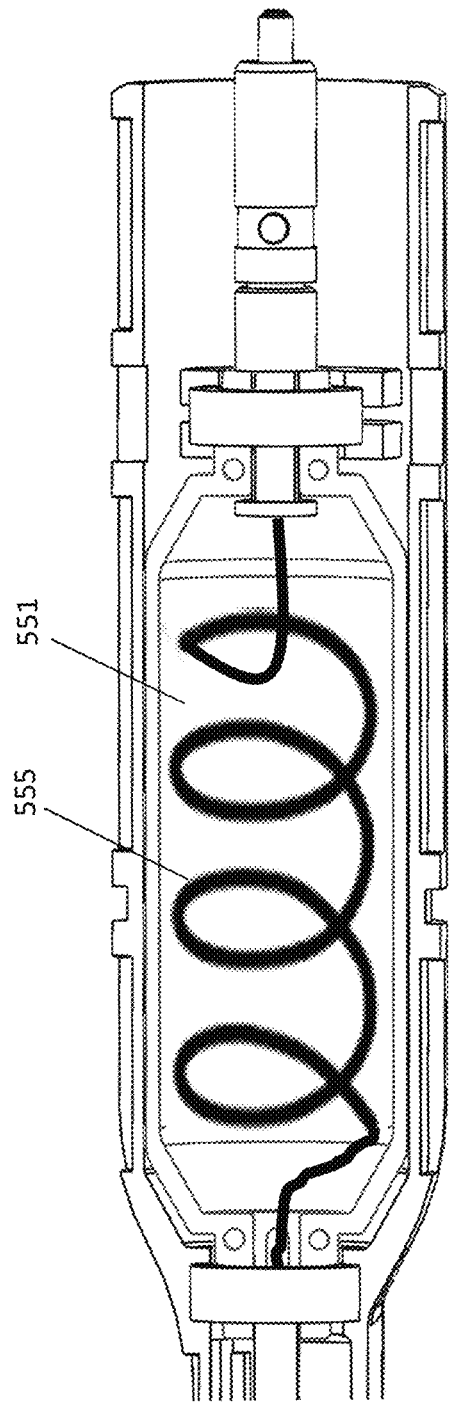
Figure 5F:
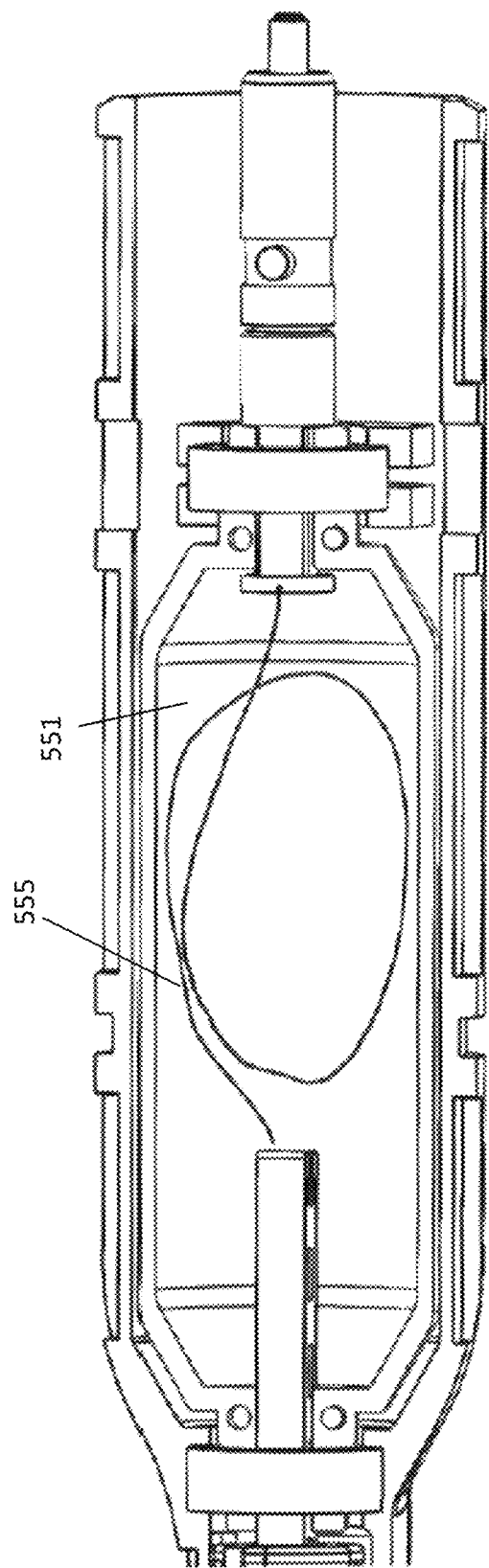
Figure 5G:
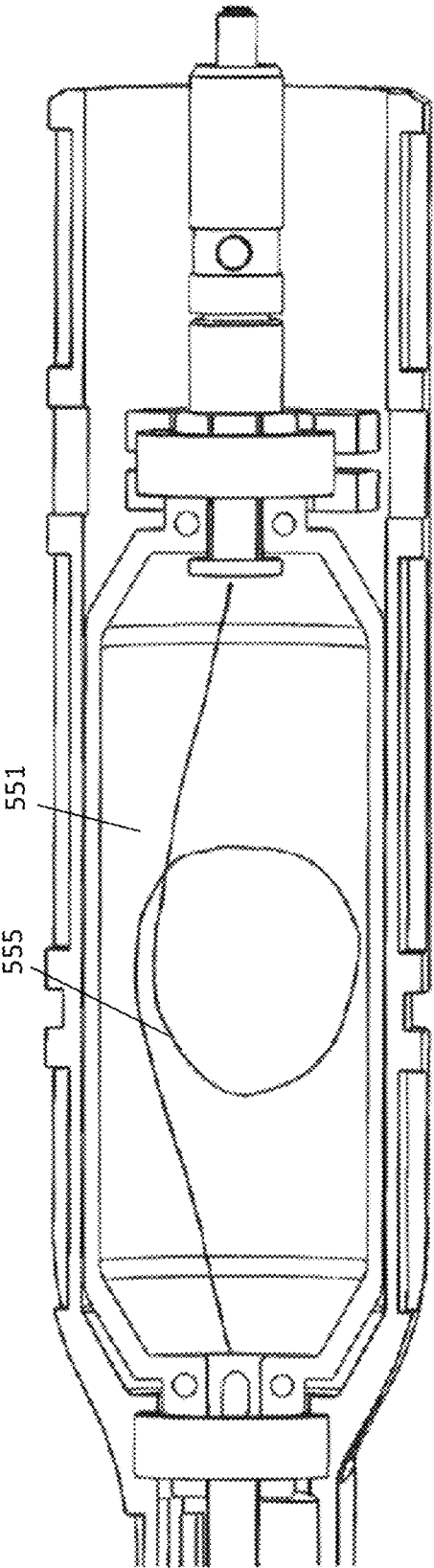

FIGS. 5B and 5C show the interior of the fiber cradle 551 with a fiber 555 extending therethrough. In this embodiment, the fiber 555 is spiraled around the longitudinal axis of the cradle along the inner diameter of the cradle 551. As shown in the transition from FIG. 5B to FIG. 5C, when the fiber 555 is withdrawn from the cradle 551, it will at least partially uncoil (e.g., the coil can become less tight). FIGS. 5D and 5E show an alternative embodiment of the interior of the fiber cradle 551 with the fiber 555 extending therethrough. In this embodiment, the fiber 555 is looped longitudinally along the inner diameter of the cradle. As shown in the transition from FIG. 5D to FIG. 5E, when the fiber 555 is withdrawn from the cradle, the loop is pulled tighter within the central portion of the cradle 551. FIGS. 5F and 5G show a similar embodiment as FIGS. 5D and 5E in which the fiber 555 forms a longitudinal loop within the cradle 551 and pulls tight when the fiber is withdrawn. In some embodiments, the cradle 551 can have a length of 1-2 inches, such as approximately 1.5 inches. With these dimensions, the fiber 555 (and thus the cutter and driveshaft) can extend up to 3 inches, up to 2.5 inches, up to 2 inches, or up to 1.5 inches. In some embodiments, a tolerance is built in such that the fiber 555 is able to extend further than the driveshaft moves. For example, the fiber can be designed to travel up to 2 inches, but the driveshaft can move only ¾ inches. This coiling and uncoiling or looping and tightening design feature advantageously provides more fiber capacity or "slack" to the overall driveshaft system to increase the range in which the driveshaft system can be translated.

The handle 300 can further include a balloon inflation chamber 552 configured to connect to a balloon inflation lumen (e.g., for use with a balloon on the catheter as described above) on one side and to balloon inflation tubing 553 and/or a port 554 on the other side. Because the inflation fluid transfers to the balloon through the balloon inflation chamber 552, the outer shaft 111 can advantageously rotate (e.g., by rotating the knob 558) independently of the balloon inflation chamber 552, allowing the tubing 553 and/or port 554 to remain stationary during rotation of the outer shaft 111.

Moreover, as shown in FIG. 5, the handle 300 can further include a catheter flush chamber 663 and catheter flush tubing 664 and/or flush port 665 to provide flushing through the catheter, as described above.

The catheters described herein can be driven using a drive assembly. Exemplary drive assemblies are described in Patent Applications: PCT Application No. PCT/US2013/032089, titled "ATHERECTOMY CATHETER DRIVE ASSEMBLIES," filed Mar. 15, 2013, Publication No. WO 2013/172974, and U.S. patent application Ser. No. 13/654,357, titled "ATHERECTOMY CATHETERS AND NON-CONTACT ACTUATION MECHANISM FOR CATHETERS," filed Oct. 17, 2012, Publication No. US-2013-0096589-A1, both of which are herein incorporated by reference in their entireties.

Figure 13A:
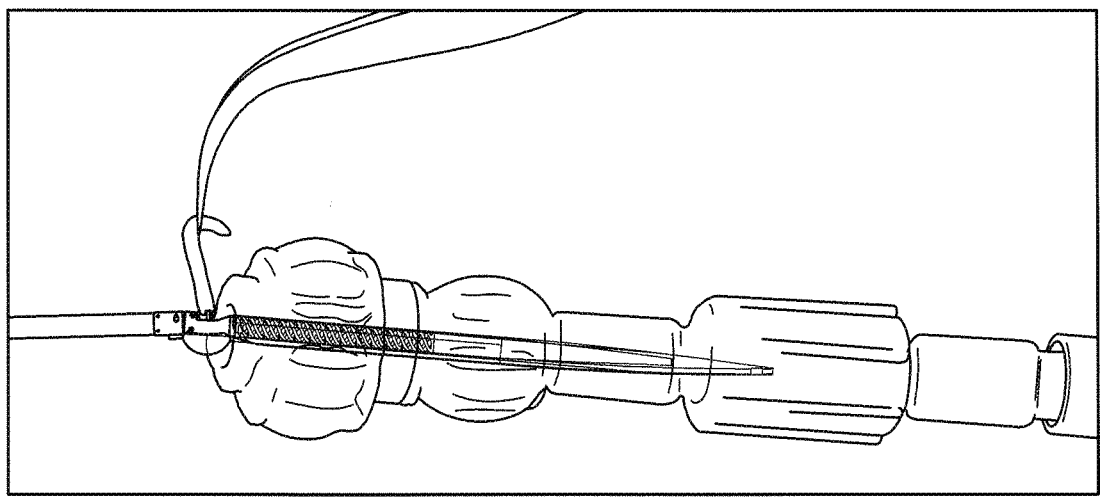
FIG. 13A shows the removal of a single, long strip of material cut from the tissue by an atherectomy catheter as described herein.
Figure 13B:
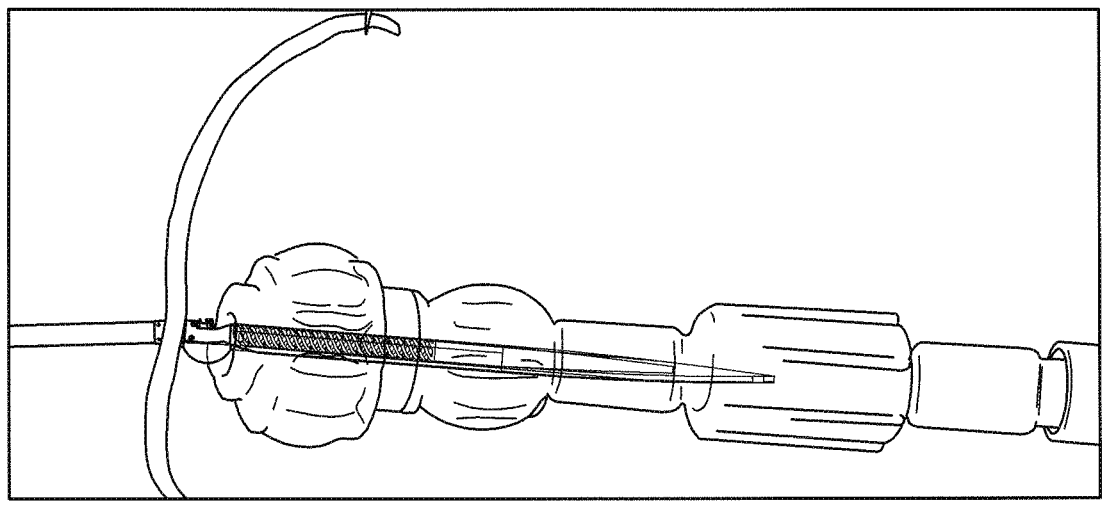
FIGS. 13B and 13C show the length of tissue removed.
Figure 13C:
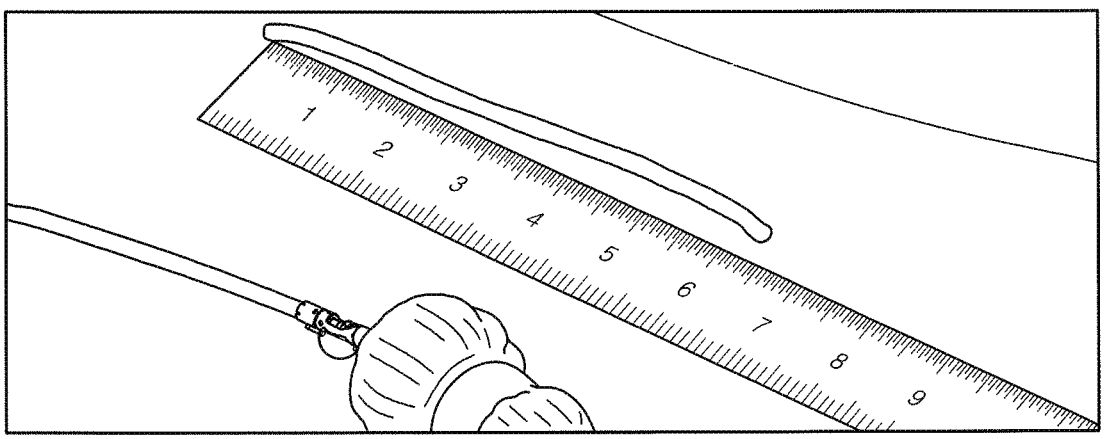

Advantageously, the atherectomy catheters 100, 200, 400 described herein can be used to remove strips of tissue. FIG. 13A shows the removal of a single, long strip of material cut from the tissue by an atherectomy catheter as described herein. FIGS. 13B and 13C show the length of tissue (weighting 70.4 mg) removed.

The atherectomy catheters described herein may additionally include any of the features described in the following co-pending applications: PCT Application No. PCT/US2013/031901, titled "ATHERECTOMY CATHERES WITH IMAGING," filed Mar. 15, 2013, Publication No. WO 2013/172970, and PCT Application No. PCT/US2013/032494, titled "BALLOON ATHERECTOMY CATHERS WITH IMAGING," filed Mar. 15, 2013, Publication No. WO 2014/039099, both of which are herein incorporated by reference in their entireties.

FIGS. 29A-33F and 41A-42 show examples of atherectomy devices and handles having drive and imaging shafts that are separated from one another at the distal end and translatable relative to one another. FIGS. 29A-33F and 41A-42 also have cutters that are configured to be urged against the vessel wall with an inflatable element without using a separate hinge mechanism.

Figure 29A:
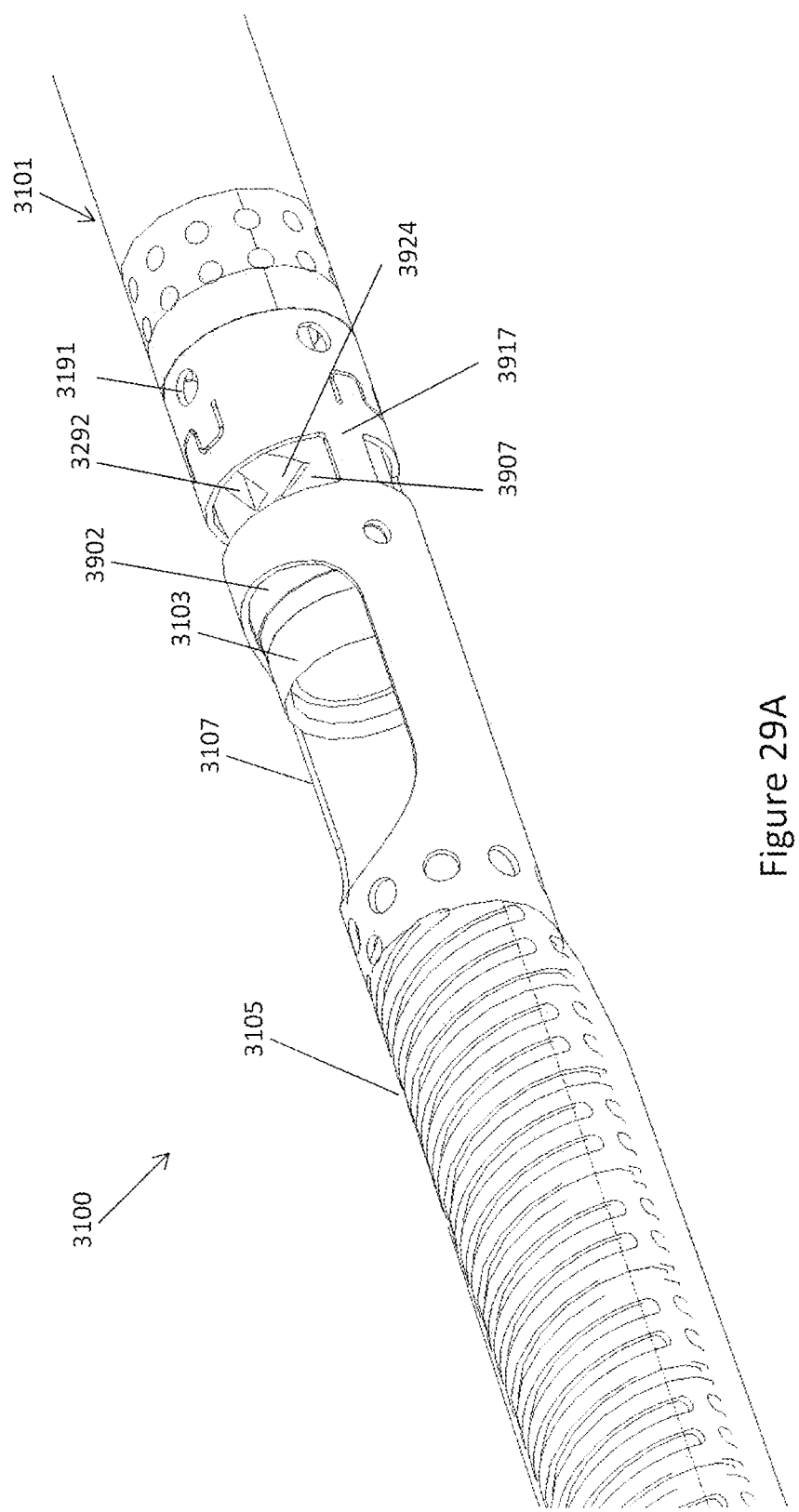
FIGS. 29A-29C show an atherectomy device having concentric drive and imaging shafts that are separated from one another at the distal end and axially translatable relative to one another.
Figure 29B:
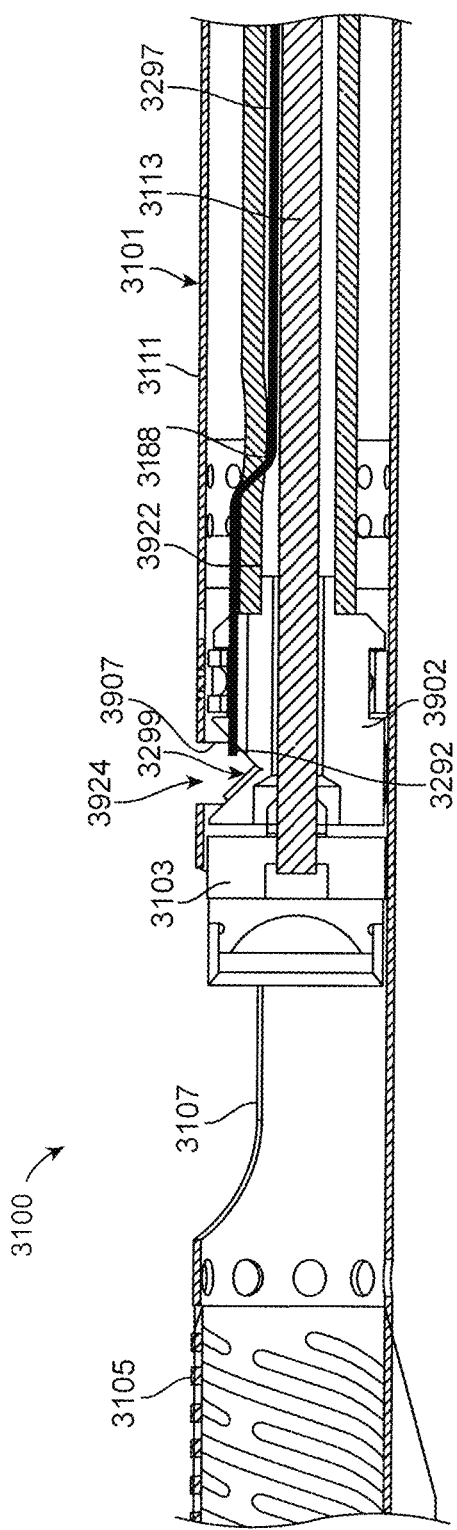
Figure 29C:
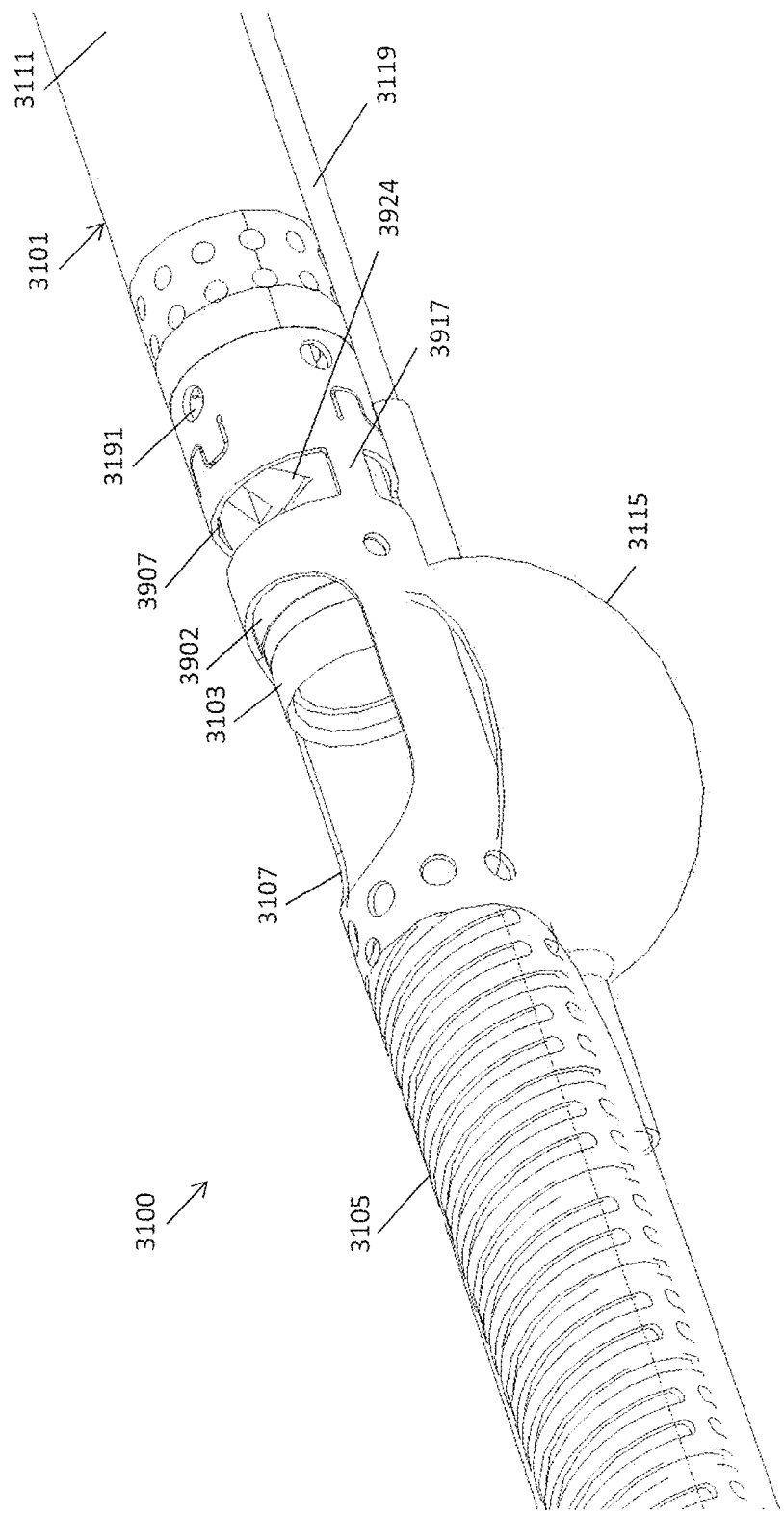

In one embodiment, referring to FIGS. 29A-29C, a catheter 3100 can include a catheter body 3101, a cutter 3103 extending from the distal end of the catheter body 3101, and an imaging collar 3902 near the distal end of the catheter body 3101 but proximal to the cutter 3103. A nosecone 3105 can extend from the distal end of the catheter body and around the cutter 3103 to store tissue removed by the cutter 3103. The nosecone 3105 can include a cutting window 3107 therein configured to expose a portion of the cutter 3103. The catheter 3100 can further include an inflatable element, such as a balloon 3115 (see FIG. 1C), configured to urge the cutter 3103 against the side of a vessel.

Referring to FIG. 29B, the catheter body 3101 can include an outer shaft 3111 and a drive shaft 3113 extending inside the outer shaft 3111. The outer shaft 3111 can be configured to be turned, such as turned manually, to position the cutter 3103 and/or the imaging collar 3902 toward the desired location. The drive shaft 3113 can extend through, and rotate relative to, the imaging collar 3902. Further, the drive shaft 3113 can be attached to the cutter 3103 to rotate the cutter 3103. Rotation of the cutter 3103 can provide cutting due to the rotational motion of the sharp distal cutting edge. The drive shaft 3113 can be rotated at up to 10,000 rpm, such as approximately 1,000 rpm to 5,000 rpm, e.g., 1,000 rpm, in a single direction, though rotation in both directions or at different speeds is possible.

Referring still to FIG. 29B, the catheter 3100 can further include an optical fiber 3297, the distal end of which can act as an imaging element 3292 for OCT imaging. The imaging collar 3902 can be attached to an imaging shaft 3922 that extends within the catheter body 3101 concentric with the drive shaft 3113. As shown in FIG. 29B, the concentric imaging shaft 3922 can extend between the drive shaft 3113 and the outer shaft 3111 (i.e. such that the drive shaft 3113 is in the center). In other embodiments (such as described below with respect to FIGS. 41A-41D), the drive shaft 3113 can extend between the concentric imaging shaft 3922 and the outer shaft 3111 (i.e. such that the imaging shaft 3922 is in the center). The rotation of the imaging shaft 3922 and the drive shaft 3113 can be decoupled from one another at the distal end of the device, thereby providing for separate rotation of the cutter 3103 and the imaging element 3292 (which can be the distal end of an optical fiber 3297). As described below, in some embodiments, the rotation of the imaging shaft 3922 and the drive shaft 3113 can be coupled at the proximal end (such as in the handle so as to be driven by the same motor) while remaining decoupled along the length of the catheter.

The outer shaft 3111 (or a housing connecting the outer shaft 3111 to the nosecone 3105) can include an imaging window 3907 through which the imaging element 3292 can be exposed. The imaging window 3907 can extend 360 degrees around the circumference of the outer shaft 3111, but can include structural struts 3917 extending thereacross to both provide structural support and act as imaging markers. The imaging window 3907 can further be used as a flush port to allow flush fluid to be delivered through the outer shaft 3111 and to the area of imaging, thereby improving image quality. In some embodiments, flush fluid can extend through fluid ports 33191 in the outer shaft 3111.

The optical fiber 3297 can run within the imaging shaft 3922 to provide the imaging (e.g., OCT) signal. As shown in FIG. 29B, the optical fiber 3297 can run between the inner diameter of the imaging shaft 3922 and the outer diameter of the drive shaft 3113 and can be free to flow therein. At distal point 3188, the fiber 3297 can cross to the outside of the imaging shaft 3922 to attach to the imaging collar 3902, such as in an opening 3924 in the imaging collar 3902. Leaving the optical fiber 3297 free to float within the imaging shaft 3922 for the majority of the length of the catheter body 3101 ensures that the fiber is not compressed or stretched as the catheter 3100 bends as it is advanced through tortuous anatomy. As described further below, the fiber 3297 can be rotated with the imaging shaft at both the proximal and distal ends of the fiber 3297. Accordingly, the fiber 3297 does not have to wrap around the drive shaft 3113 as it rotates, advantageously both reducing the likelihood of fiber breakage and allowing the imaging element and cutter to rotate in a single direction.

As shown in FIG. 29B, a reflective element 3299, such as a mirror, a polished pin, a film deposited on the surface of the imaging collar 3902, or a polished surface of the imaging collar 3902 itself, can further be located within the opening 3924 in the imaging collar 3902 to radially direct light from the optical fiber 3297 into the tissue. The reflective element 3299 can sit, for example, at a 35 degree to 55 degree angle, such as a 45 degree angle, relative to the central axis of the optical fiber 3297 so as to direct the light sideways into the tissue. The distal end of the optical fiber 3297 can be located less than 3 mm from the distal edge of the cutter 3103, such as less than 1.5 mm from the cutting edge, such as less than or equal to 1.2 mm, such as less than or equal to 1 mm. By having the imaging element 3292 close to the cutting edge, the resulting image can advantageously correlate with and depict the portions of the vessel being cut.

As shown in FIG. 29C, an inflatable element, such as a balloon 3115, can be located opposite to the cutting window 3107. Referring to FIG. 29C, the balloon 3115 can be attached to an inflation tube 3119, which can alongside or be embedded in the outer shaft 3111. The balloon 3115 can be attached at the distal end to the outer shaft 3111 (at a location just proximal to the imaging window 3907) and at the proximal end to the inflation tube 3119 inside the outer shaft 3111, such as through a hole in the outer shaft 3111. In some embodiments, the inflation tube 3119 can radially align with one or more of the struts 3917 so as to not hinder the resulting image. Inflation of the balloon can position or urge the cutting window 3107 and thus the cutter against the tissue. Further, the cutting window can be sized and dimensioned such that inflation of the balloon 3115 causes the tissue to invaginate within the cutting window, thereby improving the cutting quality of the device. Further, the cutting window can be sized such that it is smaller than the diameter of the cutter, thereby preventing the cutter from popping out as the cutting window and cutter are urged against the vessel wall. In one embodiment, the window 3107 can extend between 90 and 270 degrees around the circumference of the nosecone or catheter, such as 150 to 210 degrees, such as between 175 and 180 degrees. Having a window 3107 of these dimensions, such as that extends 175 and 180 degrees around the circumference of the nosecone or catheter, can advantageously provide significant tissue capture upon inflation of the balloon 3115 while still providing adequate stiffness to the nosecone or catheter.

The catheter 3100 can further include a mechanism for packing tissue into the nosecone 3105, such as by moving the drive shaft 3113 and cutter 3103 axially such that tissue can be urged by the distal surface of the cutter 3103. Advantageously, the drive shaft 3113 can be moved axially without movement of the imaging shaft 3922, thereby allowing for packing of the tissue without disrupting the imaging.

Advantageously, by having an imaging shaft that is separate or decoupled from the drive shaft at their respective distal ends, the rotation of the cutter and the optical fiber can be mechanically isolated from one another (i.e., such that a mechanical action or reaction of one does not affect the other). For example, if the cutter stalls during rotation, such as when it hits a hard piece of tissue, the mechanically isolated imaging element can remain unaffected and continue rotating at the same constant speed. Such continuous rotation of the imaging element reduces or eliminates rotational distortion, such as nonuniform rotational distortion (NURD), thereby improving imaging quality.

Further, by having separate imaging and drive shafts, the drive shaft can advantageously be used to pack tissue while maintaining the imaging element in the same location, thereby ensuring that the imaging location is constant and well known. Moreover, by having separate imaging and drive shafts, the fluid flush can be delivered close to the imaging element even when the drive shaft is moved distally to pack tissue.

Further, by using the balloon 3115 of catheter 3100 to urge the cutter against the vessel wall and by having an optimally designed cutting window, tissue can be pressed into the cutting window and cut, thereby improving cutting quality without requiring an articulation mechanism in the catheter. Further, the balloon 3115 can advantageously act as an occlusion element to restrict blood flow to the imaging element 3292, thereby reducing the amount of saline flush required to obtain a clear image and improving image quality.

As noted above, in some embodiments, the drive shaft 3113 and imaging shaft 3922 can be unconnected at the distal end of the catheter to allow for separate imaging and cutting but connected at the proximal end of the catheter so that they can be rotated from the same source, such as the same drive system. Although the shafts can be connected at the proximal end of the cutter, rotational distortion can still be avoided because the rotating motor can be strong enough to spin at the same speed regardless of the resistance to rotation placed on the cutter at the distal end. Accordingly, even if the drive shaft slows down due to stalling, the imaging shaft can continue to rotate at the same constant input speed.

Referring to FIGS. 30A-30D, the catheter 3100 can be used with a handle 3200 configured such that the drive shaft 3113 and the imaging shaft 3922 can be rotated separately at the distal end of the catheter while being rotated with the same source at the proximal end of the catheter. Rotation with the same source can advantageously requires only one motor (reducing the size and complexity of the device), allows for the fiber to stay on the centerline of the catheter and handle, and can provide the same relative speed for zero relative speed between the imaging and drive shafts in aid in preserving imaging fiber integrity. As described further below, the handle 3200 can further include a mechanism that allows for axial translation of the drive shaft 3113 (e.g., to pack tissue with the cutter), but maintains the fixed position of the imaging shaft 3922. Further, the handle 3200 can be configured to as to allow free rotation of the fiber 3297 therein such that minimal or no fiber management and/or wrapping of the fiber is necessary.

Figure 30A:
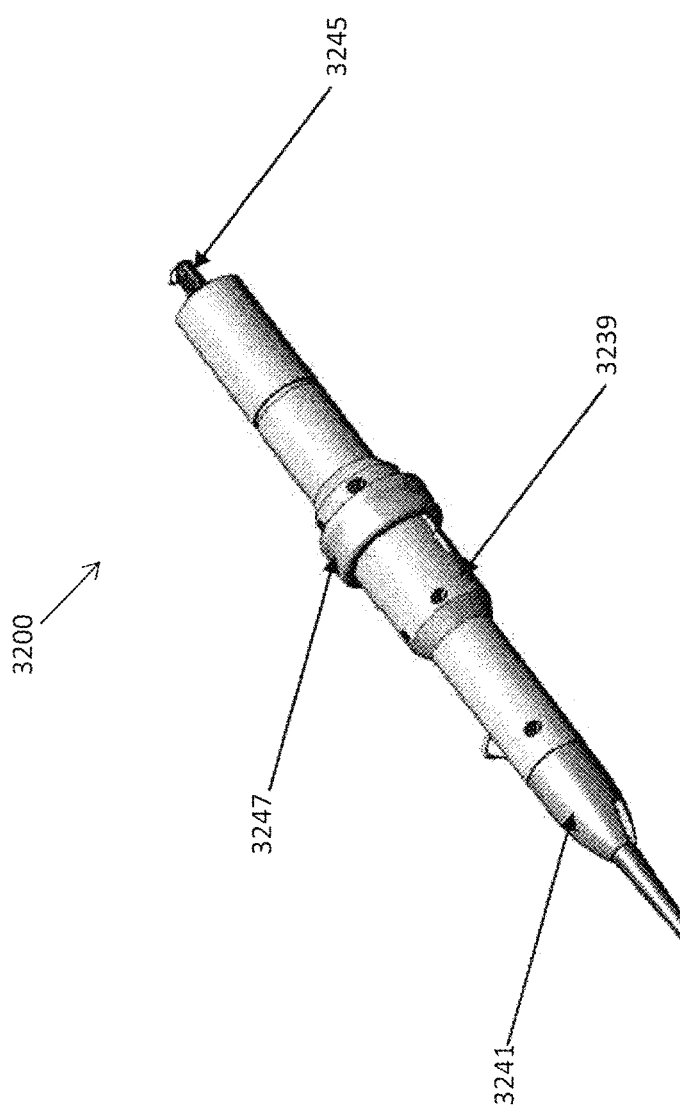

Referring to FIG. 30A, the handle 3200 can include an outer shell 3239, a handle tip 3241 configured to connect to the outer shaft 3111 of the catheter 3100, and an optical connector 3245 configured to engage with a drive system and light source. The handle 3200 can further include a handle ring 3247 configured to slide along the handle 3200 to translate the drive shaft 3113 axially. The handle tip 3241 can be configured to rotate relative to the rest of the handle 3200 to allow the user to torque the outer shaft 3111 to orient the distal tip of the catheter 3100 in the desired position.

Figure 30B:
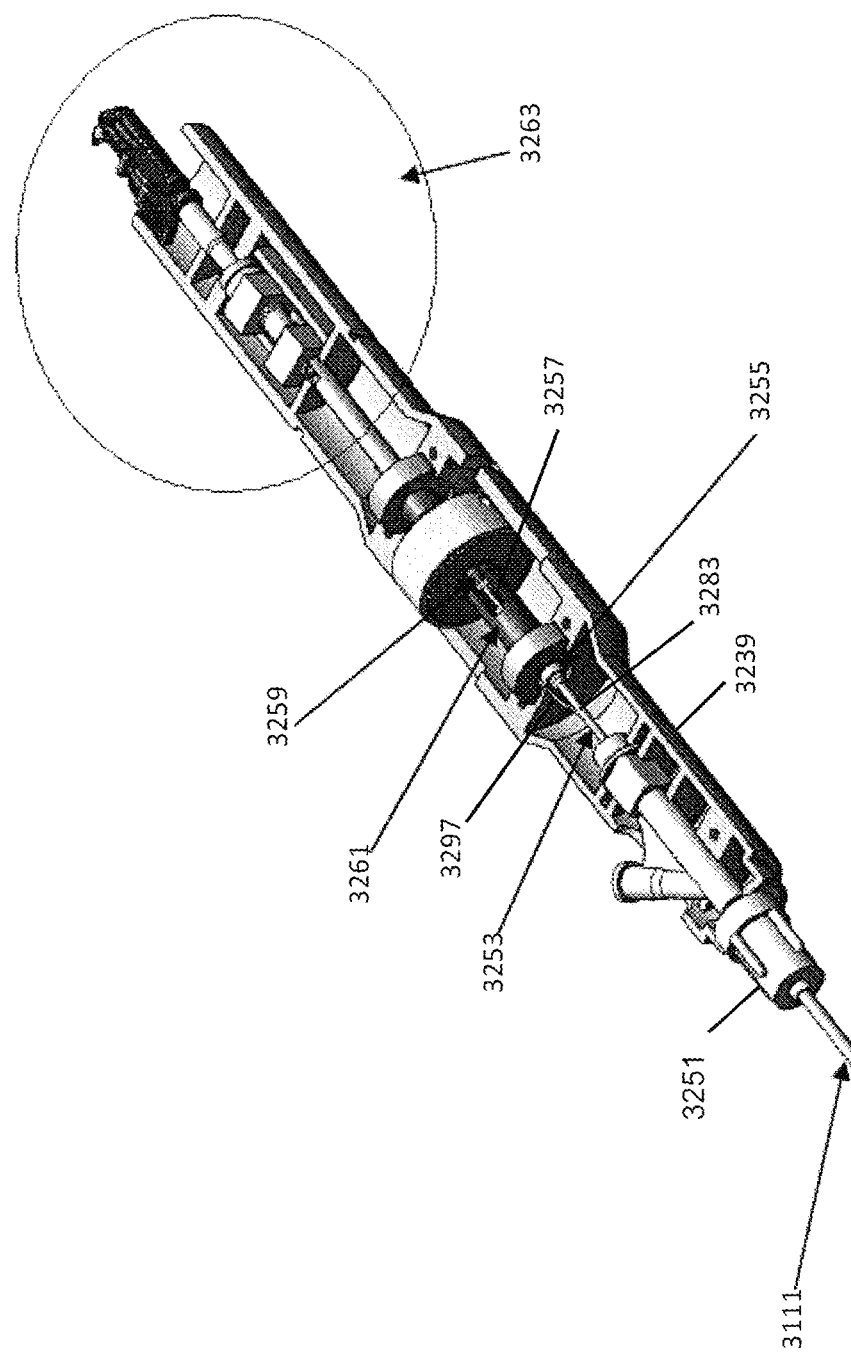

Referring to FIG. 30B, the proximal end of the catheter outer shaft 3111 can be connected to a rotation mechanism 3251 at the distal end of the catheter. The proximal end of the imaging shaft 3922 can be connected to an imaging shaft hypotube 3253 attached to an imaging shaft coupler 3255. The proximal end of the drive shaft 3113 can be attached to a drive shaft hypotube 3257 that is attached to a drive shaft coupler 3259. The hypotubes can telescope with respect to one another, thereby allowing for translation of the drive shaft within the imaging shaft, and can be configured to transmit torque and provide a fluid seal.

Figure 30C:
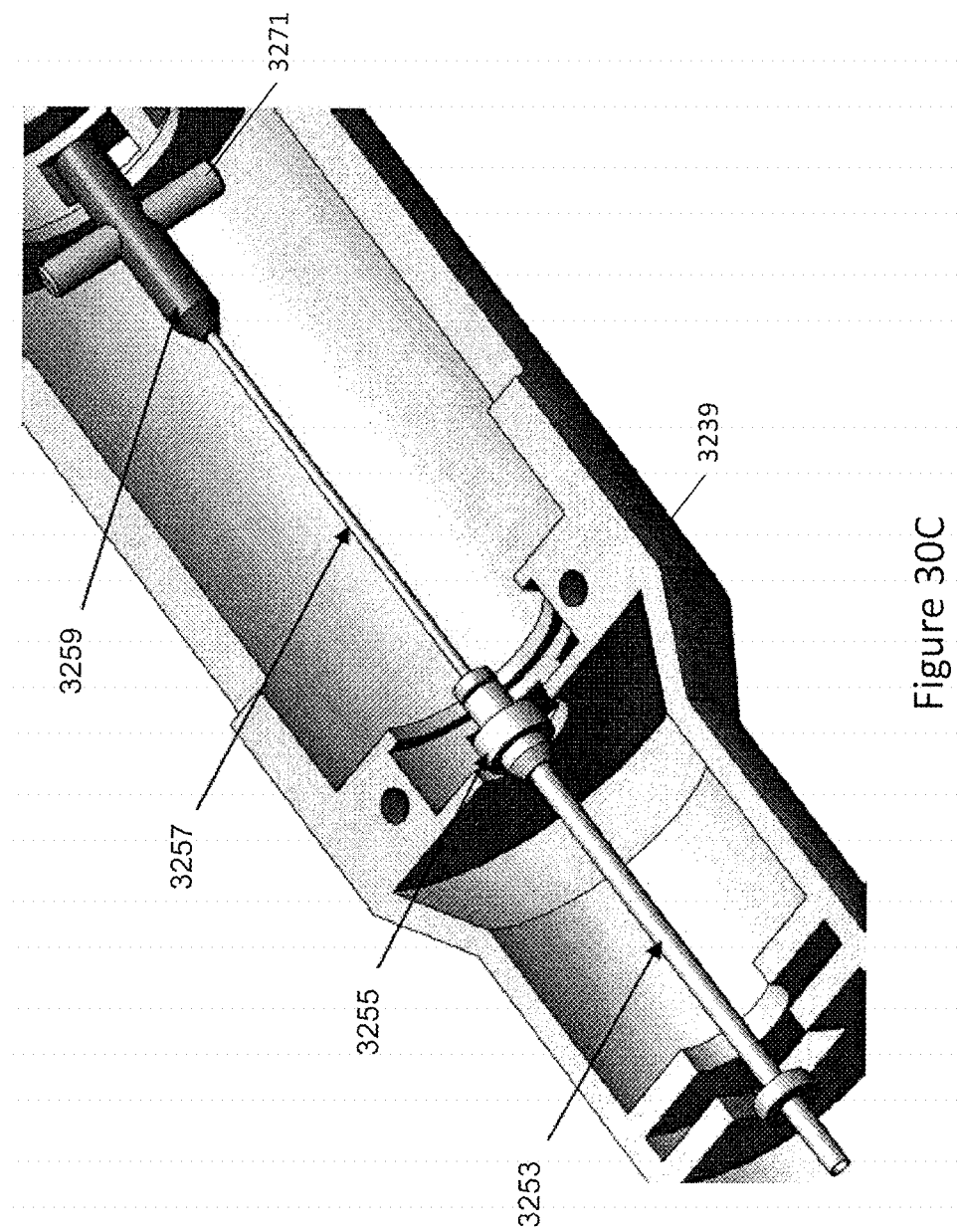

Referring to FIGS. 30B-30D, the imaging shaft coupler 3255 can be attached to a drive bridge 3261, which is in turn rotationally attached to the drive shaft coupler 3259 (which extends within and concentric with the drive shaft bridge 3261) through a pin 3271. The drive bridge 3261 is then attached to the proximal optical subassembly, which is configured to impart rotation thereto (thereby causing rotating of both the drive shaft 3113 and the imaging shaft 3922), such as via a drive system.

Referring to FIG. 30D, a bearing 3273 extends within the handle 3200. The bearing 3273 engages, with its inner race, a drivebridge coupler 3275 that is connected to the drive bridge 3261. This connection allows the drivebridge coupler 3275 (and drivebridge 3261) to rotate within the bearing 3273. The bearing 3273 further engages, with its outer race, a handle ring coupler 3277 connected to the handle ring 3247 where the outer race of the bearing 3273, the handle ring coupler 3277, and the handle ring 3247 do not rotate relative to the handle 3200. This engagement allows the bearing, and thus the drive bridge coupler, the drive shaft coupler, and the drive shaft hypotube to rotate relative to the handle 3200. Moreover, the engagement still allows the drive bridge coupler, the drive shaft coupler, and the drive shaft hypotube to translate proximally or distally when the handle ring is 3247 is translated proximally or distally as desired by the user.

As shown in FIGS. 30B and 30D, the optical fiber 3297 can be configured to extend out of the imaging shaft hypotube 3253 at a point 3283 just distal to the drive bridge 3261. The optical fiber 3297 can then traverse along the outer surface of the drive bridge 3261, such as within a groove in the drive bridge 3261, until it reaches the proximal optical assembly 3263, where it can connect to light source. Accordingly, while the drive shaft coupler 3259 and drive bridge 3261, and thus the drive shaft 3113, can move proximally and distally, the optical fiber 3297 can remain at a fixed axial position. Having the axial fiber in a fixed axial position advantageously avoids requiring additional length of fiber 3297 and/or placing unnecessary tension on the fiber 3297. Further, by having the optical fiber 3297 traverse along a groove in the outer surface of the drive bridge, the fiber 3297 can rotate with the drive bridge 3261. Rotating of the fiber with the drive bridge 3261 ensures that the fiber maintains a clear path as it is rotated, i.e., such that it is not required to wrap around anything within the handle. Thus, as the imaging connection subassembly 3263 is rotated by the drive system, the torque can be transmitted simultaneously through the imaging shaft 3922, optical fiber 3297, and drive shaft 3113.

Handle 3200 advantageously provides for rotation of the concentric imaging and drive shafts while allowing for axial movement of the drive shaft and not the imaging shaft or imaging fiber. The handle 3200 can further advantageously be configured such that the optical fiber does not have to undergo any steep bends therein, thereby making the fiber more robust.

In some embodiments, rotation of the drive shaft and imaging shaft can be decoupled by, for example, using magnets in the handle to couple the input rotation with the drive shaft rotation. In such a configuration, the internal drive shaft can be rotated at a speed different than the imaging shaft without interrupting the rotation of the optical fiber. Rotating the imaging shaft at a different speed, or without, the drive shaft can advantageously allow for imaging with cutting and/or rotating at different speeds that are individually optimized for imaging and cutting.

Although described as being used with catheter 3100, it is to be understood that the handle 3200 and/or elements of the handle could be used with a variety of different catheters while still providing separate rotation of concentric imaging and drive shafts and/or axial movement of one or more shafts without axial movement of another.

FIGS. 41A-41D show another example of an atherectomy catheter 31300 having drive and imaging shafts that are separated at the distal end and axially translatable relative to one another. The catheter 31300 is also configured to be urged against the vessel wall without a separate hinge mechanism. The catheter 31300 can include a catheter body 31301, a drive shaft 31313 extending inside an outer shaft 31311, and an imaging shaft 31322 extending through the drive shaft 31313 (e.g., such that the imaging shaft 31322 extends through the center of the device). The drive shaft can include a clear annular portion 31395 on the distal end thereof.

Figure 41A:
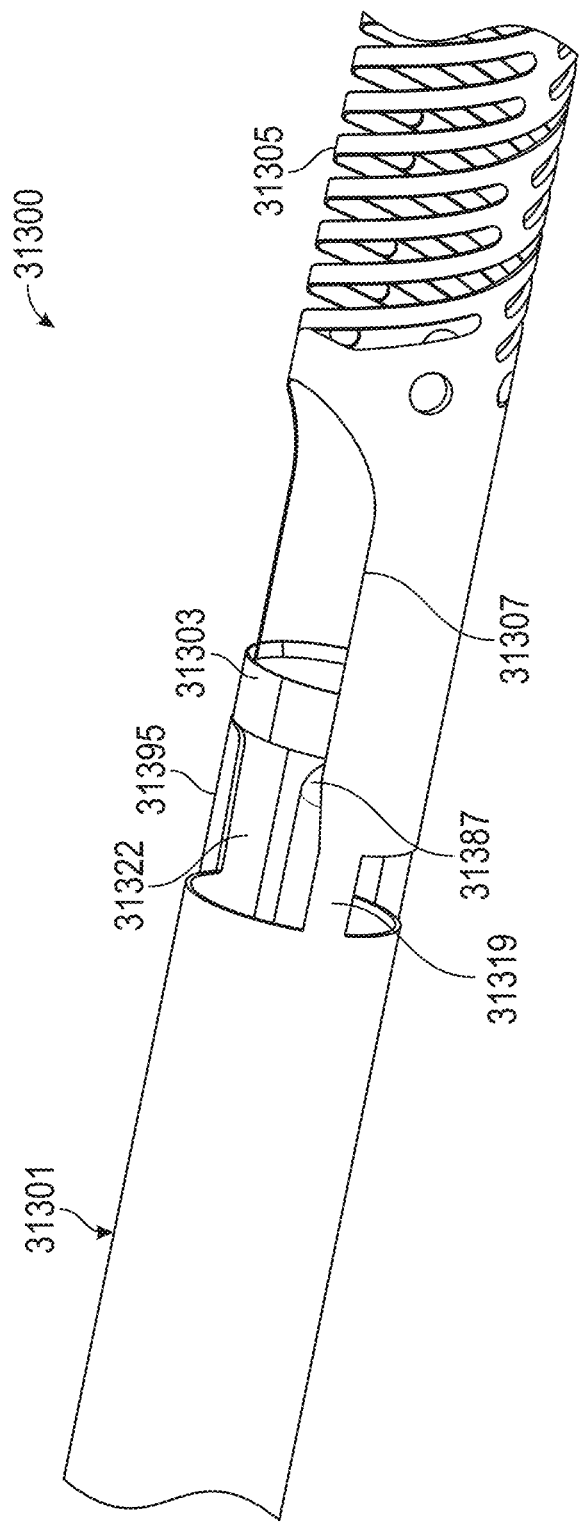
FIGS. 41A-41D shows an atherectomy device having a drive shaft and a coaxial imaging shaft extending within the drive shaft. The drive shaft and imaging shafts are separated from one another at the distal end and axially translatable relative to one another.
Figure 41B:
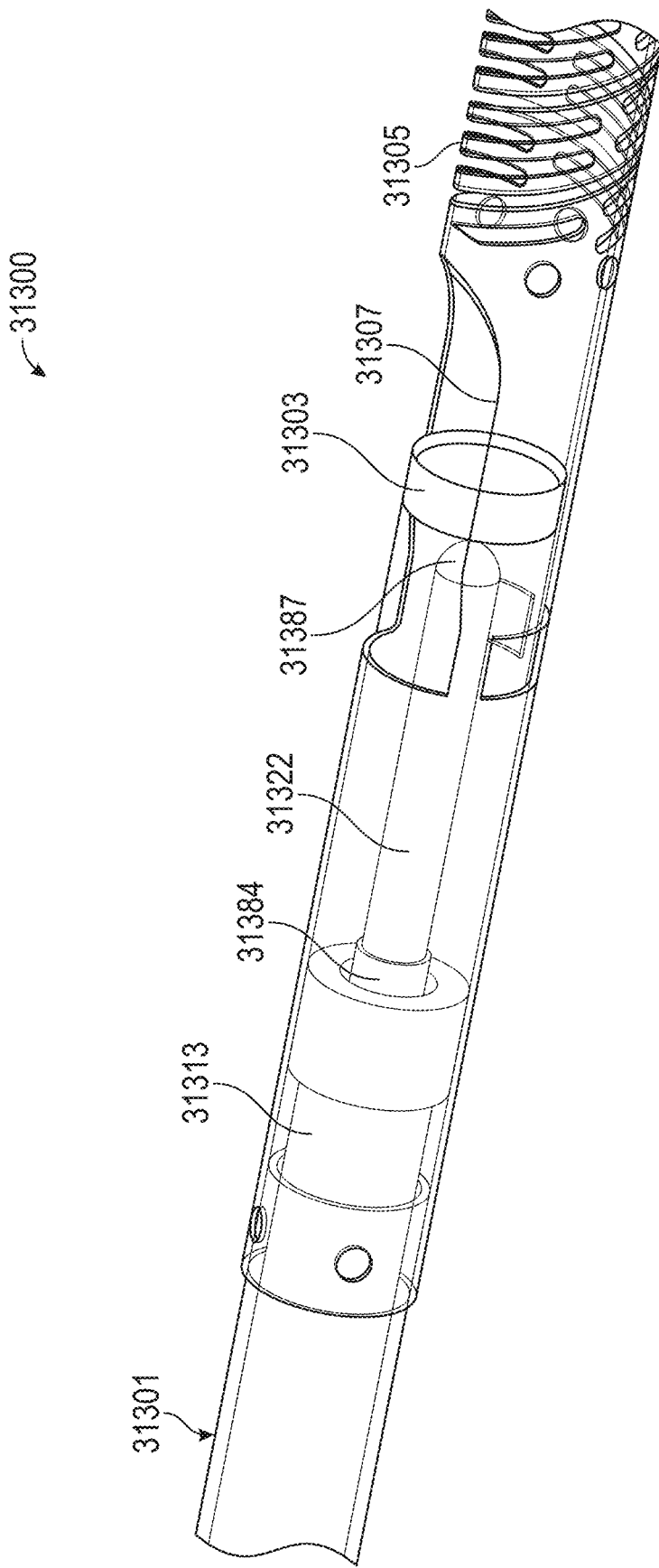
Figure 41C:
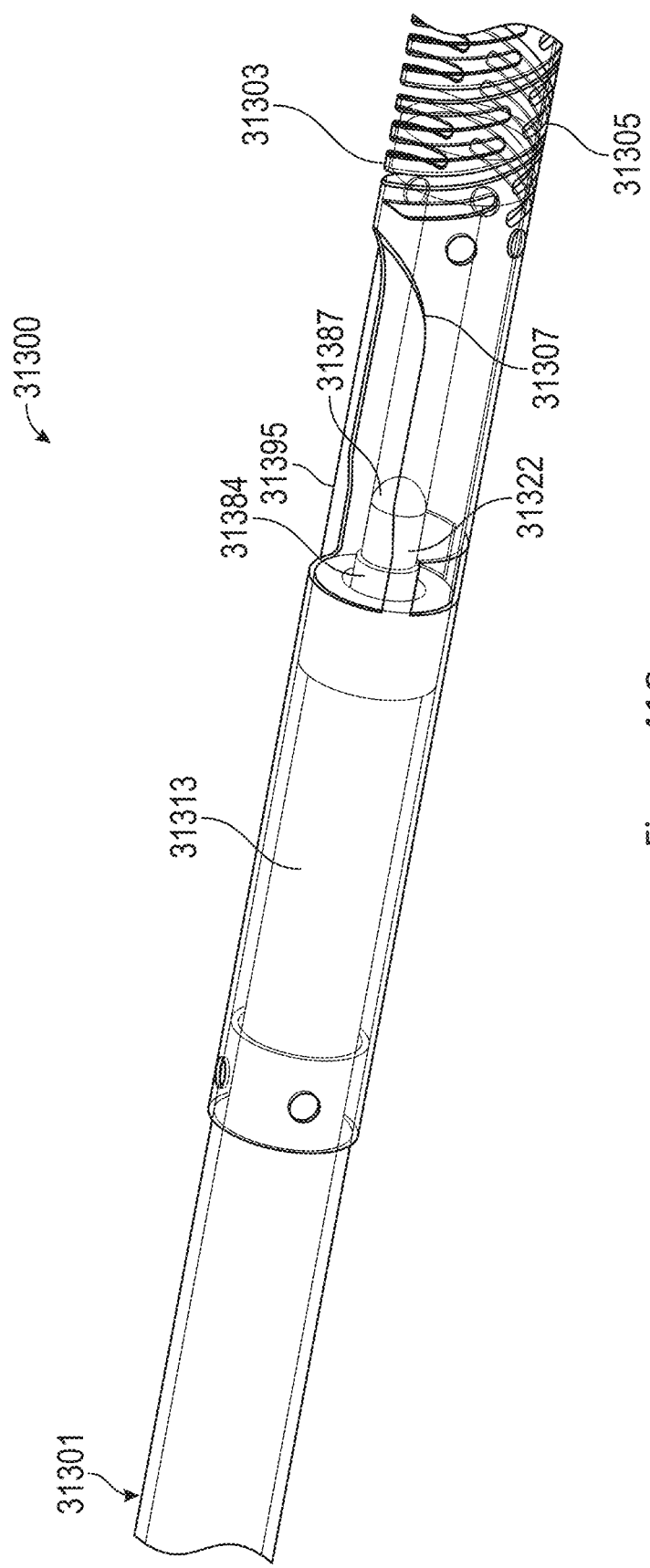
Figure 41D:
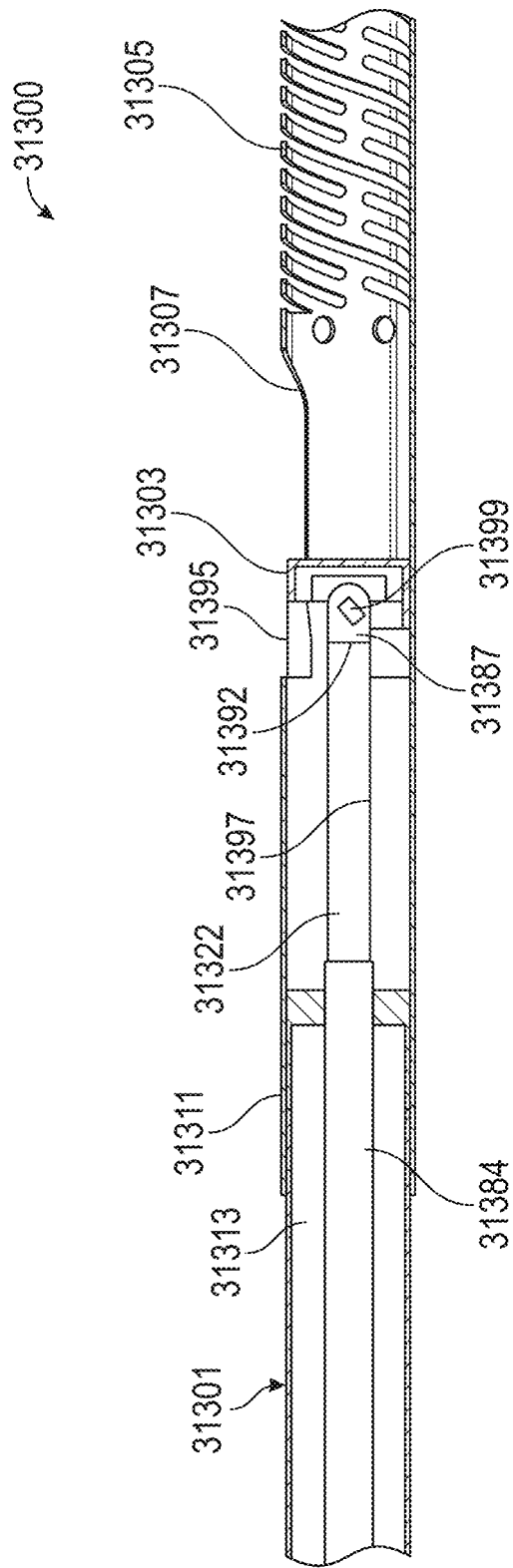

Referring to FIG. 41D, an optical fiber 31397 can extend through the center of the imaging shaft 31322 (and thus through the center of the catheter 31300) to provide the imaging (e.g., OCT) signal. The optical fiber 31397 can be attached at the distal end of the imaging shaft 31322 (such as in the bulb 31387, described below) but can be otherwise free to float within the imaging shaft 31322. The cutting window 31307 can also act as an imaging window through which the imaging element 31392 can be exposed. Similar to catheter 3100, the window 31307 can include a structural struts 31319 therethrough to provide structure support and to act as imaging markers.

Referring still to FIG. 41D, the imaging shaft 31322 can end in a bulb 31387, which can be made, for example, of stainless steel. The bulb 31387 can have a window therein through which light from the optical fiber can be transmitted.

The bulb 31387 can further include a glue in which the distal end of the optical fiber 3297 is embedded. Further, in some embodiments, the bulb 31387 can house a reflective element 31399, which can be situated at an angle (such as 40-60 degrees, e.g., 45 degrees) relative to the fiber so as to direct light from the optical fiber out through the clear annular portion 31395. Light can thus travel through the optical fiber 31397, bounce off of the reflective element 31399, extend through the clear annular portion 31395, through the imaging window 31377, and into the tissue.

As noted above, the drive shaft 31313 can include a clear annular portion 31395 at the distal end thereof. The clear annular portion 31395 can advantageously keep blood away from the exit path of the OCT light beam while providing a window for the light beam to travel through. The clear annular portion 31395 can include an optically transparent material, such as sapphire, polycarbonate, glass, or acrylic. In some embodiments, material used for the clear annular portion 31395 can be substantially free of micro-defects that can cause light therein to scatter, as such scattering of light can reduce the amount of light transmitted to and from the tissue and reduce image quality. In some embodiments, the materials used for the clear annular portion 31395 can have a flat response between 1260 nm and 1380 nm, i.e., the optical transmission can be relative constant between the used wavelength. Having a flat response advantageously ensures that there is no interference with OCT signals, improving image quality.

In some embodiments, the refractive index of the clear annular portion 31395 can be similar to the refractive index of the glue in which the distal end of the optical fiber is embedded. For example, the refractive index of polycarbonate is low, such as between 1.584 and 1.586, which in some embodiments can be comparable to the refractive index of the glue attached to the fiber, such as Masterbond EP42HT-2, EpoTek OG127-4 or OG116, produced by Epoxy Technology and UV curable photonics adhesive OP-4-20658. Using a clear annular portion 31395 having a refractive index that is similar to the glue in which the distal end of the optical fiber is embedded advantageously reduces the back-reflection at the glue/annular portion interface, thereby increasing image quality. As another example, the refractive index of sapphire is high, such as about 1.78, which can result in a higher back-reflection of a glue with a low refractive index (such as those described above) is used (a higher mismatch between the refractive indices results in higher back-reflection). Accordingly, a glue with a higher mismatch can be used, such as NOA 11625 from Norland Optical adhesives.

In other embodiments, rather than matching the refractive indices of the glue and the clear annular portion 31395, the housing geometry could be modified such that the light beam hits the clear annular portion 31395 at an angle so that very little or none of the reflective light can be coupled back into the fiber. In other words, the mirror, glue, fiber, the clear optical portion can be configured such that the angle of incidence of light to the interface medium between the glue and the clear annular portion is close to the polarization angle (also called the Brewster's angle) wherein all of the light is transmitted with minimal reflection.

When the clear annular portion 31395 is used, the focal length of the OCT light beam can be extended to compensate for the additional material through which the light has to travel. To do so, the beam diameter at the waste can be increased or a fiber or GRIN fiber with a larger diameter can be used.

A cutter 31303, such as an annular cutter, can be attached to the clear annular portion 31395 of the drive shaft 31313. In some embodiments, the cutter can be carved out of the clear annular portion 31395. For example, if the material for the clear annular portion 31395 is strong, such as sapphire, then the cutter 31303 and clear annular portion 31395 can be made of the same piece. Having the cutter 31303 and clear annular portion 31395 be made of the same piece can advantageously allow the images to be generated from a location very close to the cutter 31303, helping to achieve more precise cutting.

Further, similar to the catheter 3100, the catheter 31300 can include a nosecone 31305 extending from the distal end of the catheter body around the cutter 31303 to store tissue removed by the cutter 31303. The nosecone 31305 includes a cutting window 31307 therein configured to expose a portion of the cutter 31303. Similar to catheter 3100, the catheter 31300 can further includes an inflatable element, such as a balloon, configured to urge the cutter 31303 against the side of a vessel (and can include a corresponding optimized cutting window 31307 for cutting tissue as described with respect to catheter 3100).

The rotation of the imaging shaft 31322 and the drive shaft 31313 can be decoupled from one another at the distal end of the device, thereby providing for separate rotation of the cutter 31303 and the imaging element 31392. As described below, in some embodiments, the rotation of the imaging shaft 31322 and the drive shaft 31313 can be coupled at the proximal end (such as in the handle so as to be driven by the same motor) while remaining decoupled along the length of the catheter. In some embodiments, a separating layer 31384, such as a polyimide layer, can be placed between the drive shaft 31313 and the imaging shaft 31322. The separating layer 31374 can advantageously be used to prevent the transfer of energy between the drive shaft 31313 and the imaging shaft 31322 (for example, such that if the drive shaft 31313 gets bogged down while cutting, the chances of it affecting the imaging shaft 31322 will be reduced).

The catheter 31300 can include a mechanism for packing tissue into the nosecone 31305, such as by moving the drive shaft 31313 and cutter 31303 distally as shown in FIG. 41C. Advantageously, the drive shaft 3113 can be moved axially without movement of the imaging shaft 3122, thereby allowing for packing of the tissue without disrupting the imaging.

Similar to catheter 3100, by having an imaging shaft that is separate or decoupled from the drive shaft at their respective distal ends, the rotation of the cutter and the optical fiber can be mechanically isolated from one another, imaging quality can be improved due to reduced NURD.

Further, by having separate imaging and drive shafts, the drive shaft can advantageously be used to pack tissue while maintaining the imaging element in the same location, thereby ensuring that the imaging location is constant and well known.

By placing the imaging element within the center of the catheter, the catheter can advantageously be reduced in size (for example, relative to a device where there is an annular space between an inner drive shaft and an outer imaging shaft). The catheter 31300 can thus be, for example, less than 8 French, such as 6-8 French, which can advantageously make the catheter 31300 useable in small diameter vessels, such as coronary vessels. Further, by placing the drive shaft around the imaging shaft, as in catheter 31300, the drive shaft can advantageously be larger and more robust, such as 0.05" to 0.06." In some embodiments, the drive shaft can include a multi-layer coil, which can also advantageously increase the robustness of the drive shaft, thereby providing a cutting system that is more resistant to stalling.

In some embodiments, the drive shaft 31313 and imaging shaft 31322 can be unconnected at the distal end of the catheter to allow for separate imaging and cutting but connected at the proximal end of the catheter so that they can be rotated from the same source, such as the same drive system. Although the shafts can be connected at the proximal end of the cutter, rotational distortion can still be avoided because the rotating motor can be strong enough to spin at the same speed regardless of the torque placed on the cutter at the distal end. Accordingly, even if the drive shaft slows down due to stalling, the imaging shaft can continue to rotate at the same constant speed.

Figure 42:
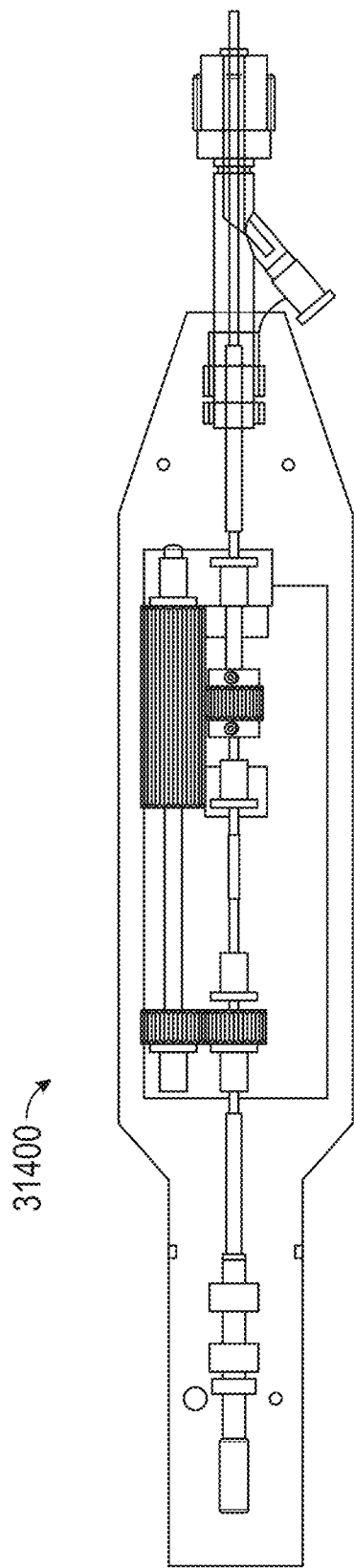
FIG. 42 is an exemplary handle for use with the atherectomy device of FIGS. 41A-41D.

Referring to FIG. 42, the catheter 31300 can be used with a handle 31400 configured such that the drive shaft 31313 and the imaging shaft 31322 can be rotated separately at the distal end of the catheter while being rotated with the same source at the proximal end of the catheter. The handle 31400 can be configured similar to the handle 3400 of FIGS. 32A-32B, described further below.

FIGS. 31A-31E show another example of an atherectomy catheter 3300 having drive and imaging shafts that are separated at the distal end and axially translatable relative to one another. The catheter 3300 is also configured to be urged against the vessel wall without a separate hinge mechanism. The catheter 3300 can include a catheter body 3301, a cutter 3303 extending from the distal end of the catheter body 3301, and an imaging tip 3308 near the distal end of the catheter body 3301 but proximal to the cutter 3303. A nosecone 3305 can extend from the distal end of the catheter body and around the cutter 3303 to store tissue removed by the cutter 3303. The nosecone 3305 can include a cutting window 3307 therein configured to expose a portion of the cutter 3303. The catheter 3300 can further include an inflatable element, such as a balloon 3315 (see FIG. 31D), configured to urge the cutter 3303 against the side of a vessel.

Figure 31A:
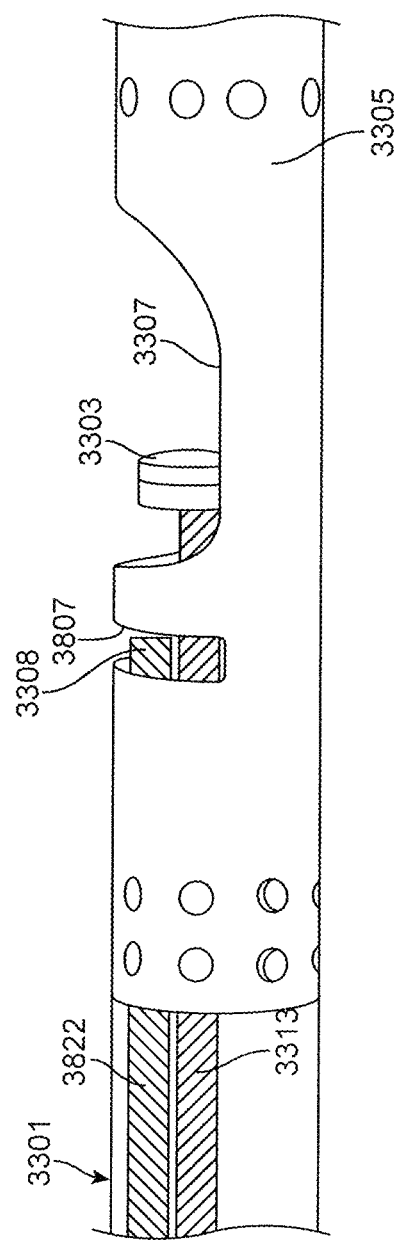
FIGS. 31A-31E show an atherectomy device having a drive shaft and a parallel imaging shaft extending alongside the drive shaft. The drive shaft and imaging shafts are separated from one another at the distal end and axially translatable relative to one another.
Figure 31B:
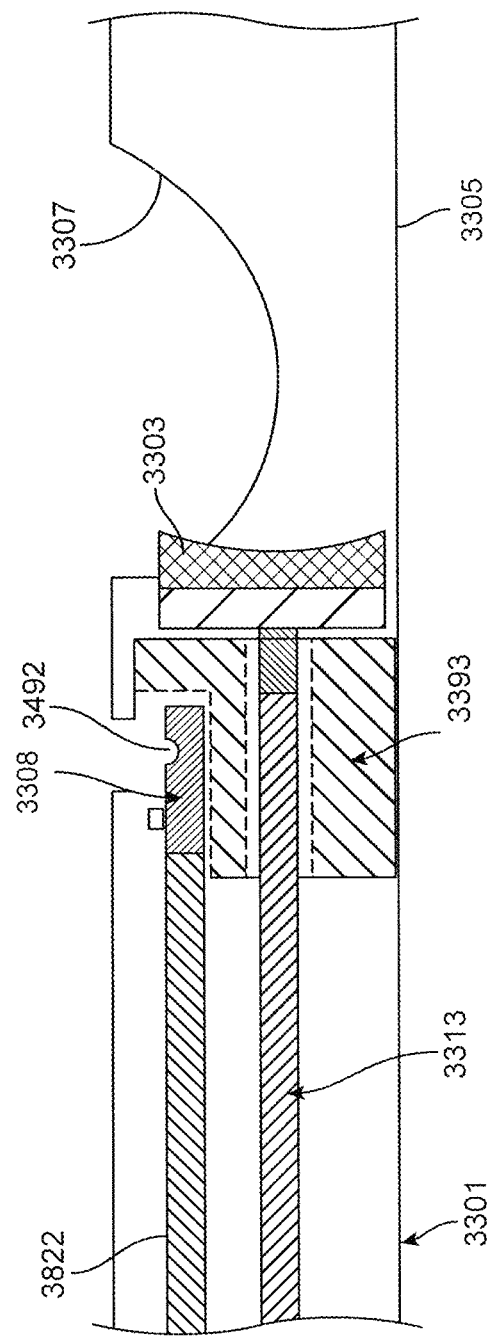
Figure 31C:
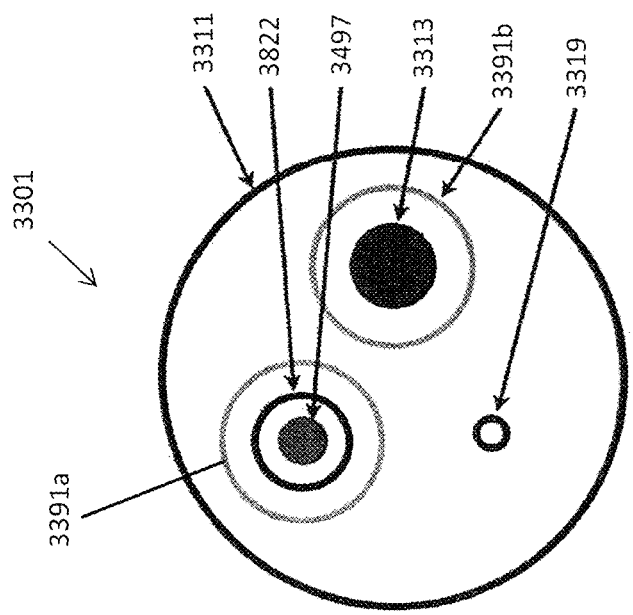

Referring to FIGS. 31A-31C, the catheter body 3301 can include an outer shaft 3311 and a drive shaft 3313 extending inside the outer shaft 3311. The outer shaft 3311 can be configured to be turned, such as turned manually, to position the cutter 3303 and/or the imaging tip 3308 toward the desired location. The drive shaft 3313 can be attached to the cutter 3303 to rotate the cutter 3303. Rotation of the cutter 3303 can provide cutting due to the rotational motion of the sharp distal cutting edge. The drive shaft 3313 can be rotated at up to 10,000 rpm, such as 1,000 to 5,000 rpm, e.g., 1,000 rpm, though rotation in both directions or at different speeds is possible. The drive shaft 3313 can be held on-center at the distal tip of the device using a bushing 3393 (within which the drive shaft 3313 can rotate).

Referring still to FIGS. 31A-31C, the catheter 3300 can further include an imaging element 3492, such as an OCT imaging element. The imaging element 3492 can include an optical fiber 3497. The imaging tip 3308 can be attached to an imaging shaft 3822 that extends within the catheter body 13301 next to or parallel with the drive shaft 3313. The imaging shaft 3322 can be off-center at the distal tip of the device and be parallel to the drive shaft 3313, as shown in FIG. 31B. The imaging shaft 3322 can be held in place by the bushing 3393.

The rotation of the imaging shaft 3822 and the drive shaft 3313 can be decoupled at the distal end of the device, thereby providing for mechanically isolated rotation of the cutter 3303 and the imaging element 3492. As described below, in some embodiments, the rotation of the imaging shaft 3822 and the drive shaft 3313 can be coupled at the proximal end (such as in the handle so as to be driven by the same motor) while remaining decoupled along the length of the catheter. Optionally, as shown in FIG. 31C, the imaging shaft 3822 and/or the drive shaft 3313 can include a stationary sheath 3391A and 3391B therearound to provide protection and support.

The outer shaft 3311 can include an imaging window 3807 through which the imaging element 3492 can be exposed. The imaging window 3807 can have a width of less than 1 mm while still enabling OCT imaging therethrough. The imaging window 3807 can extend 360 degrees around the circumference of the outer shaft 3311, but can include structural struts 3317 extending thereacross to both provide structural support and act as imaging markers. In some embodiments, the struts 3317 can be offset to account for the off-center imaging tip 3308, enabling accurate OCT image orientation.

The imaging window 3807 can further be used as a flush port to allow flush fluid to be delivered through the imaging shaft 3822 and to the area of imaging, thereby improving image quality. Advantageously, by having the fluid pumped directly through the imaging shaft, the dimensions of the imaging window 3807 do not need to be extended to enable this type of flushing.

The optical fiber 3497 can run through the imaging shaft 3822 to provide the imaging (e.g., OCT) signal. The optical fiber 3497 can be attached at its distal end to the imaging tip 3308. The optical fiber 3497 can otherwise be free to float within the imaging shaft 3822. As shown in FIG. 31E, a reflective element 3499, such as a mirror, polished pin, a film deposited on the surface of the tip 3308, or polished surface of the tip 3308 itself, can further be located on the imaging tip 3308 to radially direct light from the optical fiber 3497 into the tissue. The reflective element 3499 can be at an angle, such as 35 to 55 degrees, such as 45 degrees, relative to the central axis of the fiber 3497 to reflect light into the tissue. The distal end of the optical fiber 3497 can be located less than 3 mm from the distal edge of the cutter 3303, such as less than 2.0 mm from the cutting edge, such as less than or equal to 1.5 mm, such as less than or equal to 1 mm. By having the imaging element 3492 close to the cutting edge, the resulting image can advantageously align with the portions of the vessel being cut.

Figure 31D:
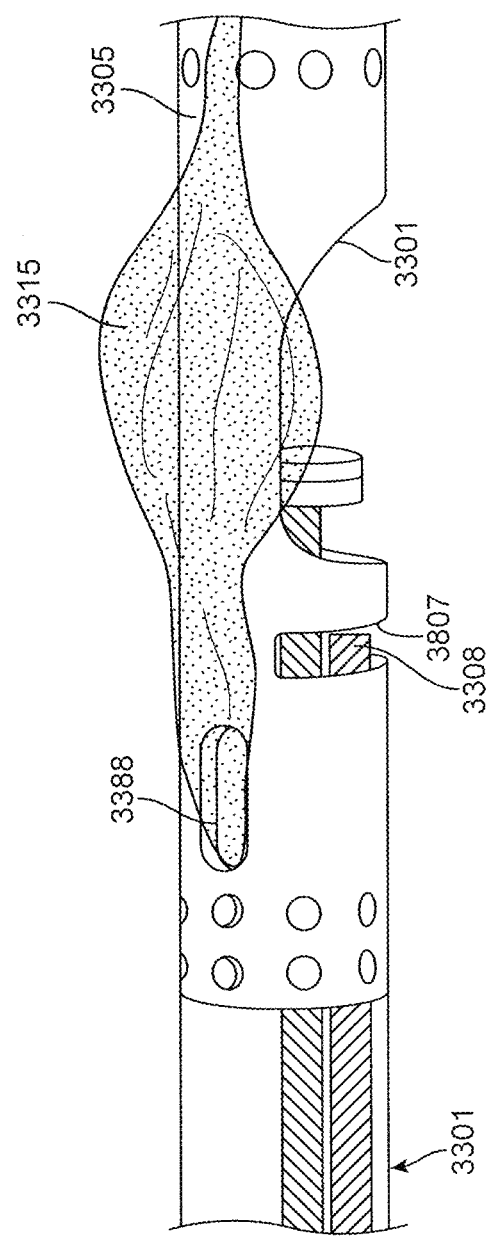
Figure 31E:
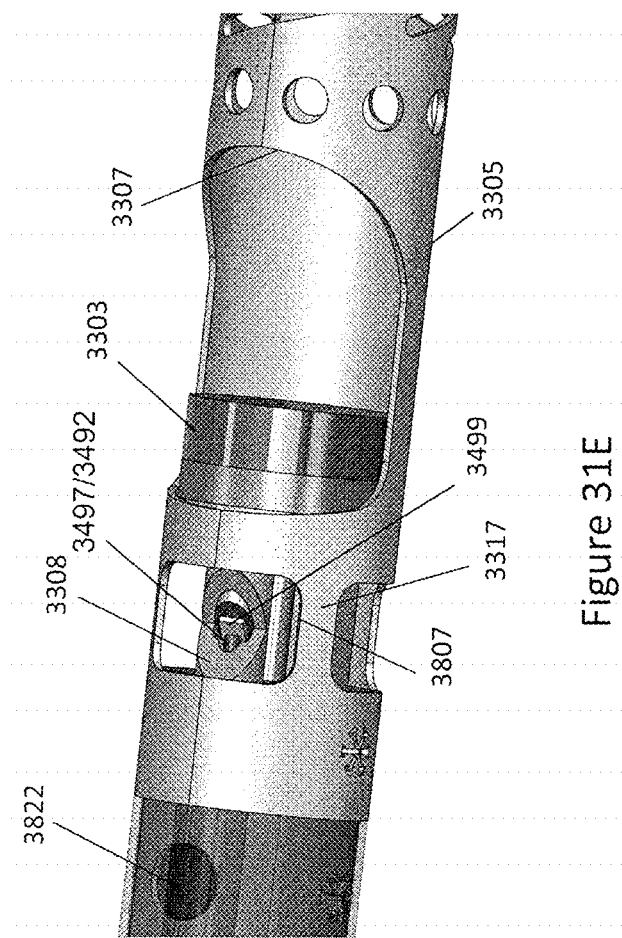

As shown in FIG. 31D, an inflatable element, such as a balloon 3315, can be located opposite to the cutting window 3307. The balloon 3315 can be attached to an inflation tube 3319 (see FIG. 31C), which can run inside the outer shaft 3311. Thus, the balloon 3315 can be attached at the distal end to the outer shaft 3311 (just proximal to the imaging window 3807) and at the proximal end to the inflation tube 3319 inside the outer shaft 3311, such as through a hole 3388 in the outer shaft 3311. Inflation of the balloon 3315 can urge the cutting window 3307 and thus the cutter 3303 against the tissue. Further, the cutting window 3307 and the balloon can be sized and dimensioned such that inflation of the balloon 3315 causes the tissue to be forced into the cutting window, thereby improving the cutting quality of the device. For example, the cutting window 3307 can have the same or similar dimensions to that described above for the cutting window 3107 of catheter 3100. In some embodiments, the balloon is approximately spherical and inflates to a diameter of 3-6 mm for a device sized to treat vessel that are greater than or equal to 2.5 mm.

The catheter 3300 can further include a mechanism for packing tissue into the nosecone 3305. Thus, for example, the cutter 3303 can be moved distally by extending the drive shaft 3313 distally. Advantageously, the drive shaft 3313 can be translated proximally and distally while keeping the imaging shaft 3822 (and thus the imaging sensor 3492) in place.

Similar to catheters 3100 and 31300, by having an imaging shaft that is separate from the drive shaft at least at the proximal ends in catheter 3300, rotational distortion, such as NURD, can reduced or eliminated, thereby improving imaging quality. Further, by having separate imaging and drive shafts, the drive shaft can advantageously be used to pack tissue while maintaining the imaging element in the same location, thereby ensuring that the imaging location is constant and well known. Moreover, by having separate imaging and drive shafts, the fluid flush can be delivered close to the imaging element even when the drive shaft is moved distally to pack tissue.

Further, by using the balloon of catheter 3300 to urge the cutter against the vessel wall and by having an optimally designed cutting window, tissue can be pulled into the cutting window and cut, thereby improving cutting quality without requiring a hinge mechanism in the catheter. Further, the balloon can advantageously act as an occlusion element to at least partially block blood flow to the imaging element, thereby reducing the amount of saline flush required to obtain a clear image and improving image quality.

In some embodiments, the drive shaft 3313 and imaging shaft 3822 can be unconnected at the distal end of the catheter to allow for separate imaging and cutting but connected at the proximal end of the catheter so that they can be rotated from the same source, such as the same drive system. Although the shafts can be connected at the proximal end of the cutter, rotational distortion can still be avoided because the rotating motor can be strong enough to spin at the same speed regardless of the torque placed on the catheter at the distal end. Accordingly, even if the drive shaft slows down due to stalling, the imaging shaft will continue to rotate at the same speed.

Figure 32A:
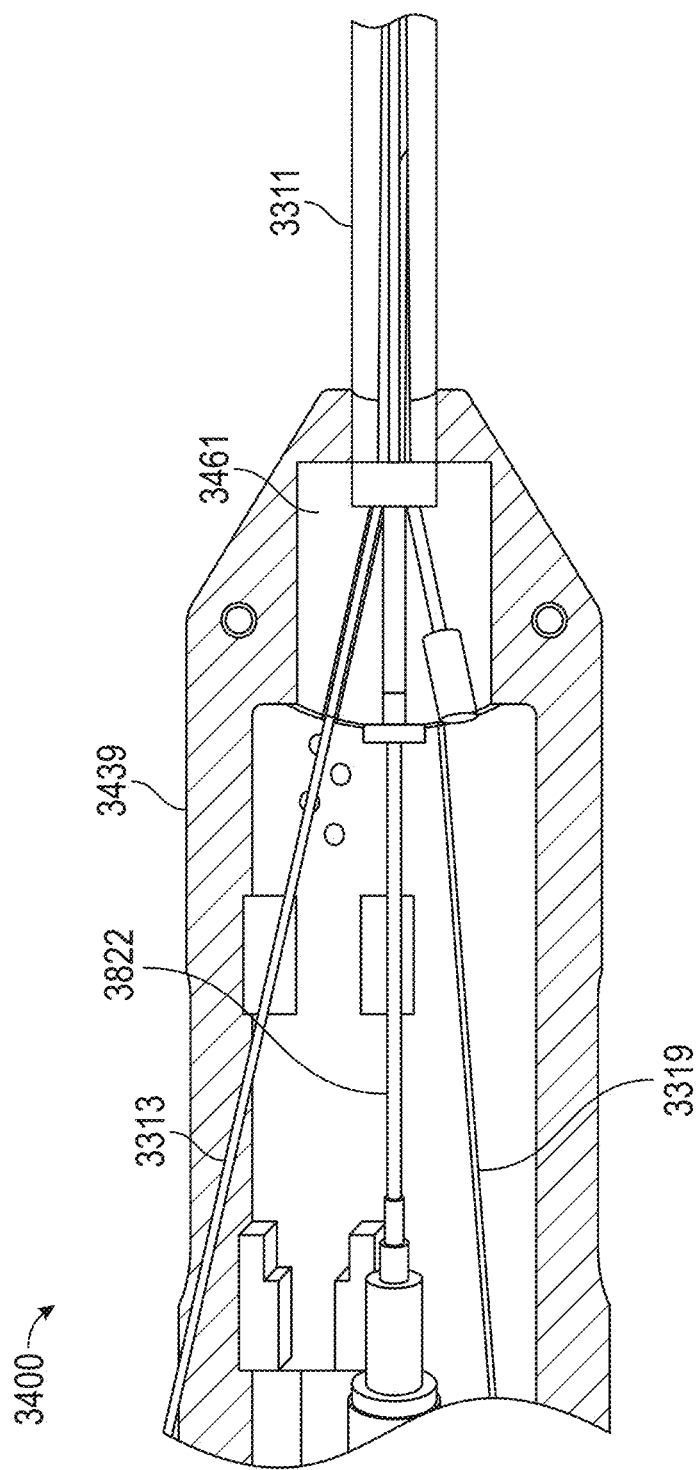
FIGS. 32A-32B show a handle for use with the atherectomy device of FIGS. 31A-31E.
Figure 32B:
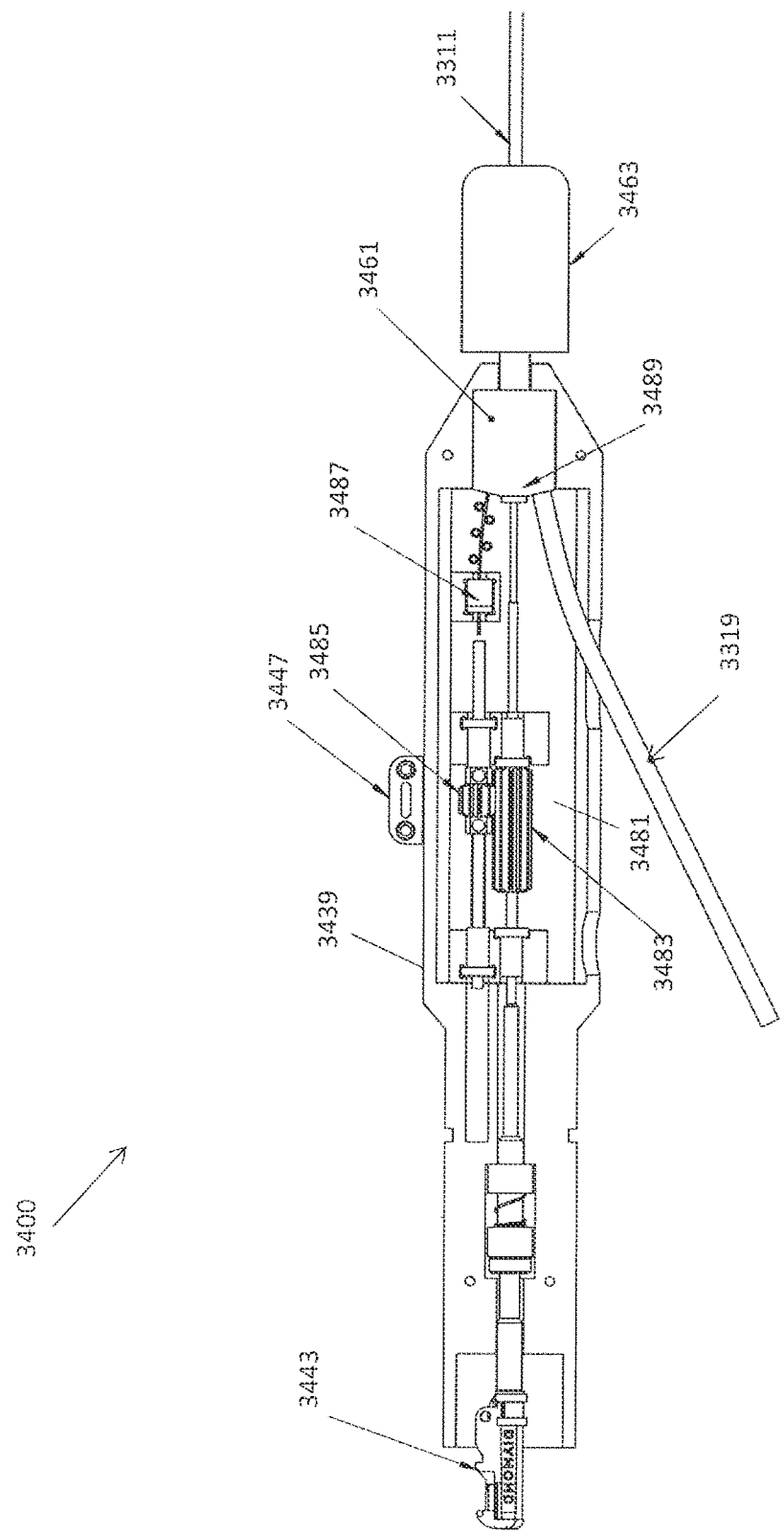

An exemplary handle 3400 for use with catheter 3300 is shown in FIGS. 32A-32B Referring to FIG. 32A, the handle 3400 is configured to ensure that the drive shaft 3313, the imaging shaft 3822, and the balloon inflation lumen 3319 inside the outer shaft 3311 of the catheter 3300 are all properly managed and controlled. A breakout port 3461 in the handle 3400 can separate the drive shaft 3313, the imaging shaft 3822, and the balloon inflation lumen 3319 within the handle 3400. In doing so, the imaging shaft 3822 can be run through the center of the handle 3400 so as to connect on-axis to the drive system through an optical connector (described below). The drive shaft 3313 extends towards the top of the handle 3400, where it is connected to the geared system (described below). Further, the balloon inflation lumen 3319 extends towards the bottom of the handle, where it can be bonded into a tube with a female luer lock attachment for balloon inflation. In some embodiments, the breakout port 3461 can be directly bonded to the outer shaft 3311 (as shown in FIG. 31A) or it can be attached to a rotation knob 3463 (as shown in FIG. 31B).

The handle 3400 can be configured such that the drive shaft 3313 and the imaging shaft 3822 can be rotated separately at the distal end of the catheter but rotated with the same source at the proximal end of the catheter. The handle 3400 can further include a mechanism that allows for axial translation of the drive shaft 3313 (e.g., to pack tissue with the cutter), but not the imaging shaft 3822.

Referring to FIG. 32B, the handle 3400 can include an outer shell 3439, a rotation knob 3463 configured to connect to the outer shaft 3311 of the catheter 3300, and an optical connector 3443 configured to engage with a drive system and light source. The optical connector 3443 can provide both rotation from the drive system to directly drive the imaging shaft 3822 and an OCT signal from the light source that can be translated through the optical fiber 3497 embedded in the central lumen of the imaging shaft 3822.

As shown in FIG. 32B, the handle can include a geared mechanism 3481 configured to transfer rotation from the imaging shaft 3822 to the drive shaft 3313. The geared mechanism 3481 can include an imaging drive gear 3483 connected to a drive shaft gear 3485. Thus, as the imaging shaft 3822 is rotated by the drive system through the optical connector 3443, the imaging drive gear 3483 will rotate, causing the drive shaft gear 3485, and thus the drive shaft 3113, to rotate. In some embodiments, the geared mechanism 3481 of the handle 3400 can include a clutch that allows the drive shaft 3313 rotation to be turned on and off while still allowing the imaging shaft 3822 to rotate (advantageously allowing for imaging without requiring simultaneous cutting). The imaging drive gear 3483 can be longer than the drive shaft gear 3485. Accordingly, during translation of the handle ring or slide 3447, the drive shaft gear 3485 can be translated back and forth across the imaging drive gear 3483, thereby maintaining full rotation of the drive shaft 3313 during the packing and opening actions.

The handle 3400 can further include a handle ring or slide 3447 configured to slide along the handle 3400 to translate the drive shaft 3313 axially, such as to pack tissue by the cutter 3303. As shown in FIG. 32B, a fluid seal 3487 ensures that the handle 3400 is fluid-tight during translation of the drive shaft 3313. The fluid seal 3487 can be in-line with the drive shaft gear 3485 to prevent the drive shaft 3313 from buckling. A sheath can be used bridge the gap between the fluid seal 3487 and the breakout port 3461. Moreover, an additional fluid seal 3489 can be provided on the breakout port 3461 to provide a seal for the imaging shaft 3822.

The outer rotation knob 3463 can be configured to rotate relative to the rest of the handle 3400 to allow the user to torque the outer shaft 3311 to orient the distal tip of the catheter 3300 in the desired position. The knob 3463 can rotate the outer shaft 3311 independently of the imaging shaft 3822, drive shaft 3313, and inflation tube 3319. Accordingly, the rotation of the knob can be limited to reduce wrapping or unwanted extension of the shafts/tube. For example, the rotation can be limited to less than 3 full rotations, such as less than 2 full rotations, such as less than 1.5 full rotations in either direction.

Referring to FIGS. 33A-33F, in one embodiment, the outer rotation knob 3463 can include a mechanism for stopping the rotation if rotated more than 1 full rotation (360°) and less than 3 full rotations, such as approximately 1.5 rotations. The outer rotation knob 3463 can also be configured so as to not require lengthening or shortening of the outer shaft 3311 during rotation. That is, some rotation knobs (with pins attached to the outer shaft and a spiral track in the handle) can cause the outer shaft to be lengthened relative to the handle. Because the drive shaft would not concurrently lengthen and shorten, the fiber could snap and/or the cutter could be forced to move proximally or distally relative to the outer shaft. Accordingly, the outer rotation knob 3463 described herein can be configured so as to not require lengthening or shortening of the outer shaft 3311.

Figure 33A:
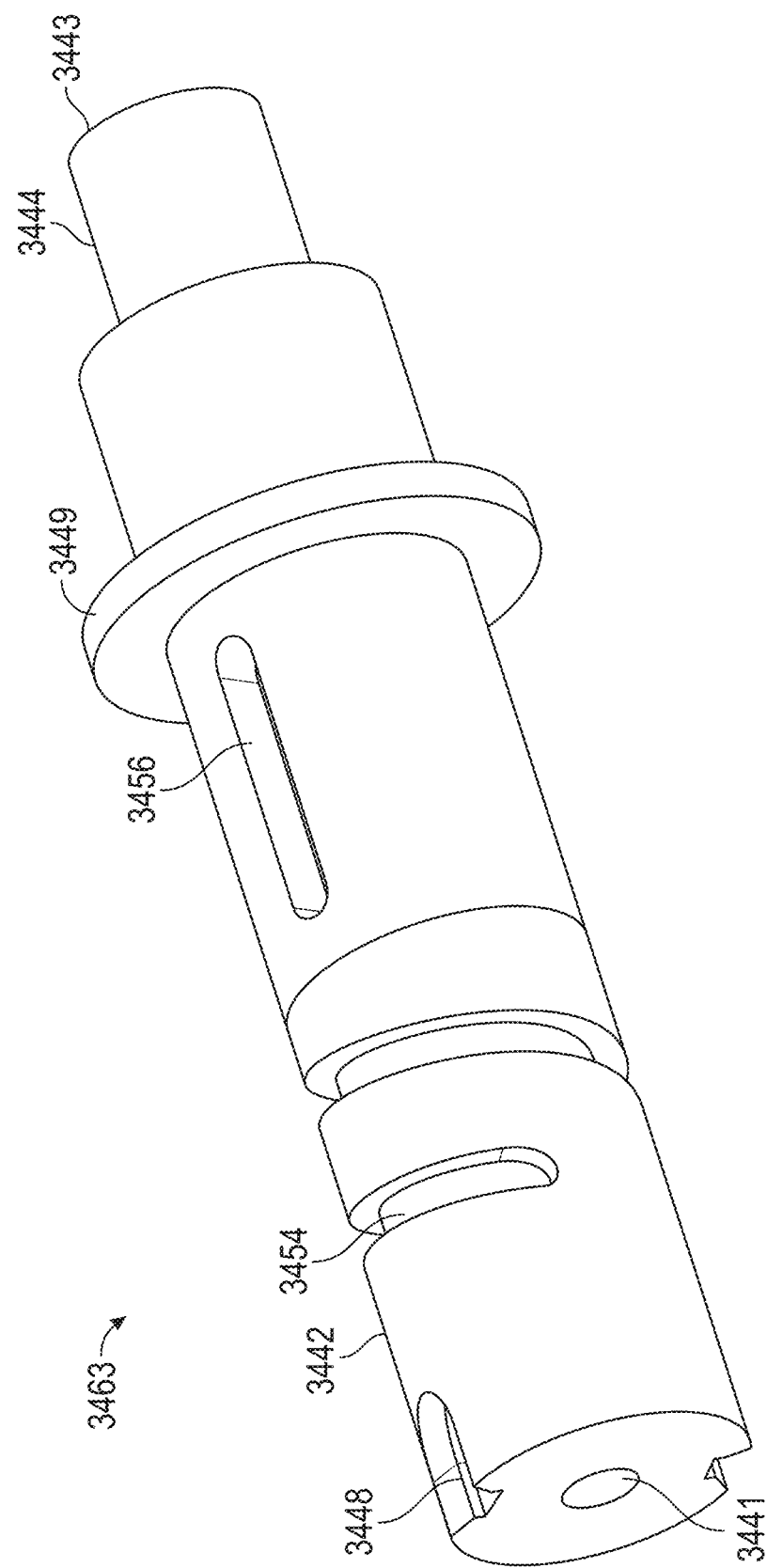
FIGS. 33A-33F show a knob configured to rotate the outer shaft of the catheter of FIGS. 31A-31E up to a set number of rotations without lengthening the device.
Figure 33B:
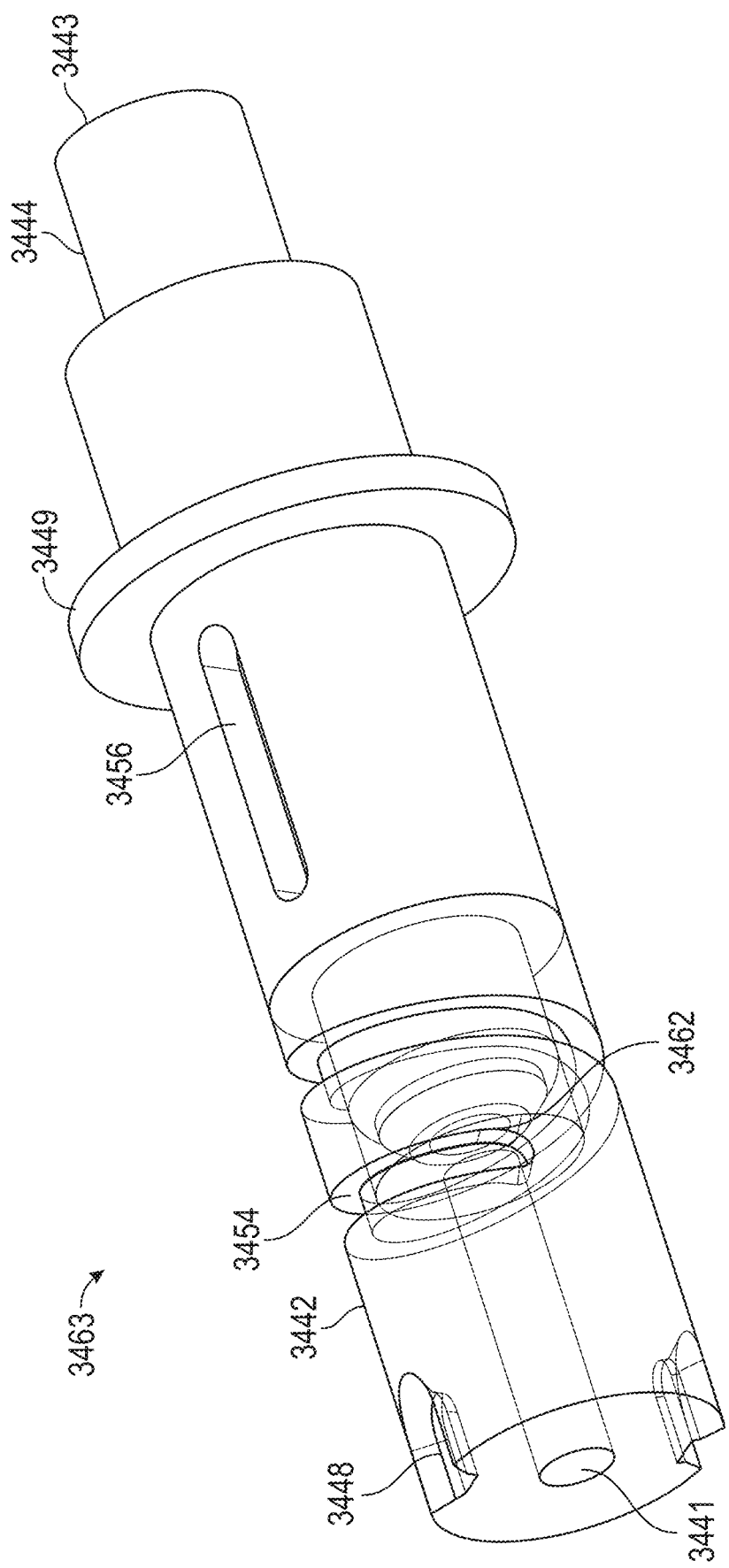

Referring to FIGS. 33A and 33B, the knob 3463 can include a shaft inner portion 3442 connectable to the outer shaft 3311 at connection point 3441 and a handle inner portion 3444 connectable to the rest of the handle 3400 at connection point 3443. The shaft inner portion 3442 can include a spiral track 3454 that spirals around the inner portion 3442 for more than 360 degrees and less than 1080 degrees, such as approximately 540 degrees. The shaft inner portion 3442 can further include one or more linear tracks 3456 extending axially along the inner portion 3442. For example, there can be two linear tracks 3456 that are located 180 degrees away from one another. Having more than one linear track 3456 can advantageously help stabilize the relative axial movement of parts within the knob 3463. An o-ring 3462 (see FIG. 4D) can create a seal between the two inner portions 3442, 3444. The inner portion 3442 can further include one or more indents 3448 therein as well as an annular ridge 3449 extending therearound.

Figure 33C:
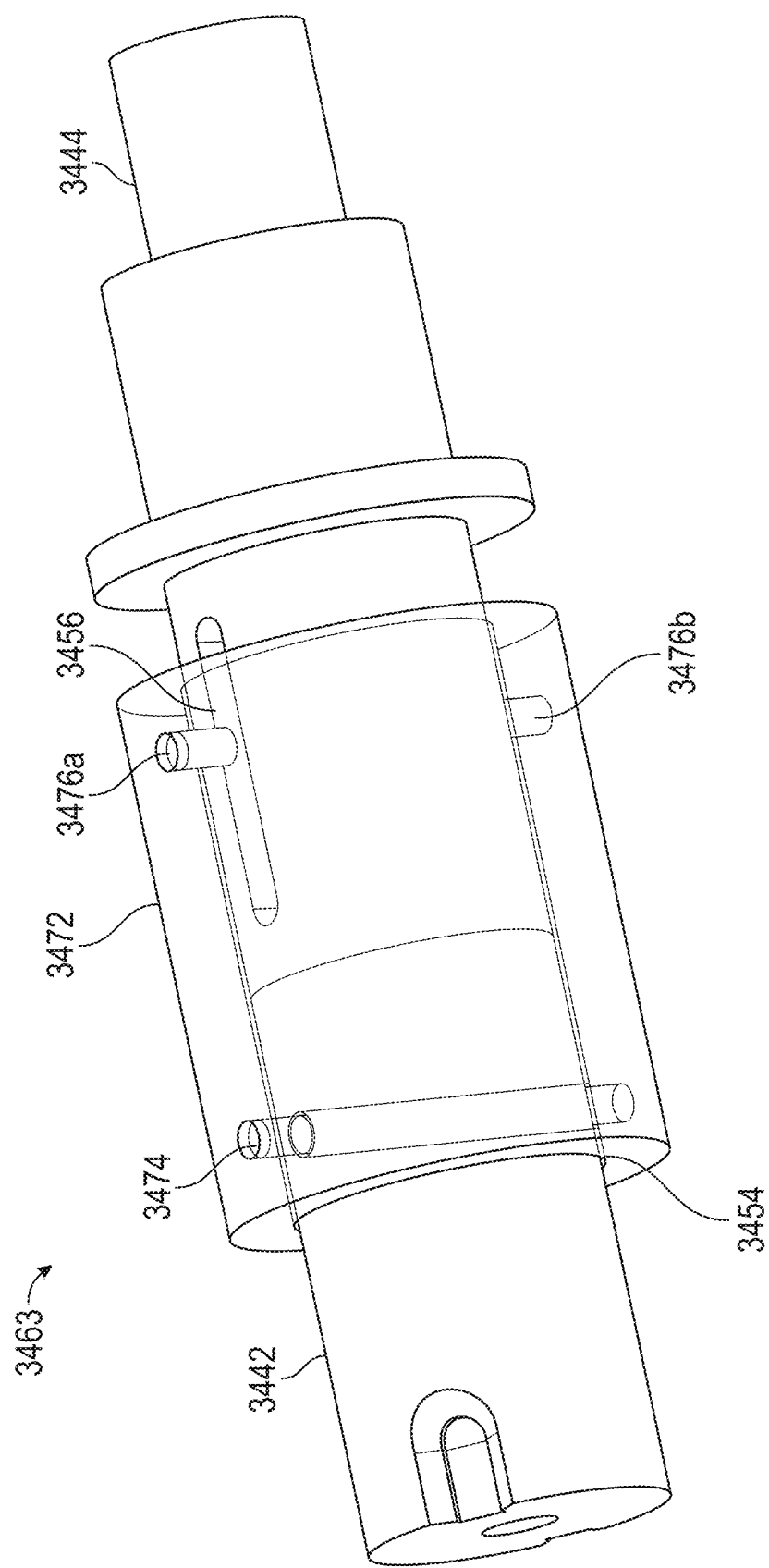

Referring to FIG. 33C, the knob 3463 can further include a sleeve 3472 that extends around the shaft inner portion 3442. The sleeve 3472 can have a pin 3474 that fits into the spiral track 3454, as well as pins 3476a and 3476b that fit into the linear track 3456.

Figure 33D:
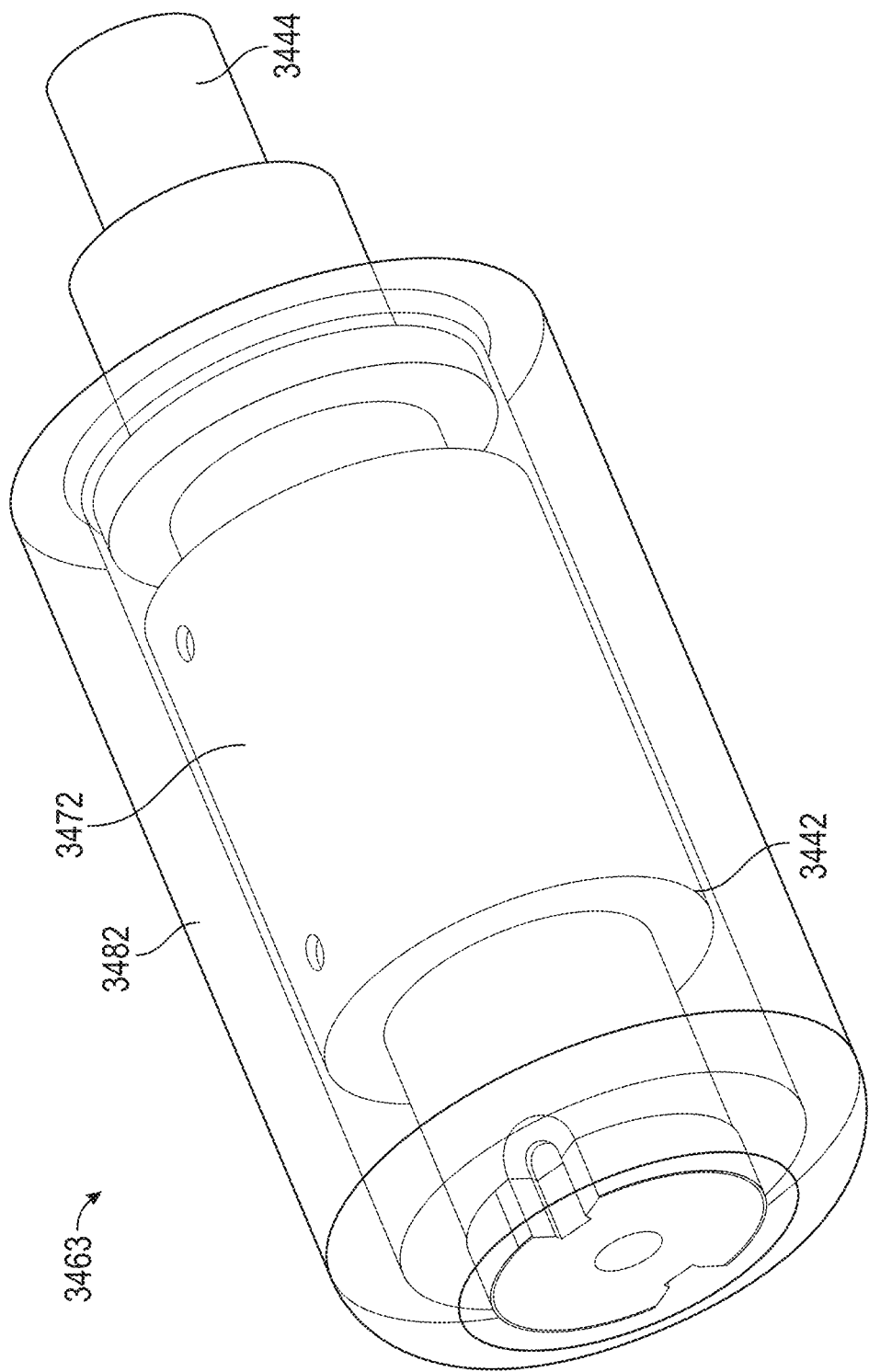

Referring to FIG. 33D, the knob 3463 can further include an outer portion 3482 that extends around the sleeve 3472 (but not attached to the sleeve 3472). The outer portion 3482 can snap fit with the ridge 3449 and the indents 3448 of the shaft inner portion 3442.

Figure 33E:
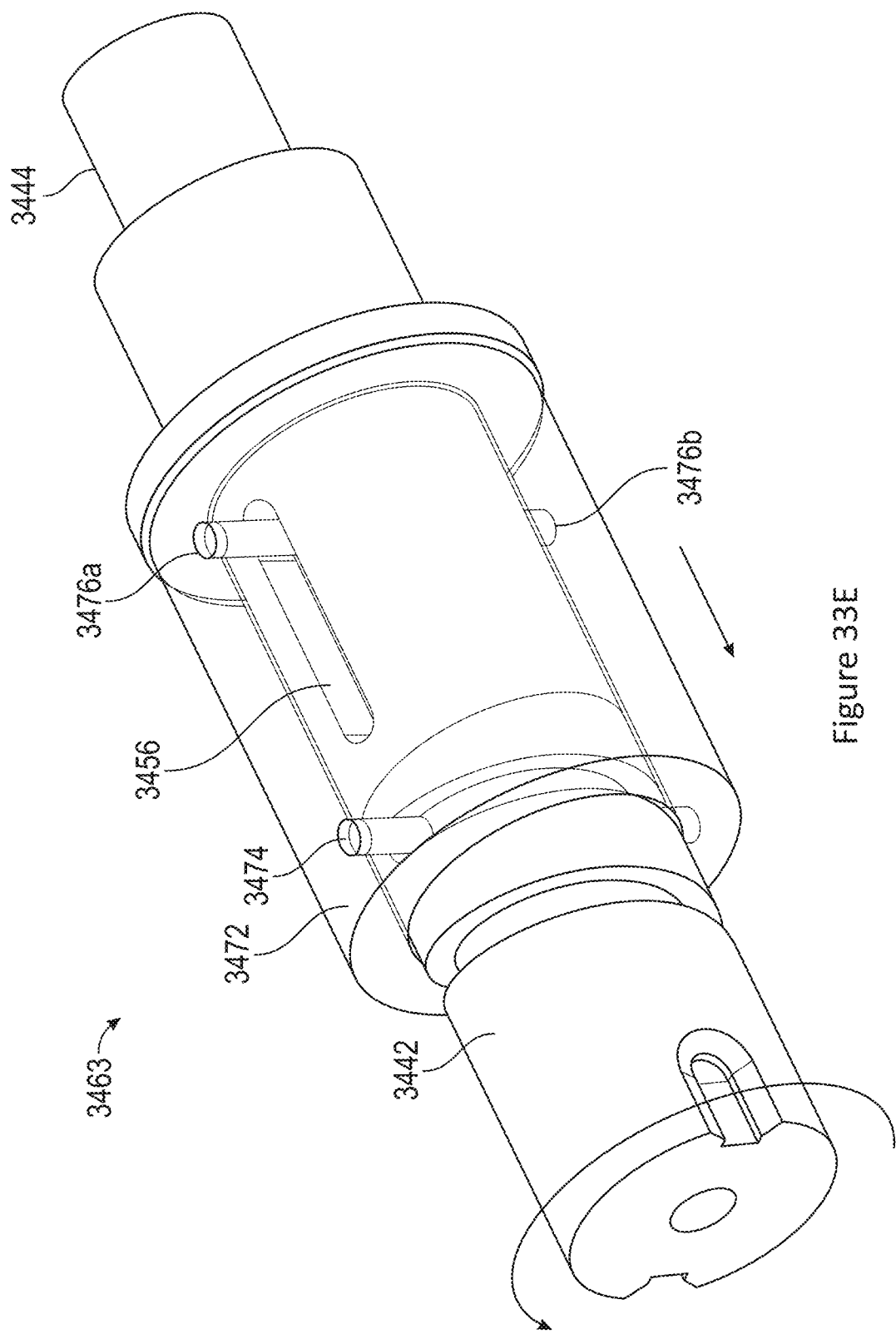
Figure 33F:
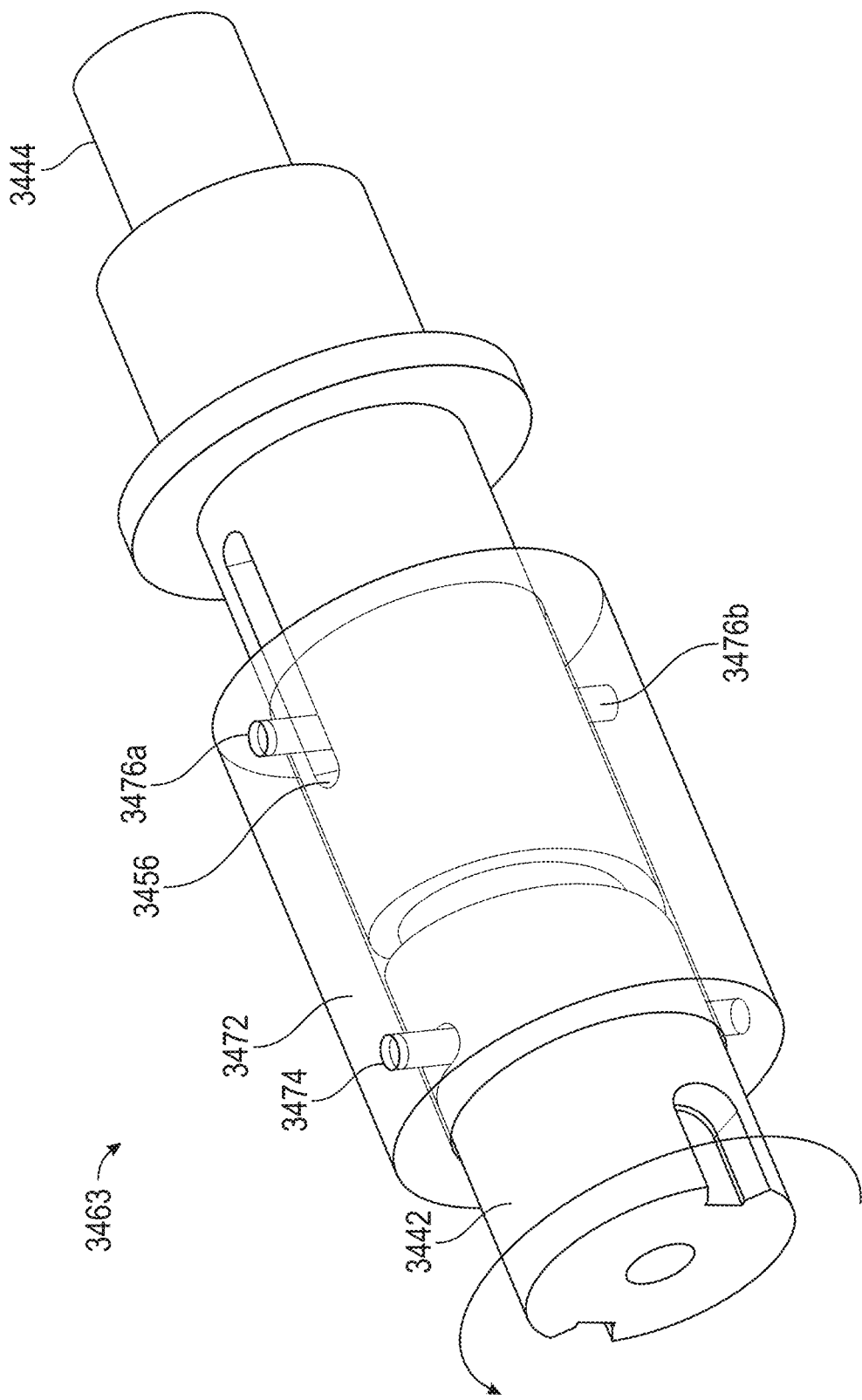

Thus, referring to FIGS. 33E and 33F, as the outer portion 3482 is rotated by a user, it will rotate the drive shaft inner portion 3442. As the drive shaft inner portion 3442 rotates, the pin 3474 will slide along the spiral track 3454 and cause the sleeve 3472 to translate linearly due to the placement of the pins 3476a and 3476b in the linear track 3456 (as shown in the movement of the sleeve 3472 distally from FIG. 33E to FIG. 33F). When the pins 3474 in the spiral track 3454 reaches the end (and/or when the pins 3476a and 3476b in the linear track 3454 reach the end), rotation in that direction is prevented. Thus, the rotation knob (and thus the drive shaft) is only able to rotate a fixed number of rotations. Further, because the sleeve 3472 translates linearly rather than the outer shaft 3311, relative movement of the cutter and/or distortion in imaging can be avoided.

In some embodiments, the handle 3400 can include one or more luer ports such that the user can deliver imaging flush and balloon inflation to the distal tip.

Handle 3400 advantageously provides for rotation of the parallel imaging and drive shafts while allowing for axial movement of the drive shaft and not the imaging shaft or imaging fiber. Moreover, the handle provides for connection to a drive system at high rotation speeds (such as up to 10,000 rpm), it provides a fluidic seal to enable flushing from the handle to the distal tip, it provides for balloon inflation via air or solution, it allows for independent rotation of the outer shaft, and it allows the balloon lumen to be moved from the outer diameter of the torque shaft to the interior annular space of the torque shaft to increase usability of the device.

Although described as being used with catheter 3300, it is to be understood that the handle 400 and/or elements of the handle could be used with a variety of different catheters while still providing separate rotating of concentric imaging and drive shafts and/or axial movement of one or more shafts without axial movement of another.

FIGS. 34A-37B show an exemplary atherectomy device (and corresponding exemplary handles) having a balloon hinge mechanism configured to drop the nosecone and expose a cutter as well as a return biasing mechanism to realign the nosecone with the catheter body.

Referring to FIGS. 34A and 34B, a catheter 31100 can include a catheter body 31101, a cutter 31103 extending from the distal end of the catheter body 31101, and a nosecone 31105 attached to the distal end of the catheter body 31101. The nosecone 31105 can include a cutting window 31107 through which the edge of the cutter 31103 can be exposed. The nosecone 31105 can be configured to deflect away from the longitudinal axis 31110 of the catheter body 31101 at an angle, such as at a hinge point 31109. In use, this deflection can expose the cutter 31103 through the cutting window 31107 and/or radially push the cutter 31103 into a wall of the vessel in which the atherectomy catheter is inserted.

Figure 34C:
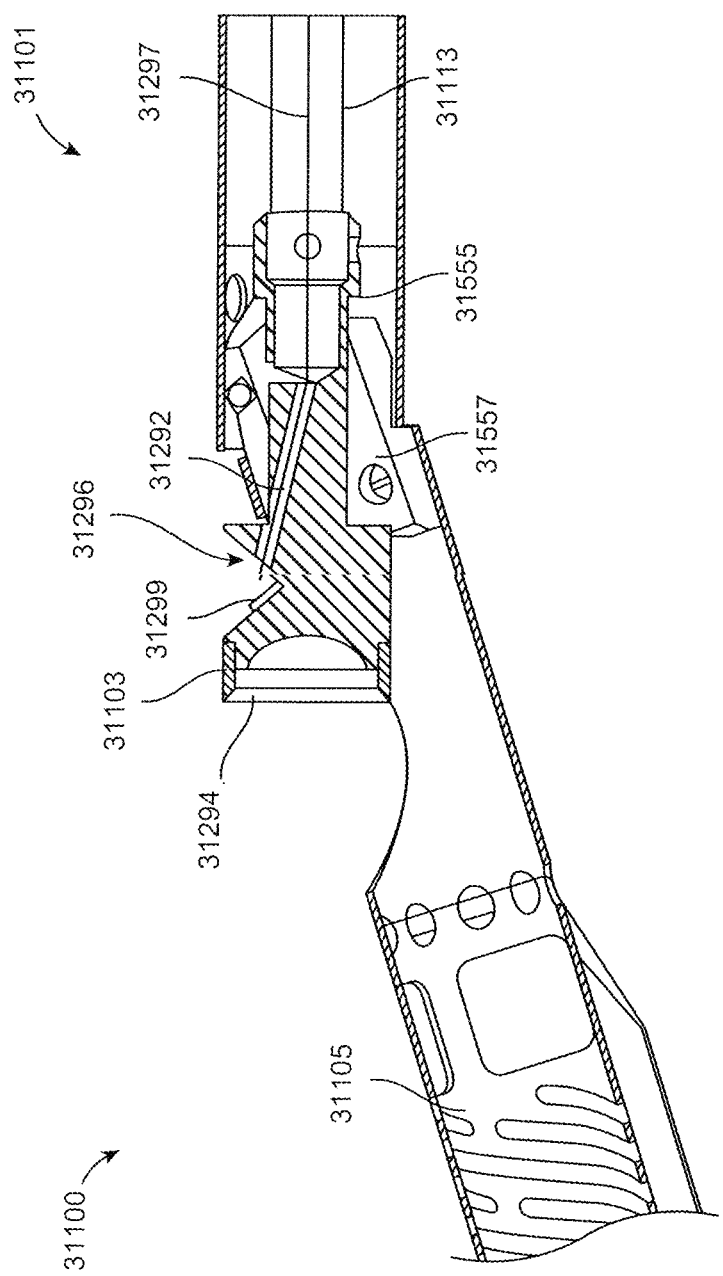
FIGS. 34C-34D show an exemplary detailed view of the imaging element and the hinged activation closing mechanism of the catheter of FIGS. 34A-34B.
Figure 34D:
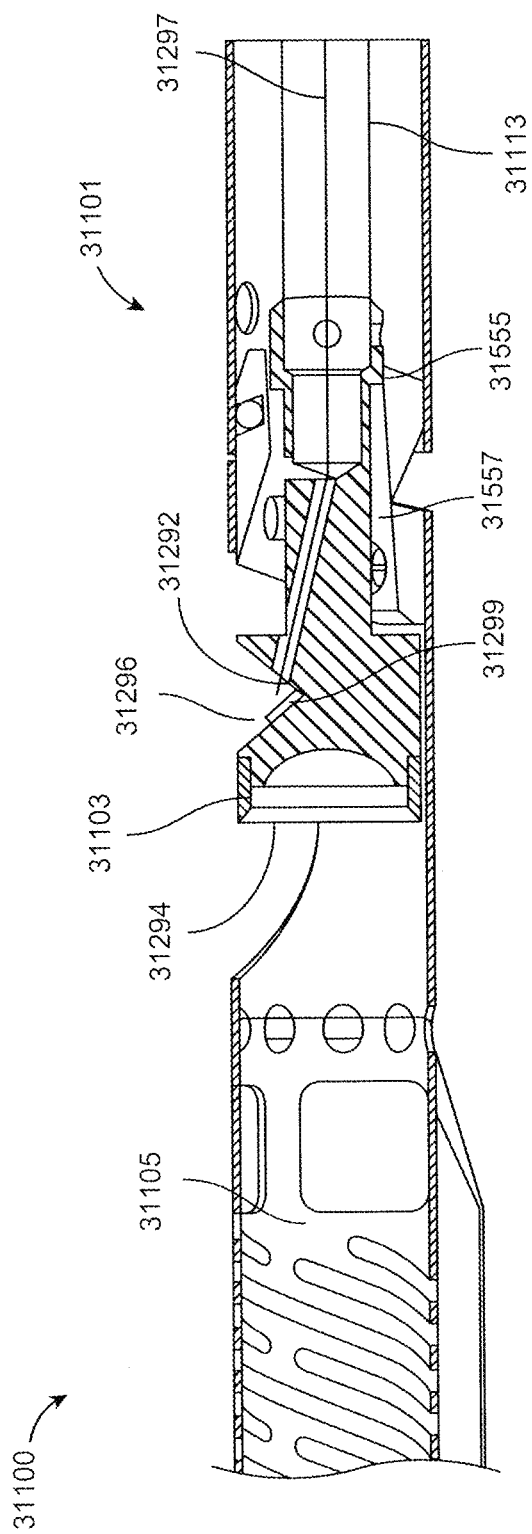

Referring to FIGS. 34C-34D, the atherectomy catheter 31100 can include an imaging element 31292, such as an OCT imaging element, proximal to the cutting edge 31294 of the cutter 31103. An optical fiber 31297 can run through the elongate body, such as on-axis with the catheter body 31101 through a drive shaft 31113, to provide the OCT signal. The optical fiber 31297 can be attached at the distal end to the cutter 31103, such as in an opening 31296 in the cutter 31103. The optical fiber 31297 can otherwise be free to float within the catheter body 31101 and/or drive shaft 31113. A reflective element 31299, such as a mirror, can further be located within the opening 31296 in the cutter 31103 to radially direct light from the optical fiber 31297 into the tissue. The reflective element 31299 can be at an angle, such as 35 to 55 degrees, such as 45 degrees, relative to the central axis of the fiber 31297 to reflect light into the tissue. The distal end of the optical fiber 31297 can be located less than 3 mm from the cutting edge 31294, such as less than 1.5 mm from the cutting edge, such as less than or equal to 1.2 mm, such as less than or equal to 1 mm. By having the imaging element 31292 close to the cutting edge 31294, the resulting image can advantageously align with the portions of the vessel being cut.

Referring back to FIGS. 34A-34B, the catheter body 31101 can include an outer shaft 31111 and a drive shaft 31113 extending inside and concentric with the outer shaft. The outer shaft 31111 can be configured to be turned, such as turned manually, to position the cutter 31103 and/or the imaging element toward the desired location. The drive shaft 31113 can be attached to the cutter 31103 to rotate the cutter 31103. Rotation of the cutter 31103 can provide cutting due to the rotational motion of the cutting edge while providing the rotation necessary to image the circumference of the inner wall of a vessel via the imaging element. The drive shaft 31113 can be rotated at up to 2,000 rpm, such as approximately 1,000 rpm in a single direction, though rotation in both directions or at different speeds is possible.

As described above, the atherectomy catheter 31100 can include a hinge point 31109 to provide a rotational axis during opening of the nosecone 31105. For example, the hinge point 31109 can be a living hinge or a pin that attaches to either the proximal or distal housings. As shown in FIGS. 34A-34B, an inflatable element, such as a balloon 31115 can be located proximate to the hinge point 31109 and opposite to the cutting window 31107. The balloon 33115 can be linked to both the distal end of the catheter body 31101 and the proximal end of the nosecone 31105. For example, a sling element 31117, such as a polyester sling or a metal or polymer wire sling, can cross over the outer surface of the balloon 33115 and be attached to both a distal end of the catheter body 31101 and a proximal end of the nosecone 31105.

Figure 34E:
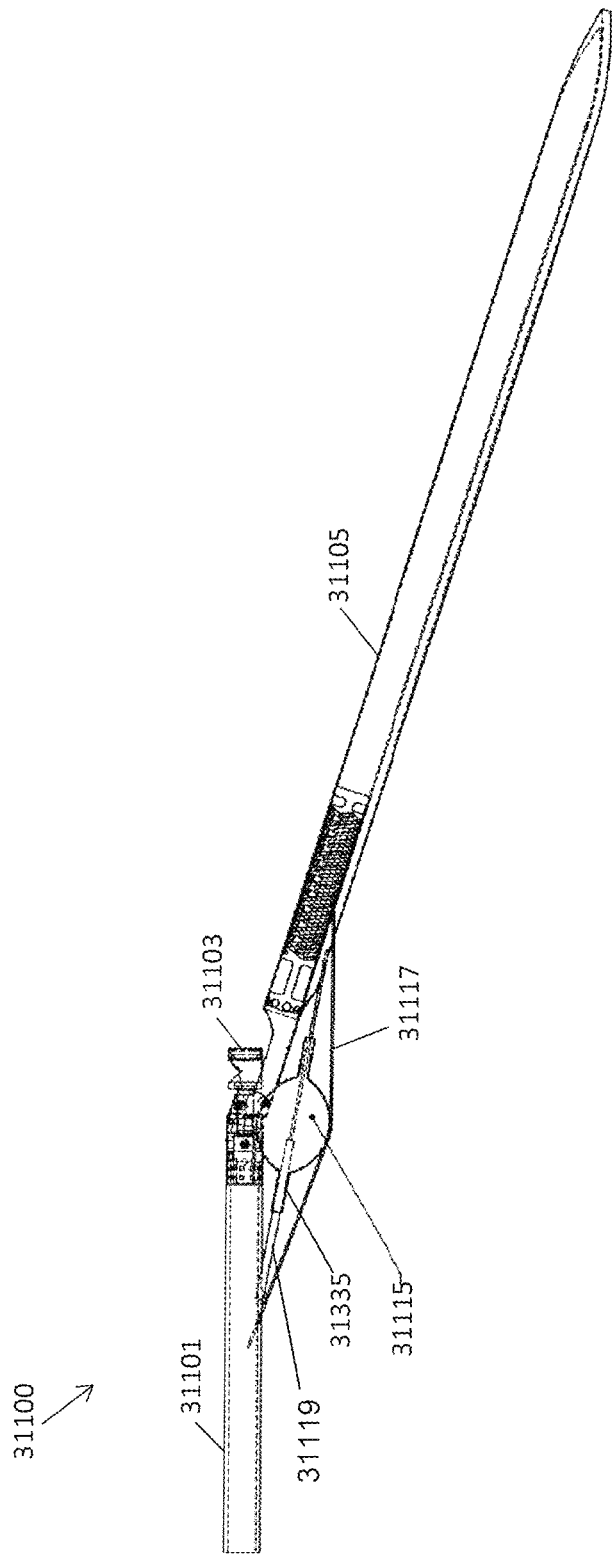
FIG. 34E shows an exemplary detailed version of the atherectomy catheter of FIGS. 34A-34B including a balloon and sling element for deflecting the nosecone and exposing the cutter.

The balloon 31115 can be attached to an inflation tube 31119. As shown in FIGS. 34A-34B, the inflation tube 31119 can be a hypotube running along the outside of the catheter body 31101. In other embodiments, the inflation tube can extend inside the outer shaft 31111 or the drive shaft 31113. Referring to FIG. 34E, the inflation tube 31119 can extend through the proximal and distal end of the balloon 31115. The portion 31335 of the inflation tube 31119 that extends out the distal end of the balloon 31115 can be flexible and extend into a lumen in the wall of the nosecone 31105. The distal end can then translate proximally and distally within the nosecone lumen as the nosecone 31105 is opened and closed, respectively. The extension of the portion 31335 of the inflation tube out of the distal end of the balloon 31115 and into the nosecone 31105 advantageously provides support for the balloon 31115 to ensure both axial alignment and stability of the balloon 31115. In other embodiments, rather than translating the inflation tube 31119 within the nosecone, the inflation tube 31119 can be configured to translate within the catheter body 31101.

In use, the balloon 31115 can be inflated, through the inflation tube 31119, with a gas or liquid. As the balloon 31115 inflates, it can apply force to the center of the sling element 31117. The force on the center of the sling element 31117 can push the center away from the central axis 31110 of the catheter body 31101 and cause the attached edges of the sling element 31117 to pull on the distal end of the catheter body 31101 and the proximal end of the nosecone 31105. The simultaneous pulling on both the catheter body 31101 and the nosecone 31105 can force the catheter 31100 to bend at the hinge point 31109, thereby exposing the cutter 31103 out of the window 31107. In some embodiments, the cutter 31103 can have a diameter that is smaller than the window 31107 to allow it to extend out of the window 31107.

Advantageously, by using the balloon 31115 to open the nosecone 31105, less force is placed on the drive shaft 31113 (relative to designs where tension or compression must be placed on the drive shaft to open the nosecone), thereby improving image quality. Further, the balloon 31115 can advantageously act as an occlusion element to at least partially block blood flow to the imaging element 31292, thereby reducing the amount of saline flush required to obtain a clear image and improving image quality. Further, use of the balloon 31115 to activate deflection can advantageously provide user-adjustable force for engaging the cutter 31103 with a vessel wall, as the balloon 31115 can be adjusted to provide variable urge force. Moreover, in some embodiments, the sling mechanism 31117 can act as a smooth sliding surface against the inside of a vessel, allowing it to maintain contact with the tissue without having an abrupt change in diameter. The sling mechanism 31117 can also advantageously protect the balloon 31115 to avoid popping of the balloon 31115 or peeling of the balloon 31115 away from the catheter body 31101 due to friction.

In order to close the nosecone 31105 and store the cutter 31103, the balloon 31115 is deflated. As the balloon 31115 is deflated, the sling element 31117 becomes less taut, releasing the nosecone 31105 deflection force. In order to fully close the nosecone 31105, a biasing mechanism can be used. Referring to FIGS. 34C-34D, in one embodiment, to close the nosecone 31105, the drive shaft can be pushed distally, causing a distally-facing flange 31555 on the cutter 31103 to engage a nosecone wedge 31557, driving the nosecone 31105 upwards and back into alignment with the outer shaft 31101. The return of the nosecone 31105 to the closed position can also be aided by having a tight concentric fit between a distal end of the nosecone 31105 and the outer shaft 31111 such that, once the distal end of the nosecone 31105 begins to align with outer shaft 31111, it is forced upwards and into alignment. Using a closing mechanism that is distinct from the balloon 31115 advantageously ensures that the nosecone 31105 fully closes, thereby allowing full tissue part-off and packing into the nosecone 31105.

In some embodiments, rather than (or in addition to) closing the nosecone through movement of the drive shaft (as described with respect to FIGS. 34C-34D), the hinge mechanism 31109 can be a living hinge.

The nosecone 31105 can open using the balloon 31115 and sling 31117 while it can close by either moving the drive shaft 31113 and forcing the nosecone 31105 closed over the nosecone wedge 31557 or by use of a living hinge. By allowing the balloon 31115 to open the nosecone 31105, forces are advantageously minimized at the imaging element 31292 during atherectomy. This is less of an issue when closing the nosecone 31105 after cutting, as the closing and packing of the cutter 31103 is carried out after therapy is complete. Further, using either movement of the shaft and the nosecone wedge 31557 or a living hinge to close the nosecone advantageously brings the nosecone 31105 fully on-axis with the catheter body 31101 before the cutter 31103 moves into the nosecone 31105 (as described further below), preventing the cutter 31103 from hitting the nosecone 31105 housing and thus preventing the cutter 31103 from dulling over time.

Further, the catheter 31100 can include a mechanism for packing tissue into the nosecone 31105, such as by moving the drive shaft 31113 axially. In one embodiment, as described above, movement of the drive shaft distally closes the nosecone 31105. Moving the drive shaft 31113 further distally will move the cutter 31103 into the nosecone 31105, thus packing tissue with a distal face of the cutter.

Figure 35:
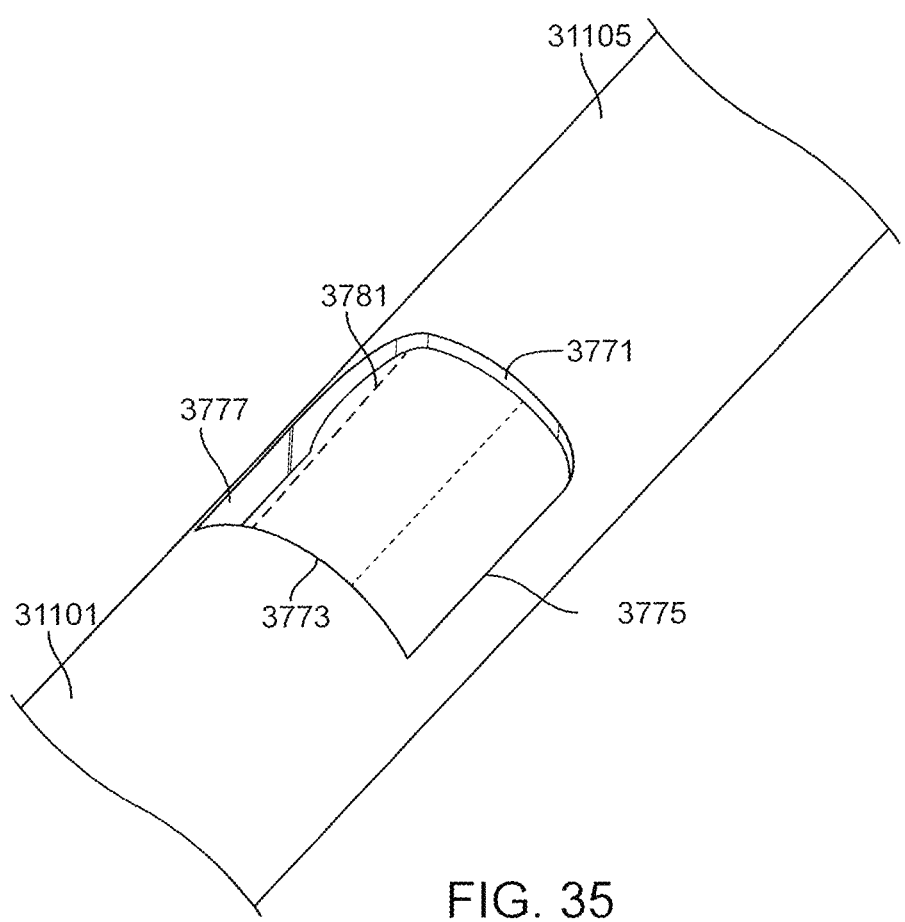
FIG. 35 shows an asymmetric cutting window.

In some embodiments, the cutting window 31107 can be designed so as to further prevent the cutting window 31107 from interfering with the movement of the drive shaft 31113 and cutter 31103 distally. For example, as shown in FIG. 35, the window 31107 can have a distal edge 3771, a proximal edge 3773, a linear edge 3775, and a curvilinear edge 3777. The proximal edge 3773 can have a length that is longer than the distal edge 3771. The curvilinear edge 3777 can curve towards the distal edge 3771. Further, the curvilinear edge 3777 can be configured to be the side towards which the cutter 31103 rotates (as shown by the arrow 3781). Because the cutter 31103, when it is extended into the nosecone to pack tissue, moves distally, it will extend along the curvilinear edge 3777, which will deflect the cutter 31103 into the nosecone 31105, thereby avoiding contact of the cutter 31103 with the distal edge 3771 (which might otherwise occur if the cutter 31103 is slightly off-axis, such as if the nosecone 31105 has not return fully in-line with the catheter body 31101). Avoiding contact of the cutter 31103 with the distal edge 3771 advantageously prevents interference of the cutting window 31107 with movement of the drive shaft and protects the cutter 31103 from dulling over time. In some embodiments, the curvilinear edge 3777 can have a height (along the radial axis of the device) that is greater than the height of the oppose linear edge 3775. Have a greater height can advantageously help prevent tissue from escaping the tissue window, as the tissue tends to spiral and move in the direction that the cutter is moving. The curvilinear edge can be used for the cutting window 31107 in place of or in addition to the closing mechanisms for the hinge (such as the wedge and the living hinge).

Although the balloon/hinge embodiments have been described herein with respect to a catheter having a single drive and imaging shaft, it is to be understood that the same mechanisms could be used with any of the catheters described herein, including the catheters with separate imaging and drive shafts.

Referring to FIGS. 36A-37B, the atherectomy catheters described herein can be used with a handle configured such that the optical fiber can be extended axially a distal location, e.g., with the drive shaft to pack tissue or manipulate the nosecone, without requiring axial movement of the optical fiber at a proximal location, e.g., without requiring movement of the optical fiber assembly with the drive system. Thus, the handle can be designed to completely account for movement of the drive shaft.

In one embodiment, shown in FIGS. 36A-36B, a handle 31800 can include a rigid tube 31802. The proximal portion 31804 of a compliant flexible drive shaft (e.g. a drive shaft used for any of the above described catheters) can be axially constrained relative to the rigid tube 31802 at the proximal end 31808 of the handle 31800. For example, the proximal portion 31804 of the flexible drive shaft can be attached so that it is free to rotate relative to the tube 31802 yet constrained so that it is unable to translate relative to the tube 31802, such as via a rotatable bushing that is translationally locked at the proximal end 31808 of the handle 31800. The rest of the flexible drive shaft can be otherwise unattached to the rigid tube 31802 where it is free to rotate and translate.

When the flexible drive shaft is in the normal or compressed configuration, as shown in FIG. 36A, the proximal portion 31804 of the flexible drive shaft can be coiled or otherwise collapsed within the inner perimeter of the rigid tube 31802. As tension is applied on the flexible drive shaft in the distal direction, the coils can unwind or the distal portion otherwise extend, allowing for relative translation between the distal end of the flexible drive shaft and the rigid tube 31802. Thus, when the flexible drive shaft is in the extended configuration, the proximal portion 31804 of the flexible drive shaft that was coiled or compressed within the rigid tube 31802 can extend out of the distal end 31818 of the rigid tube 31802, as shown in FIG. 36B, allowing the distal end of the flexible drive shaft to be translated distally.

The handle 31800 can allow for a set range of translation that is established by several factors, including the overall length of the distal portion 31804 of the flexible drive shaft, the length of the rigid tube 31802, the radius of curvature of the proximal portion 31804 of the flexible drive shaft which correlates to its ability to collapse, and the inner diameter of the rigid tube 31802 which correlates to its capacity to manage and contain the collapsed distal portion 31804. For example, the amount of translation of the flexible drive shaft can be approximately 1 inch.

In another embodiment of a handle configured to provide all of the axial movement of a drive shaft, referring to FIGS. 37A-37B, a handle 31900 can include a rigid tube 31902 formed into a loop 31903. The proximal portion 31904 of a flexible drive shaft (e.g. a drive shaft used for any of the above described catheters) can be axially constrained relative to the rigid tube 31902 at the proximal end 31908 of the handle 31900. For example, the flexible drive shaft can be locked in place translationally on the proximal handle 31908 via a rotatable bushing 31464. The drive shaft can spin inside of this bushing 31464, but a rib 31923 on the distal end (and a distal bushing 31462) prevent the drive shaft from translating axially.

The rest of the flexible drive shaft can be otherwise unattached to the rigid tube 13902. The distal portion 31904 of the flexible drive shaft can form a loop 13907 within the loop 31903 of the rigid tube 31902. The rigid tube 31902 can be configured such that, as shown in FIG. 37A, when the distal portion 31904 of the flexible drive shaft is in the normal or compressed configuration, the loop 31907 of the flexible drive shaft conforms to the outer perimeter of the loop 31903 of the rigid tube 31902. As tension is applied on the flexible drive shaft in the distal direction, the loop 31907 of the flexible drive shaft will tighten. Accordingly, as shown in FIG. 37B, when the flexible drive shaft is in the extended configuration, the loop 31907 of the flexible drive shaft conforms to the inner perimeter of the loop 31903 of the rigid tube 31902, allowing the distal end of the flexible drive shaft to be translated distally.

The handle 31900 can allow for a set range of translation that is established by the relative difference in length between the outer and inner perimeters of the loop 31903 of the rigid tube 31902. For example, the loop 31907 of the flexible drive shaft can expand from 2 inches to 2.6 inches, allowing for up to 1.8 inches of translation by the flexible drive shaft at the distal end.

In some embodiments, the flexible drive shafts described herein can include a flexible outer tube surrounding an inner coil. The inner coil can spin within the outer tube while the outer tube provides support for the coil to maintain its shape while manipulated.

Both of the handles 31800 and 31900 can include a mechanism on the handle to control the extension of the distal wire. For example, as shown in FIGS. 37A and 37B, the handle 31900 can include a user slide 31910 attached through the rigid tube 31902 to the distal portion 31904 of the flexible drive shaft. The user slide 31910 can slide proximally and distally to control the tensioning or compression of the distal portion of the flexible drive shaft.

The handles 31800 and 31900 can further include a coupling, such as the coupling 31912 configured to couple the respective handle with a drive mechanism. The distal portion of the drive shaft can be placed in-line with the drive system, enabling translation of the flexible drive shaft without requiring complex exterior slide mechanisms to accommodate the fixed length optical fiber.

Using a handle, such as the handles 31800 and 31900 shown in FIGS. 36A-37B, configured so that the inner drive shaft can be extended axially at the distal end without requiring axial movement of the drive shaft at the proximal end, advantageously allows the handle to be locked in position relative to the drive mechanism, thereby eliminating the need for a linear slide in the drive mechanism to manage the fixed length of the optical fiber, simplifying the mechanical design and the user requirements.

In one embodiment, the atherectomy catheters described herein include a flush port close to the cutter. The flush port can be used to deliver flushing fluid to the area of imaging, thereby improving image quality. Referring to FIGS. 37A-37B, in some embodiments, the flushing can be activated through a luer 31998 on the handle 31900. The luer 31998 can be located just distal of the user ring 31910 on the handle 31900 and can be part of a rotating hemo stasis valve component in the handle body.

Figure 38:
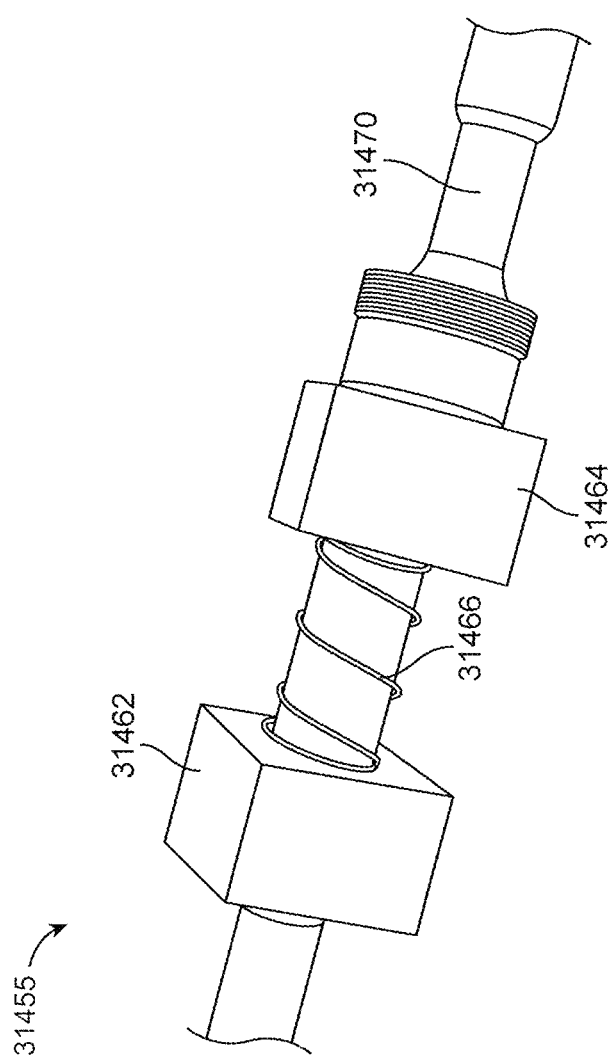
FIG. 38 shows an exemplary optical alignment feature of a catheter handle for connection to a drive system.
Figure 39:
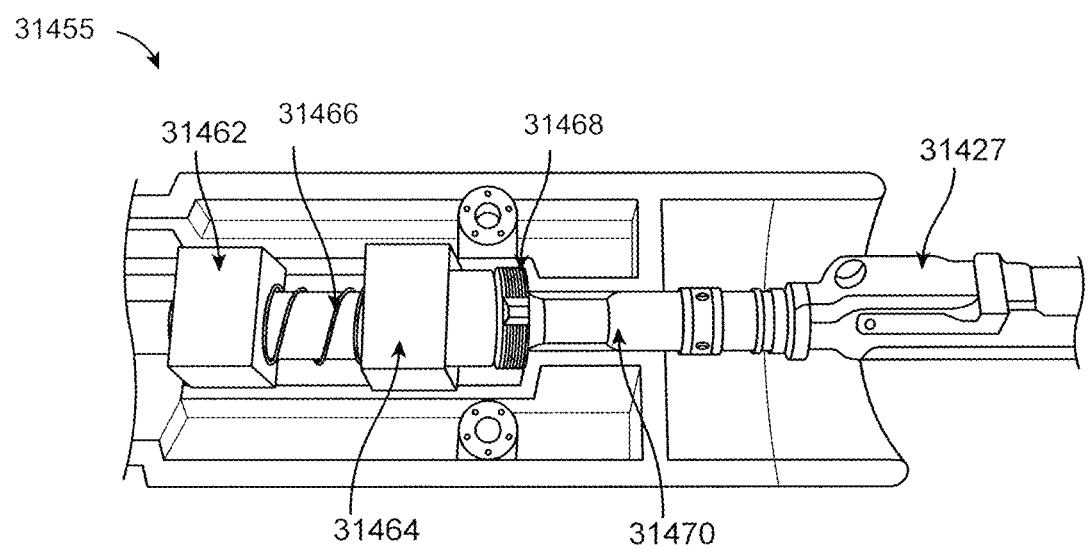
FIG. 39 shows an exemplary optical connection feature of a handle that includes the optical alignment feature of FIG. 38.
Figure 40:
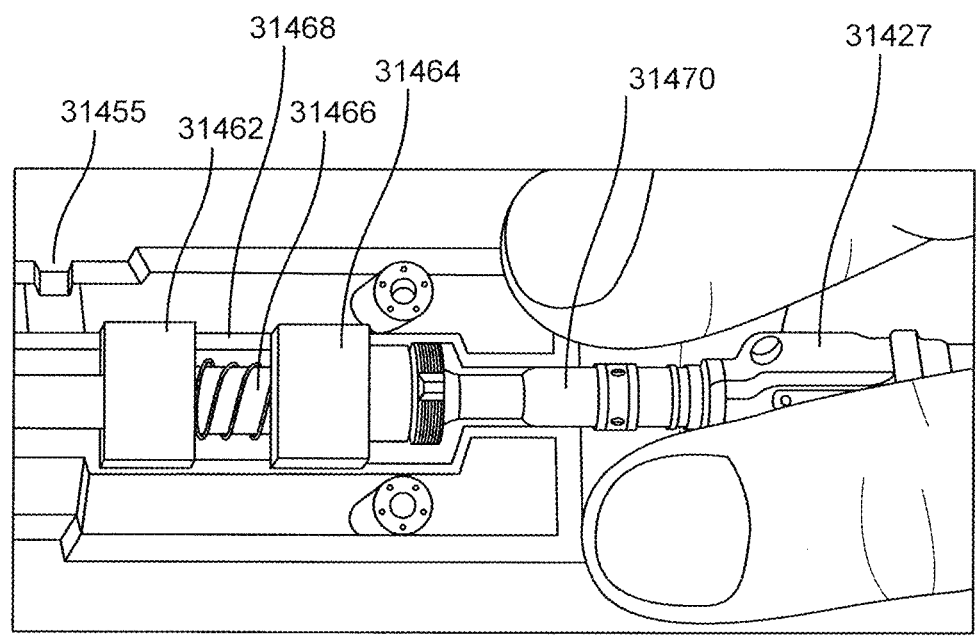
FIG. 40 shows the optical connection of FIG. 39 in a compressed configuration.

Referring to FIGS. 38-40, any of the handles described herein can include an optical connector mechanism 31455 mechanism to establish and maintain the connection between the catheter and the drive system 31400. The connector mechanism 31455 can be a spring-loaded piston mechanism includes a distal bushing 31462, a proximal bushing 31464, and a compression spring 31466. The connector mechanism 31455 can produce a spring force along the optical fiber axis to maintain the connection between the optical connector 31427 and the optical connector of the drive system to which the handle is connected.

As shown in FIGS. 39 and 40, the connector mechanism 31455 can be configured to sit in a restraining track 31468 in the handle. The two bushings 31462 and 31464 can provide multiple functions including: (1) provide bearing surfaces for catheter rotation; (2) serve as end stops between which the compression spring 31466 is captured; and (3) the proximal bushing can slide within the handle enclosure, allowing the connector and catheter assembly to slide axially during connector engagement/disengagement. The bushings 31462, 31464 and the spring 31466 can lie concentric to a fiber coupler 31470, which can link the optical connector 31427 of the drive system (see FIG. 39) to the bushing-spring assembly. In some embodiments, the fiber coupler 31470 can also include a flange feature which serves to push on the proximal bushing 31464 to compress the bushing-spring assembly, thereby maintaining connection to the drive system. In some embodiments, a compression spring force below 1 lb, such as below 0.75 lbs produces the proper connection of the optical connector interface while avoiding image distortion. Further, in some embodiments, the spring force of the compression spring 31466 is greater than 0.05 lbs., such as greater than 0.1 lbs. to overcome material friction. In some embodiments, the spring-loaded mechanism can also provide compliance for the handle, allowing for slight movement of the proximal end of the fiber relative to the handle.

Any of the catheters described herein can further include a guidewire lumen, such as a monorail guidewire lumen. In some embodiments, the monorail guidewire lumen can run parallel to one or more of the struts or markers in the imaging window, thereby not hindering the imaging of the vessel. In other embodiments, the guidewire lumen can be used an imaging marker to identify the orientation of the device.

Any of the shafts described herein (such as the imaging shaft, drive shaft, or outer shafts) can be made of a multi-layer coil. The shafts can include, for example, stainless steel. In one exemplary embodiments, the shaft can be made of 8 adjacent filars wound in one direction with another layer of 8 filars wound in the opposite direction on top of the first layer. The number of filars on each layer may vary as might the diameter of the filars. The drive cable may also comprise 3 layers of filars, adjacent layers being wound in opposite directions.

The catheters described herein can be driven with a reusable drive system, which can provide the torque for the drive shaft and/or optical fiber as well as the optical connection from a light source. Exemplary drive shafts are described in U.S. patent application Ser. No. 13/654,357, titled "ATHERECTOMY CATHETERS AND NON-CONTACT ACTUATION MECHANISM FOR CATHETERS," filed Oct. 17, 2012 and International Patent Application titled "ATHERECTOMY CATHETER DRIVE ASSEMBLIES," filed herewith, all of which are incorporated by reference in their entireties.

Figure 14:
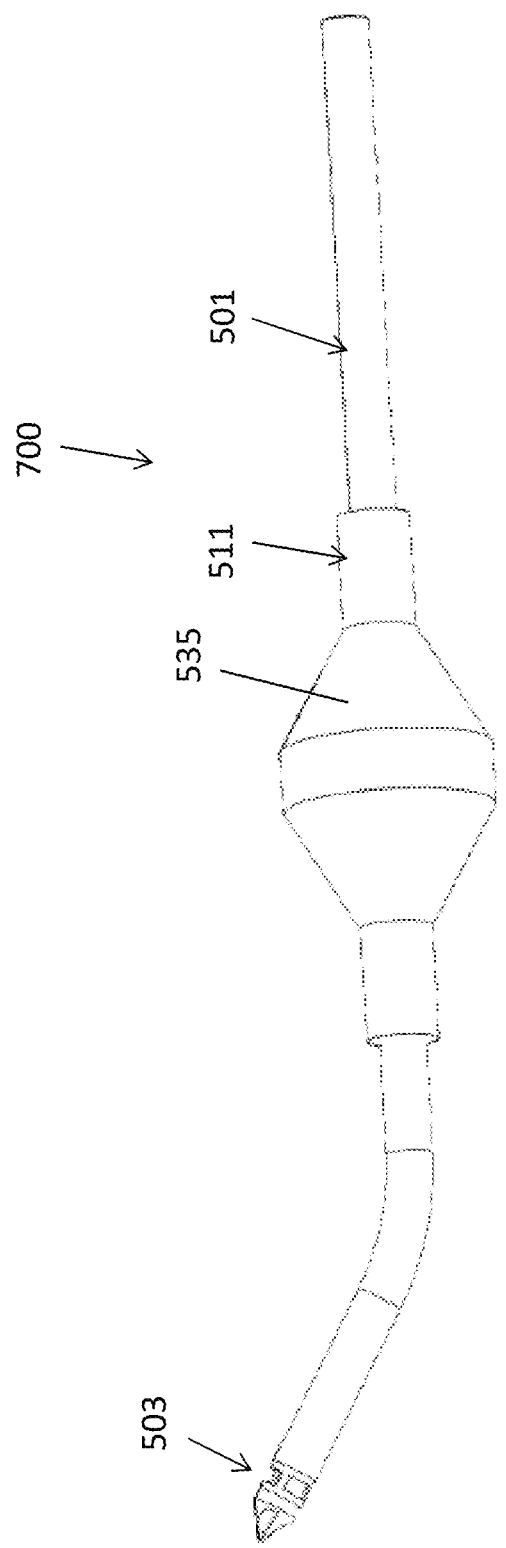
FIG. 14 shows an occlusion-crossing catheter.
Figure 15B:
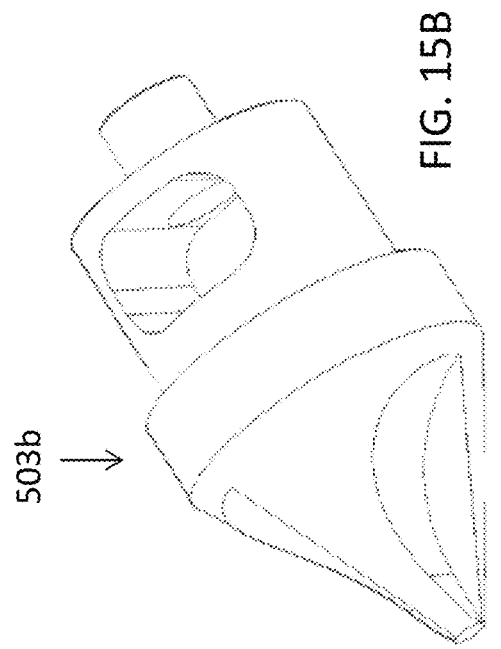
FIGS. 15A-15D show examples of tips that may be used for occlusion-crossing catheters.
Figure 15D:
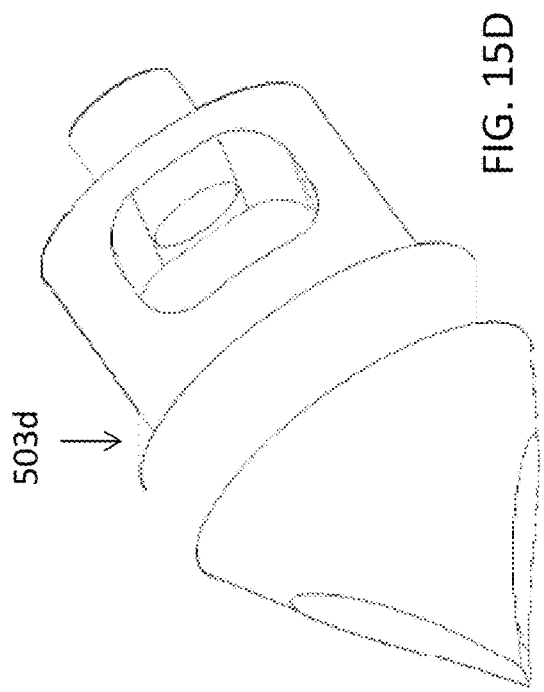
Figure 15A:
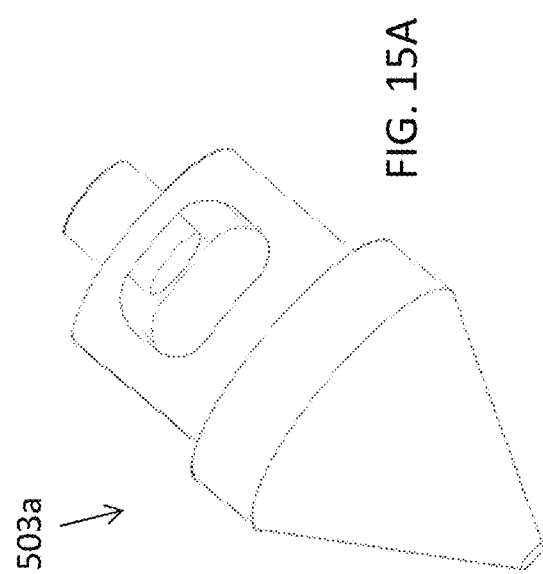
Figure 15C:
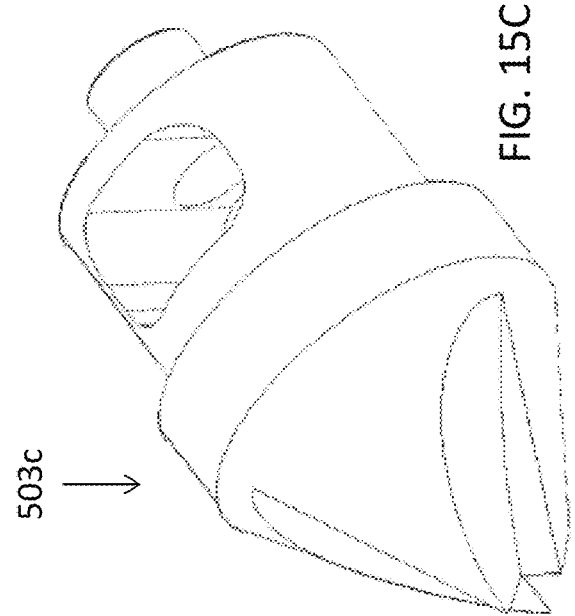

Referring to FIG. 14, an occlusion-crossing catheter 700 can include an outer sheath 511 with a tapered occluding balloon 535 attached thereto. In some embodiments, the cutting head 503 of the catheter 700 can be interchangeable, allowing the device to be more widely useable and adaptable. For example, the tip 503 can be interchangeable between a tip that is cone-shaped and burred (as shown by tip 503*a* in FIG. 15A), a tip that is fluted with cutting edges (as shown by tip 503*b* in FIG. 15B), a tip that is includes forward-projecting tips for aggressive cutting (as shown by tip 503*c* in FIG. 15C), and/or a tip that is chisel-like with a single sharp blade (as shown by tip 503*d* in FIG. 15D). In order to allow the tips to be interchangeable, the tips 503 can, for example, have a threaded proximal edge that threads in the opposite direction of rotation of the head 503. In other embodiments, the proximal edges can snap or otherwise fit in and out of the elongate body 501 of the device 700.

Further, as described above, the catheters described herein can be used with optical coherence tomography imaging. Exemplary optical coherence tomography systems are described in copending Patent Applications: U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; and International Patent Application titled "OPTICAL COHERENCE TOMOGRAPHY WITH GRADED INDEX FIBER FOR BIOLOGICAL IMAGING," filed herewith, all of which are incorporated by reference in their entireties. In some embodiments, side-firing optical fibers can be used in place of the reflective elements to direct the OCT signal into the tissue.

Additional details pertinent to the present invention, including materials and manufacturing techniques, may be employed as within the level of those with skill in the relevant art. The same may hold true with respect to method-based aspects of the invention in terms of additional acts commonly or logically employed. Further, it is to be understood that although specific embodiments are described above, elements of one or more of each of the embodiments can be combined or added while still falling within the scope of this disclosure. Thus, it is contemplated that any optional feature of the inventive variations described may be set forth and claimed independently, or in combination with any one or more of the features described herein. Likewise, reference to a singular item, includes the possibility that there is a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An atherectomy catheter device, the device comprising:
   an elongate body;
   a hollow distal tip extending from a distal end of the elongate body;
   a drive shaft extending distally to proximally within the elongate body;
   an optical coherence tomography fiber running along a central longitudinal axis of the drive shaft an entire length of the drive shaft; and
   a cutting and imaging assembly coupled to the drive shaft, the cutting and imaging assembly having a distal cutting edge and a slot configured to hold a distal end of the fiber therein, the slot having a length that is equal to or greater than a radius of the cutting and imaging assembly such that the fiber extends from the drive shaft straight through the cutting and imaging assembly into the slot without bending.

2. The device of claim 1, further comprising a reflective element positioned within the slot and configured to radially direct light from the fiber out of the elongate body.

3. The device of claim 2, wherein the reflective element is oriented at an angle relative to the longitudinal axis of the drive shaft.

4. The device of claim 3, wherein the angle is 35-55 degrees.

5. The device of claim 1, wherein the distal end of the fiber is less than 3 mm from the distal cutting edge.

6. The device of claim 1, wherein the fiber is fixed to the slot, but is otherwise free to float within the cutting and imaging assembly and the drive shaft.

7. The device of claim 1, wherein the cutting and imaging assembly is configured to extend into the hollow distal tip to pack tissue into the hollow distal tip.

8. The device of claim 1, wherein the hollow distal tip is configured to bend away from the elongate body.

9. The device of claim 8, wherein the drive shaft is configured to move proximally or distally to bend the hollow distal tip away from the elongate body.

10. The device of claim 8, wherein bending the hollow distal tip relative to the elongate body exposes the distal cutting edge.

11. The device of claim 1, wherein the drive shaft is configured to rotate the cutting and imaging assembly relative to the elongate body.

12. The device of claim 1, further comprising a balloon wrapped around portions of the elongate body and the hollow distal tip while leaving the distal cutting edge exposed, wherein the balloon is configured to urge the distal cutting edge against a vessel wall and occlude blood flow therearound.

13. The device of claim 12, wherein the balloon is crescent-shaped.

14. The device of claim 1, wherein the cutting and imaging assembly is configured to rotate relative to the elongate body and the hollow distal tip.

15. The device of claim 1, further comprising a handle attached to the elongate body, the handle including:
   a cylindrical fiber holding chamber at a proximal end of the catheter device and configured to rotate with the drive shaft, the fiber holding chamber having an inner region into which the fiber extends; and a fiber coupling region configured to couple the fiber to a light source, wherein the fiber and the drive shaft are configured to move axially within the handle relative to the cylindrical fiber holding chamber and fiber coupling region, and wherein the fiber is configured to bend within the fiber holding chamber as the fiber and the drive shaft move axially.

16. The device of claim 15, wherein the handle further includes a drive shaft tensioning spring configured such that, when the drive shaft is moved proximally, the spring compresses to apply a controlled tensile load on the drive shaft.

* * * * *